(12) United States Patent
Sharma et al.

(10) Patent No.: US 11,633,476 B2
(45) Date of Patent: *Apr. 25, 2023

(54) STABLE FORMULATIONS OF PROGRAMMED DEATH RECEPTOR 1 (PD-1) ANTIBODIES AND METHODS OF USE THEREOF

(71) Applicant: Merck Sharp & Dohme LLC, Rahway, NJ (US)

(72) Inventors: Manoj K. Sharma, Littleton, MA (US); Wendy Benjamin, North Brunswick, NJ (US); Sarita Mittal, Bridgewater, NJ (US); Ashwin Basarkar, Keasbey, NJ (US); Chakravarthy Nachu Narasimhan, Scotch Plains, NJ (US); Ramesh S. Kashi, Warren, NJ (US); Mohammed Shameem, Nanuet, NY (US); Soumendu Bhattacharya, East Windsor, NJ (US); Yogita Krishnamachari, Scotch Plains, NJ (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 531 days.

This patent is subject to a terminal disclaimer.

(21) Appl. No.: 16/609,612

(22) PCT Filed: May 1, 2018

(86) PCT No.: PCT/US2018/030459
§ 371 (c)(1),
(2) Date: Oct. 30, 2019

(87) PCT Pub. No.: WO2018/204368
PCT Pub. Date: Nov. 8, 2018

(65) Prior Publication Data
US 2020/0147213 A1    May 14, 2020

Related U.S. Application Data

(60) Provisional application No. 62/500,238, filed on May 2, 2017.

(51) Int. Cl.
| | | |
|---|---|---|
| *A61K 39/395* | (2006.01) | |
| *A61K 9/19* | (2006.01) | |
| *A61K 47/18* | (2017.01) | |
| *A61K 47/26* | (2006.01) | |
| *A61K 47/34* | (2017.01) | |

(52) U.S. Cl.
CPC ......... *A61K 39/39591* (2013.01); *A61K 9/19* (2013.01); *A61K 39/3955* (2013.01); *A61K 47/183* (2013.01); *A61K 47/26* (2013.01); *A61K 47/34* (2013.01)

(58) Field of Classification Search
CPC .............. A61K 9/19; A61K 39/39591; A61K 39/3955; A61K 47/183; A61K 47/26; A61K 47/34
See application file for complete search history.

(56) References Cited

U.S. PATENT DOCUMENTS

| | | | |
|---|---|---|---|
| 4,401,820 | A | 8/1983 | Chibata et al. |
| 4,816,567 | A | 3/1989 | Cabilly et al. |
| 5,262,296 | A | 11/1993 | Ogawa et al. |
| 5,624,821 | A | 4/1997 | Winter et al. |
| 5,762,905 | A | 6/1998 | Burton et al. |
| 6,171,586 | B1 | 1/2001 | Lam et al. |
| 6,267,958 | B1 | 7/2001 | Andya et al. |
| 6,329,511 | B1 | 12/2001 | Vasquez et al. |
| 6,818,216 | B2 | 11/2004 | Young et al. |
| 6,875,432 | B2 | 4/2005 | Liu et al. |
| 7,247,707 | B2 | 7/2007 | Besman et al. |
| 7,364,736 | B2 | 4/2008 | Boyle et al. |
| 7,374,762 | B2 | 5/2008 | Amphlett et al. |
| 7,375,193 | B2 | 5/2008 | Baca et al. |
| 7,563,869 | B2 | 7/2009 | Honjo et al. |
| 7,592,004 | B2 | 9/2009 | Kaisheva et al. |

(Continued)

FOREIGN PATENT DOCUMENTS

| | | |
|---|---|---|
| AU | 2010200784 A1 | 3/2010 |
| CA | 2918888 A1 | 1/2015 |

(Continued)

OTHER PUBLICATIONS

Kang J et al. Rapid formulation development for monoclonal antibodies. BioProcess International, Apr. 2016, 14(4), 40-45. (Year: 2016).*

(Continued)

*Primary Examiner* — Kimberly Ballard
(74) *Attorney, Agent, or Firm* — Sarah L. Hooson; Alysia A. Finnegan

(57) ABSTRACT

The invention relates to stable formulations of antibodies against human programmed death receptor PD-1, or antigen binding fragments thereof. In some embodiments the formulations of the invention comprise between 5-200 mg/mL anti-PD-1 antibody, or antigen binding fragment thereof. The invention further provides methods for treating various cancers with stable formulations of the invention. In some embodiments of the methods of the invention, the formulations are administered to a subject by intravenous or subcutaneous administration.

21 Claims, 11 Drawing Sheets
Specification includes a Sequence Listing.

(56) References Cited

U.S. PATENT DOCUMENTS

| | | | |
|---|---|---|---|
| 7,615,213 B2 | 11/2009 | Kasaian et al. |
| 7,635,473 B2 | 12/2009 | Warne et al. |
| 7,662,384 B2 | 2/2010 | Ramakrishnan et al. |
| 7,666,413 B2 | 2/2010 | Liu et al. |
| 7,691,379 B2 | 4/2010 | Allan |
| 7,705,132 B2 | 4/2010 | Rehder et al. |
| 7,740,842 B2 | 6/2010 | Arvinte et al. |
| 7,833,525 B2 | 11/2010 | Shenoy et al. |
| 7,959,922 B2 | 6/2011 | Bakker et al. |
| 7,960,516 B2 | 6/2011 | Matheus et al. |
| 7,993,645 B2 | 8/2011 | Benson et al. |
| 7,998,477 B2 | 8/2011 | Yakovlevsky et al. |
| 8,034,906 B2 | 10/2011 | Borhani et al. |
| 8,067,547 B2 | 11/2011 | Ewert et al. |
| 8,142,776 B2 | 3/2012 | Liu et al. |
| 8,168,760 B2 | 5/2012 | Borhani et al. |
| 8,216,583 B2 | 7/2012 | Kruase et al. |
| 8,221,759 B2 | 7/2012 | Pilkington et al. |
| 8,263,080 B2 | 9/2012 | Katsikis et al. |
| 8,293,883 B2 | 10/2012 | Presta |
| 8,399,712 B2 | 3/2013 | Schultheiss et al. |
| 8,580,297 B2 | 11/2013 | Essler et al. |
| 8,747,847 B2 | 6/2014 | Rotem-Yehudar et al. |
| 8,703,126 B2 | 8/2014 | Liu et al. |
| 8,933,075 B2 | 1/2015 | Wang et al. |
| 9,220,776 B2 * | 12/2015 | Sharma ............. C07K 16/2818 |
| 9,273,123 B2 | 3/2016 | Shenoy et al. |
| 9,278,131 B2 | 3/2016 | Dauty et al. |
| 9,592,297 B2 | 3/2017 | Xiang et al. |
| 9,605,051 B2 | 3/2017 | Soane et al. |
| 9,713,641 B2 | 7/2017 | Hicklin et al. |
| 9,782,470 B2 | 10/2017 | Bhambhani et al. |
| 9,926,371 B2 | 3/2018 | Liu et al. |
| 9,963,500 B2 | 5/2018 | Vora et al. |
| 10,072,072 B2 | 9/2018 | Vora et al. |
| 10,188,730 B2 | 1/2019 | Liang |
| 10,550,185 B2 | 2/2020 | Bernett et al. |
| 10,787,518 B2 | 9/2020 | Bernett et al. |
| 10,793,632 B2 | 10/2020 | Bernett et al. |
| 2003/0138417 A1 | 7/2003 | Kaisheva et al. |
| 2004/0091490 A1 | 5/2004 | Johnson et al. |
| 2005/0037062 A1 | 2/2005 | Cote et al. |
| 2005/0101770 A1 | 5/2005 | Presta |
| 2006/0029599 A1 | 2/2006 | Kaisheva et al. |
| 2006/0057702 A1 | 3/2006 | Rosenthal et al. |
| 2006/0088523 A1 | 4/2006 | Andya et al. |
| 2006/0210557 A1 | 9/2006 | Luisi et al. |
| 2006/0210567 A1 | 9/2006 | Collins et al. |
| 2006/0246004 A1 | 11/2006 | Adams et al. |
| 2006/0286103 A1 | 12/2006 | Kolhe et al. |
| 2007/0009526 A1 | 1/2007 | Benson et al. |
| 2007/0009541 A1 | 1/2007 | Amphlett et al. |
| 2007/0048315 A1 | 3/2007 | Presta |
| 2007/0053900 A1 | 3/2007 | Liu et al. |
| 2007/0059803 A1 | 3/2007 | Oppmann et al. |
| 2007/0065437 A1 | 3/2007 | Elson et al. |
| 2007/0184050 A1 | 8/2007 | Ishikawa et al. |
| 2007/0190047 A1 | 8/2007 | Brych et al. |
| 2008/0003220 A1 | 1/2008 | Gokarn |
| 2008/0050375 A1 | 2/2008 | Davies et al. |
| 2008/0057070 A1 | 3/2008 | Long et al. |
| 2008/0112953 A1 | 5/2008 | Mcauley et al. |
| 2008/0124326 A1 | 5/2008 | Rehder et al. |
| 2008/0152658 A1 | 6/2008 | Dagan et al. |
| 2008/0213282 A1 | 9/2008 | Jacob |
| 2008/0248048 A1 | 10/2008 | Fish et al. |
| 2008/0254026 A1 | 10/2008 | Long et al. |
| 2008/0286270 A1 | 11/2008 | Oliver et al. |
| 2008/0311119 A1 | 12/2008 | Maloney et al. |
| 2009/0042315 A1 | 2/2009 | Li et al. |
| 2009/0060906 A1 * | 3/2009 | Barry ............... A61K 39/39591 424/131.1 |
| 2009/0130119 A1 | 5/2009 | Abate et al. |
| 2009/0162352 A1 | 6/2009 | Adler et al. |
| 2009/0181027 A1 | 7/2009 | Dal Monte et al. |
| 2009/0208492 A1 | 8/2009 | O'Connor et al. |
| 2009/0217401 A1 | 8/2009 | Korman et al. |
| 2009/0285802 A1 | 11/2009 | Igawa et al. |
| 2009/0291076 A1 | 11/2009 | Morichika et al. |
| 2009/0304706 A1 | 12/2009 | Lu et al. |
| 2009/0311253 A1 | 12/2009 | Ghayur et al. |
| 2010/0021461 A1 | 1/2010 | Burke et al. |
| 2010/0055111 A1 | 3/2010 | Sharma et al. |
| 2010/0137213 A1 | 6/2010 | Fernandez et al. |
| 2010/0209434 A1 | 8/2010 | Bishop et al. |
| 2010/0209437 A1 | 8/2010 | Elson et al. |
| 2010/0266617 A1 | 10/2010 | Carven et al. |
| 2010/0272731 A1 | 10/2010 | Presta et al. |
| 2010/0278822 A1 | 11/2010 | Fraunhofer et al. |
| 2010/0286038 A1 | 11/2010 | Antochshuk et al. |
| 2010/0303827 A1 | 12/2010 | Sharma et al. |
| 2010/0316638 A1 | 12/2010 | Gurny et al. |
| 2011/0014203 A1 | 1/2011 | Nilsson et al. |
| 2011/0059079 A1 | 3/2011 | Babuka et al. |
| 2011/0060290 A1 | 3/2011 | Bonk et al. |
| 2011/0086038 A1 | 4/2011 | Hope et al. |
| 2011/0123550 A1 | 5/2011 | Shibayama et al. |
| 2011/0171217 A1 | 7/2011 | Badkar et al. |
| 2011/0226650 A1 | 9/2011 | Gokarn et al. |
| 2011/0229490 A1 | 9/2011 | Li et al. |
| 2011/0256135 A1 | 10/2011 | Fraunhofer et al. |
| 2011/0300135 A1 | 12/2011 | Lobo et al. |
| 2011/0318343 A1 | 12/2011 | Kaisheva et al. |
| 2012/0039876 A1 | 2/2012 | Oliver et al. |
| 2012/0076784 A1 | 3/2012 | Matheus et al. |
| 2012/0128687 A1 | 5/2012 | Adler et al. |
| 2012/0183531 A1 | 7/2012 | Lucas et al. |
| 2012/0231972 A1 | 9/2012 | Golyshin et al. |
| 2013/0022625 A1 | 1/2013 | Igawa et al. |
| 2013/0058958 A1 | 3/2013 | Bowen et al. |
| 2013/0108651 A1 | 5/2013 | Carven et al. |
| 2013/0186797 A1 | 7/2013 | Walsh |
| 2014/0044708 A1 | 2/2014 | Dauty et al. |
| 2014/0044727 A1 | 2/2014 | Monck et al. |
| 2014/0178401 A1 | 6/2014 | Nabozny et al. |
| 2014/0206845 A1 | 7/2014 | Kameoka et al. |
| 2014/0227250 A1 | 8/2014 | Li et al. |
| 2014/0234296 A1 | 8/2014 | Sharma et al. |
| 2014/0314714 A1 | 10/2014 | Honjo et al. |
| 2014/0348841 A1 | 11/2014 | Schebye et al. |
| 2015/0071936 A1 | 3/2015 | Mendiratta et al. |
| 2015/0086559 A1 | 3/2015 | Mueller et al. |
| 2015/0100030 A1 | 4/2015 | Dix et al. |
| 2015/0110783 A1 | 4/2015 | Lu et al. |
| 2015/0258209 A1 | 9/2015 | Benz et al. |
| 2015/0290325 A1 | 10/2015 | Kashi et al. |
| 2015/0307606 A1 | 10/2015 | Basarkar et al. |
| 2015/0359900 A1 | 12/2015 | Wang et al. |
| 2016/0022814 A1† | 1/2016 | Petit et al. |
| 2016/0045615 A1 | 2/2016 | Li et al. |
| 2016/0090419 A1 | 3/2016 | Morichika et al. |
| 2016/0106835 A1 * | 4/2016 | Hoos ...................... A61P 35/00 424/133.1 |
| 2016/0166685 A1 | 6/2016 | Cheung et al. |
| 2016/0176963 A1 | 6/2016 | Maurer et al. |
| 2016/0222116 A1 | 8/2016 | Korman |
| 2016/0244521 A1 | 8/2016 | White et al. |
| 2016/0355589 A1 | 12/2016 | Williams et al. |
| 2017/0051039 A1 | 2/2017 | Gombotz et al. |
| 2017/0056347 A1 | 3/2017 | Glick et al. |
| 2017/0097333 A1 | 4/2017 | Bhagwat et al. |
| 2017/0210792 A1 | 7/2017 | Mason et al. |
| 2017/0210812 A1 | 7/2017 | Wong et al. |
| 2017/0216433 A1 | 8/2017 | Li et al. |
| 2017/0360929 A1 | 12/2017 | Sinha et al. |
| 2018/0237524 A1 | 8/2018 | Reichert et al. |
| 2018/0339045 A1 | 11/2018 | Li et al. |
| 2020/0055938 A1 | 2/2020 | Desai et al. |
| 2020/0147213 A1 | 5/2020 | Sharma et al. |
| 2020/0206350 A1 | 7/2020 | Chu et al. |

(56) References Cited

U.S. PATENT DOCUMENTS

| | | |
|---|---|---|
| 2020/0262922 A1 | 8/2020 | Bhattacharya et al. |
| 2022/0002410 A1 | 1/2022 | Antochshuk et al. |

FOREIGN PATENT DOCUMENTS

| | | |
|---|---|---|
| CA | 2956000 A1 | 2/2016 |
| CN | 101172100 A | 5/2008 |
| EP | 1324776 B1 | 4/2001 |
| EP | 1801123 A2 | 6/2007 |
| EP | 2116265 A2 | 11/2009 |
| EP | 2238985 B1 | 8/2012 |
| EP | 2275119 B1 | 9/2013 |
| EP | 3117837 A1 | 6/2017 |
| EP | 3357508 A1 | 8/2018 |
| JP | 2016525117 A | 8/2016 |
| KR | 20100054780 A | 5/2010 |
| RU | 2494107 C2 | 5/2006 |
| RU | 2348615 C2 | 3/2009 |
| RU | 2560701 C2 | 8/2015 |
| RU | 2015123476 A | 10/2015 |
| RU | 2589691 C2 | 7/2016 |
| WO | 1989011297 A1 | 11/1989 |
| WO | 199704801 A1 | 2/1997 |
| WO | 2000053631 A1 | 9/2000 |
| WO | 2001018051 A2 | 3/2001 |
| WO | 2001030393 A2 | 3/2001 |
| WO | 2002072636 A2 | 9/2002 |
| WO | 2002102303 A2 | 12/2002 |
| WO | 03009817 A2 | 2/2003 |
| WO | 2003009817 A1 | 2/2003 |
| WO | 2003039485 A2 | 5/2003 |
| WO | 2003086310 A2 | 10/2003 |
| WO | 2004024068 A2 | 3/2004 |
| WO | 2004055164 A2 | 7/2004 |
| WO | 2004056875 A1 | 7/2004 |
| WO | 2004071517 A2 | 8/2004 |
| WO | 2004081190 A2 | 9/2004 |
| WO | 2005013972 A1 | 2/2005 |
| WO | 2005120571 A2 | 12/2005 |
| WO | 2006121168 A1 | 11/2006 |
| WO | 2007019232 A2 | 2/2007 |
| WO | 2007024846 A2 | 3/2007 |
| WO | 2007092772 A2 | 8/2007 |
| WO | 2007110339 A1 | 10/2007 |
| WO | 2007147019 A2 | 12/2007 |
| WO | 2008076321 A1 | 6/2008 |
| WO | 2008079290 A2 | 7/2008 |
| WO | 2008086395 A2 | 7/2008 |
| WO | 2008103473 A1 | 8/2008 |
| WO | 2008121301 A1 | 10/2008 |
| WO | 2008/157409 A1 | 12/2008 |
| WO | 2008153610 A2 | 12/2008 |
| WO | 2008156712 A1 | 12/2008 |
| WO | 2009009407 A1 | 1/2009 |
| WO | 2009043933 A1 | 4/2009 |
| WO | 2009120684 A1 | 10/2009 |
| WO | 2009126688 A2 | 10/2009 |
| WO | 2010032220 A1 | 3/2010 |
| WO | 2010062372 A2 | 6/2010 |
| WO | 2010069858 A1 | 6/2010 |
| WO | 2010102241 A1 | 9/2010 |
| WO | 2010129469 A1 | 11/2010 |
| WO | 2011012637 A1 | 2/2011 |
| WO | 2011017070 A1 | 2/2011 |
| WO | 2011024862 A1 | 3/2011 |
| WO | 2011056772 A1 | 5/2011 |
| WO | 2011097372 A2 | 8/2011 |
| WO | 2011139718 A1 | 11/2011 |
| WO | 2012010799 A1 | 1/2012 |
| WO | 2012018538 A2 | 2/2012 |
| WO | 2012135035 A1 | 10/2012 |
| WO | 2012165917 A1 | 12/2012 |
| WO | 2013063468 A1 | 5/2013 |
| WO | 2013151999 A1 | 10/2013 |
| WO | 2014004436 A2 | 1/2014 |
| WO | 2014036071 A1 | 3/2014 |
| WO | 2014036076 A1 | 3/2014 |
| WO | 2015009856 A2 | 1/2015 |
| WO | 2015011199 | 1/2015 |
| WO | 2015038777 A1 | 3/2015 |
| WO | 2015038782 A1 | 3/2015 |
| WO | 2015038811 A2 | 3/2015 |
| WO | 2015038818 A2 | 3/2015 |
| WO | 2015143343 A2 | 9/2015 |
| WO | 2016024228 A1 | 2/2016 |
| WO | 2016028656 A1 | 2/2016 |
| WO | 2016028672 A1 | 2/2016 |
| WO | 2016070051 A2 | 5/2016 |
| WO | 2016100882 A1 | 6/2016 |
| WO | 2016118654 A1 | 7/2016 |
| WO | 2016137850 A1 | 9/2016 |
| WO | 2016140717 A1 | 9/2016 |
| WO | 2016/168716 A1 † | 10/2016 |
| WO | 2016168716 A1 | 10/2016 |
| WO | 2016176504 A1 | 11/2016 |
| WO | 2016200782 A1 | 12/2016 |
| WO | 2017009813 A1 | 1/2017 |
| WO | 2017021526 A1 | 2/2017 |
| WO | 2017030823 A2 | 2/2017 |
| WO | 2017037203 A1 | 3/2017 |
| WO | 2017040864 A1 | 3/2017 |
| WO | 2017048824 A1 | 3/2017 |
| WO | 2017053748 A2 | 3/2017 |
| WO | 2017/054646 A1 † | 4/2017 |
| WO | 2017054646 A1 | 4/2017 |
| WO | 2017075124 A1 | 5/2017 |
| WO | 2017089895 A1 | 6/2017 |
| WO | 2017112621 A1 | 6/2017 |
| WO | 2017198741 A1 | 11/2017 |
| WO | 2018091729 A2 | 5/2018 |
| WO | 2018158332 A1 | 9/2018 |
| WO | 2018160722 A1 | 9/2018 |
| WO | 2018187057 A1 | 10/2018 |
| WO | 2018204343 A1 | 11/2018 |
| WO | 2018204374 A1 | 11/2018 |

OTHER PUBLICATIONS

Wang Y et al. Combination of EP4 antagonist MF-766 and anti-PD-1 promotes anti-tumor efficacy by modulating both lymphocytes and myeloid cells. Oncoimmunology, 2021, 10(1): e1896643, 16 pages. (Year: 2021).*
Borwankar, A.U. et al., Viscosity Reduction of a Concentrated Monoclonal Antibody with Arginine HCl and Arginine Glutamate, Ind. Eng. Chem. Res., 2016, 11225-11234, 55(43).
Hermans, J. et al., Physicochemical Parameters Affecting the Electrospray Ionization Efficiency of Amino Acids after Acylation, Analytical Chemistry, 2017, 9159-9166, 89(17).
Mianzini, B. et al., Polymer-supported syntheses of oxo-crown ethers and derivatives containing a-amino-acid residues, Reactive & Functional Polymers, 2008, 1297-1306, 68(9).
Qing, G. et al., Chiral Effect at Protein/Graphene Interface: A Bioinspired Perspective to Understand Amyloid Formation, Journal of the American Chemical Society, 2014, 10736-10742, 136(30).
Wang, B. et al., Amino acid endcapped poly(p-dioxanone): synthesis and crystallization, J Polym Res, 2013, 1-9, 20(4).
Zhang, J. et al., Synthesis and characterization of heterotelechelic poly(ethylene glycol)s with amino acid at one end and hydroxyl group at another end, Journal of Applied Polymer Science, 2008, 2432-2439, 110(4).
Ahamed, Tangir, Phase Behavior of an Intact Monoclonal Antibody, Biochemical Journal, 2007, 610-619, 93.
Altschul, Stephen F., A Protein Alignment Scoring System Sensitive at All Evolutionary Distances, J Mol Evol, 1993, 290-300, 36.
Armstrong, NA, Sucrose, Handbook of Pharmaceutical Excipients, 2009, 703-707, 6th Edition.
Banks et al., Removal of cysteinylation from an unpaired sulfhydryl in the variable region of a recombinant monoclonal IgG1 antibody improves homogeneity, stability, and biological activity, J Pharm Sci, 2008, 775-790, 97(2).

(56) References Cited

OTHER PUBLICATIONS

Banks, Douglas D. et al., The Effect of Sucrose Hydrolysis on the Stability of Protein Therapeutics during Accelerated Formulation Studies, J. Pharm. Sci., 2009, 4501-4510, 98(12).
Basu et al., Protein crystals for the delivery of biopharmaceuticals, Expert Opinion on Biological Therapy, 2004, pp. 301-317, vol. 4(3).
Benlysta prescribing information, Mar. 2011.
Bernstein, J., Bioavailability, Polymorphism of molecular crystals, 2007, 324-330 (translated pp. 1-9), Ch. 7.3.2.
Bernstein, J., Bioavailability, Polymorphism of molecular crystals, 2007, 324-330, Ch. 7.3.2.
Bhambhani, Akhilesh, Formulation Design and High-Throughput Excipient Selection Based on Structural Integrity and Conformational Stability of Dilute and Highly Concentrated IgG1 Monoclonal Antibody Solutions, Journal of Pharmaceutical Sciences, 2012, 1120-1135, vol. 101, No. 3.
Bowman, Edward P. et al., Rationale and safety of anti-interleukin-23 and anti-interleukin-17A therapy, Curr Opin Infect Dis, 2006, 245-252, 19(3).
Carpenter, John F. et al., Rational Design of Stable Lyophilized Protein Formulations: Some Practical Advice, Pharmaceutical Research, 1997, 969-975, 14(8).
Carpenter, John F., Application of infrared spectroscopy to development of stable lyophilized protein formations, European Journal of Pharmaceutics and Biopharmaceutics, 1998, 231-238, 45.
Chang, B.S. and Hershenson, S., Practical approaches to protein formulation development in "Rationale Design of stable protein formulations-theory and practice", Kluwer Academic/Plenum Publishers, 2002, 1-25, -.
Chauvin et al., TIGIT and PD-1 impair tumor antigen-specific CD8 T cells in melanoma patients, Journal of Clinical Investigation, 2015, pp. 2046-2058, vol. 125(5).
Chen, et al., Influence of histidine on the stability and physical properties of a fully human antibody in aqueous and solid forms, 2003, 1952-1960, 20(12), Pharm Res.
Cordoba et al., Non-enzymatic hinge region fragmentation of antibodies in solution, 2005, 115-121, 818(2), J Chromatogr B Analyt Technol Biomed Life Sci.
Costantino, Henry R., The Secondary Structure and Aggregation of Lyophilized Tetanus Toxoid, Journal of Pharmaceutical Sciences, 1996, 1290-1293, vol. 85, No. 12.
Cua, Daniel J. et al., TGF-beta, a 'double agent' in the immune pathology war, Nat. Immunol., 2006, 557-559, 7(6).
Cudney, R., Protein Crystallization and Dumb Luck, The Rigaku Journal, 1999, 1-7, vol. 16, No. 1.
Daugherty, Ann L. et al., Formulation and Delivery Issues for Monoclonal Antibody Therapeutics, Current Trends in Monoclonal Antibody Development and Manufacturing, 2010, 103-129, Chapter 8.
Davagnino, Juan et al., Acid hydrolysis of monoclonal antibodies, J. Immunol. Methods, 1995, 177-180, 185(2).
Davies et al., Structural Determinants of Unique Properties of Human IgG4-Fc, Journal of Molecular Biology, 2014, pp. 630-644, vol. 426(3).
Dayhoff, M.O., A Model of Evolutionary Change in Proteins, Atlas of Protein Sequence and Structure, 1978, 345-352, 22.
Dear et al., Contrasting the Influence of Cationic Amino Acids on the Viscosity and Stabililty of a Highly Concentrated Monoclonal Antibody, Pharm. Res., 2017, 193-207, vol. 34.
Dembo, Amir, Limit Distribution of Maximal Non-Aligned Two-Sequence Segmental Score, The Annals of Probability, 1994, 2022-2039, vol. 22, No. 4.
Dougall, W.C. et al., TIGIT and CD96: new checkpoint receptor targets for cancer immunotherapy, Immunological Reviews, 2017, 112-120, 276.
European Medicines Agency, European Public Assessment Report (EPAR) Avastin, Scientific Discussion. Jan. 24, 2006, pp. 1-61.
Falconer, Robert J. et al., Stabilization of a monoclonal antibody during purification and formulation by addition of basic amino acid excipients, J Chem Technol Biorechnol, 2011, 942-948, 86.

FDA label for Amjevita (Adalimumab), Sep. 2016, p. 1-61.
FDA label for Arzerra (Ofatumumab), Oct. 2009, p. 1-13.
FDA label for Avastin (Bevacizumab), Sep. 2011, p. 1-25.
FDA label for Bavencio (Avelumab), Mar. 2017, p. 1-20.
FDA label for Campath or Lemtrada (Alemtuzumab), Sep. 2014, p. 1-18.
FDA label for Cimzia (Certolizumab), Jan. 2017, p. 1-40.
FDA label for Drazalex (Daratumumab), Nov. 2016, p. 1-26.
FDA label for Humira (Adalimumab), Jan. 2008, p. 1-34.
FDA label for Kadcyla (Ado-Trastuzumab Emtansine), Aug. 29, 2013, p. 1-26.
FDA label for Mylotarg (Gemtuzumab Ozogamicin), Aug. 2005, p. 1-21.
FDA label for Opdivo (Nivolumab), Dec. 2017, p. 1-73.
FDA label for Praxbind (Idarucizumab), Oct. 2015, p. 1-10.
FDA label for Prolia (Denosumab), Sep. 2011, p. 1-20.
FDA label for Prostascint (Capromab Pendetide), Jun. 2012, p. 1-16.
FDA label for Protrazza (Necitumumab), Nov. 2015, p. '1-12.
FDA label for Raxibacumab, Dec. 2012, p. 1-14.
FDA label for Reopro (Abciximab), dated Nov. 4, 1997, p. 1-17.
FDA label for Repatha (Evolocumab), Aug. 2015, p. 1-34.
FDA label for Rituxan (Rituximab), Feb. 2010, p. 1-35.
FDA label for Simulect (Basiliximab), May 1998, p. 1-7.
FDA label for Soliris (Eculizumab), Sep. 2011, p. 1-24.
FDA label for Tysabri (Natalizumab), Jan. 2012, p. 1-32.
FDA label for Vectibix (Panitumumab), Jun. 2017, p. 1-31.
FDA label for Zevalin (Ibritumomab Tiuxetan), Sep. 2009, p. 1-11.
FDA label of Adcetris, Nov. 2014, pp. 1-19.
FDA label of Benlysta, Mar. 2012, pp. 1-22.
FDA label of Blincyto, Dec. 2014, pp. 1-24.
FDA label of Cinqair, Mar. 2016, pp. 1-16.
FDA label of Empliciti, Nov. 2015, pp. 1-22.
FDA label of Entyvio, May 2014, pp. 1-21.
FDA label of Erbitux, Jan. 2012, pp. 1-31.
FDA label of Fasenra, Nov. 2017, pp. 1-8.
FDA label of Haris, Mar. 2012, pp. 1-13.
FDA label of Kevzara, May 2017, pp. 1-45.
FDA label of Nucala, Nov. 2015, pp. 1-28.
FDA label of Ocrevus, Mar. 2017, pp. 1-18.
FDA label of Raptiva, Mar. 2009, pp. 1-36.
FDA label of Remicade, Feb. 2011, pp. 1-47.
FDA label of Siliq, Feb. 2017, pp. 1-22.
FDA label of Sylvant, 2014, pp. 1-16.
FDA label of Taltz Mar. 2016, pp. 1-25.
FDA label of Xolair, 2007, pp. 1-20.
FDA label of Yervoy, Oct. 2015, pp. 1-32.
FDA label of Zinbryta, May 2016, pp. 1-32.
FDA label of Zinplava, Oct. 2016, pp. 1-11.
Garber, Ellen et al., A broad range of Fab stabilities within a host of therapeutic IgGs, Biochemical and Biophysical Research Communications, 2007, 751-757, 355.
Ghosh et al., Natalizumab for active Crohns disease, New England J. Med., 2003, pp. 24-32, 348.
Giege, et al., Crystallogenesis of Biological Macromolecules: Facts and Perspectives, Acta Cryst., 1994, pp. 339-350, D50.
Gikanga, Benson et al., Manufacturing of High-Concentration Monoclonal Antibody Formulations via Spray Drying—the Road to Manufacturing Scale, PDS J Pharm Sci and Tech, 2015, 59-73, 69.
Gizzi, Patrick et al., Molecular Tailored Histidine-Based Complexing Surfactants: From Micelles to Hydrogels, Eur. J Org Chem., 2009, 3953-3963, N/A.
Guo, Zheng et al., Structure-Activity Relationship for Hydrophobic Salts as Viscosity-Lowering Excipients for Concentrated Solutions of Monoclonal Antibodies, Pharm Res, 2012, 3102-3109, 29.
Harris et al., Comparison of the conformations of two intact monoclonal antibodies with hinges, Immunological Reviews, 1998, pp. 35-43, vol. 163.
Harris et al., Crystallization of Intact Monoclonal Antibodies, Proteins: Structure, Function, and Genetics, 1995, pp. 285-289, vol. 23, No. 2.
Harris, Reed J. et al., Identification of multiple sources of charge heterogeneity in a recombinant antibody, Journal of Chromatography B, 2001, 233-245, 752(2).

(56) References Cited

OTHER PUBLICATIONS

He et al., Humanization and Pharmacokinetics of a Monoclonal Antibody with Specificity for both E- and P- Selectin, J. Immunol., 1998, pp. 1029-1035, 160.
International Search Report of the International Searching Authority for International Application No. PCT/US2013/073825, dated Feb. 7, 2014 (3 pages).
Ionescu, Roxana et al., Kinetics of Chemical Degradation in Monoclonal Antibodies: Relationship between Rates at the Molecular and Peptide Levels, Anal. Chem., 2010, 3198-3206, 82(8).
IR Application No. 139450140003010080 "Single-chain recombinant antibody against ErbB3 receptor effective in inhibiting breast cancer cell growth" (22 pages).
IR Application No. 139450140003010080 "Single-chain recombinant antibody against ErbB3 receptor effective in inhibiting breast cancer cell growth" (English translation, 12 pages).
Izutsu, Ken-Ichi et al., Excipient crystallinity and its protein-structure-stabilizing effect during freeze-drying, Journal of Pharmacy and Pharmacology, 2002, 1033-1039, 54.
Jezek, Jan et al., Viscosity of concentrated therapeutic protein compositions, Advanced Drug Delivery Reviews, 2011, 1107-1117, 63.
Kaithamana, Shashi, Induction of Experimental Autoimmune Graves' Disease in BALB/c Mice, The Journal of Immunology, 1999, 5157-5164, 163.
Kohler et al., Continuous Cultures of Fused Cells Secreting Antibody of Predefined Specificity, Nature, 1975, pp. 195-497, vol. 256.
Kundrot, C.E., Which strategy for a protein crystallization project?, Cellular Molecular Life Science, 2004, 525-536, 61.
Lam, Xanthe M. et al., Antioxidants for Prevention of Methionine Oxidation in Recombinant Monoclonal Antibody HER2, J Pharm Sci., 1997, 1250-1255, 86(11).
Langrish, Claire L. et al., IL-12 and IL-23: master regulators of innate and adaptive immunity, Immunol. Rev., 2004, 96-105, 202.
Le Doussal et al., Enhanced in vivo targeting of an asymmetric bivalent hapten to double-antigen-positive mouse B cells with monoclonal antibody conjugate cocktails, J. Immunol, 1991, pp. 169-175, 146.
Liu, Hongcheng et al., Heterogeneity of Monoclonal Antibodies, J. Pharm. Sci., 2008, 2426-2447, 97(7).
Liu, Jun et al., Reversible Self-Association Increases the Viscosity of a Concentrated Monoclonal Antibody in Aqueous Solution, Journal of Pharmaceutical Sciences, 2005, 1928-1940, 94(9).
Liu, Y. Diana et al., Human IgG2 Antibody Disulfide Rearrangement in Vivo, J. Biol. Chem., 2008, 29266-29272, 283(43).
Mach, Henryk et al., Addressing new analytical challenges in protein formulation development, European Journal of Pharmaceutics and Biopharmaceutics, 2011, 196-207, 78.
McCoy et al., Phaser crystallographic software, Journal of Applied Crystallography, 2007, pp. 658-674, vol. 40.
McDermott, et al., PD-1 as a potential target in cancer therapy, Cancer Medicine, 2013, pp. 662-673, WO.
Menne, Kerstin M.L., A comparison of signal sequence prediction methods using a test set of signal peptides, Bioinformatics Applications Note, 2000, 741-742, 16.
Milgrom et al., Treatment of allergic asthma with monoclonal anti IgE antibody, New England Journal Med., 1999, pp. 1966-1973, 341.
Morissette, Sherry L. et al., High-throughput crystallization: polymorphs, salts, co-crystals and solvates of pharmaceutical solids, Advanced Drug Delivery Reviews, 2004, 275-300, 56.
Murakami, Monica S., Cell Cycle Regulation, Oncogenes, and Antineoplastic Drugs, The Molecular Basis of Cancer, 1995, 3-17, Chapter 1.
Ollmann Saphire et al., Crystal Structure of a Neutralizing Human IgG Against HIV-1: A Template for Vaccine Design, Science, 2001, pp. 1155-1159, vol. 293.
Perchiacca, Joseph M. et al., Aggregation-resistant domain antibodies engineered with charged mutations near the edges of the complementarity-determining regions, Protein Engineering, Design & Selection, 2012, 591-601, 25(10).
Poole, Raewyn M., Pembrolizumab: First Global Approval, Drugs, 2014, 1973-1981, 74(16).
Prestrelski, Steven J., Optimization of Lyophilization Conditions for Recombinant Human Interleukin-2 by Dried State Conformational Analysis Using Fourier-Transform Infrared Spectroscopy, Pharmaceutical Research, 1995, 1250-1259, vol. 12, No. 9.
Prolia prescribing information, Jun. 2010.
Reich, Gabriele. Chapter 10: "Pharmaceutical Formulation and Clinical Application". D19 is a chapter from the textbook "Handbook of Therapeutic Antibodies, vol. 1", published by Wiley & Sons in 2007.
Reichert, et al., Monoclonal antibody successes in the clinic, Nature Biotechnology, 2005, pp. 1073-1078, vol. 23.
Reissner, K. J. et al., Deamidation and isoaspartate formation in proteins: unwanted alterations or surreptitious signals?, Cell. Mol. Life Sci., 2003, 1281-1295, 60.
Remmele, Richard L., Interleukin-1 Receptor (IL-1R) Liquid Formulation Development Using Differential Scanning Calorimetry, Pharmaceutical Research, 1998, 200-208, vol. 15, No. 2.
Rustandi, Richard R. et al., Applications of CE SDS gel in development of biopharmaceutical-antibody-based products, Electrophoresis, 2008, 3612-3620, 29(17).
Sane, Samir U. et al., Raman Spectroscopic Characterization of Drying-Induced Structural Changes in a Therapeutic Antibody: Correlating Structural Changes with Long-Term Stability, Journal of Pharmaceutical Sciences, 2004, 1005-1018, 93(4).
Scapin et al., Structure of full-length human anti-PD1 therapeutic IgG4 antibody pembrolizumab, Nature Structural & Molecular Biology, 2015, pp. 953-958, vol. 22, No. 12.
Schermeyer, Marie-Therese et al., Characterization of highly concentrated antibody solution—A toolbox for the description of protein long-term solution stability, MABS, 2017, 1169-1185, 9(7).
Seifert, Tina et al., Chroman-4-one- and Chromone-Based Sirtuin 2 Inhibitors with Antiproliferative Properties in Cancer Cells, Journal of Medicinal Chemistry, 2014, 9870-9888, 57.
Shahrokh, Zahra, Approaches to Analysis of Aggregates and Demonstrating Mass Balance in Pharmaceutical Protein (Basic Fibroblast Growth Factor) Formulations, Journal of Pharmaceutical Sciences, 1994, 1645-1650, vol. 83, No. 12.
Sharma et al., Preparation, purification and crystallization of antibody Fabs and single-chain Fv domains, Immunology Methods Manual: The Comprehensive Sourcebook of Techniques, 1997, pp. 15-37, vol. 1.
Shire, Steven J., et al., Formulation and manufacturing of biologies, Current Opinion in Biotechnology, 2009, 708-714, 20.
Shire, Steven J., et al., Challenges in the Development of High Protein Concentration Formulations, Journal of Pharmaceutical Sciences, 2004, 1390-1402, 93(6).
Sigma-Aldrich, Co., Products for Life Science Research, 2001, 1-47, N/A.
Slamon et al., Use of chemotherapy plus a monoclonal antibody against HER2 for metastatic breast cancer that overexpresses HER2, New England J. Med., 2001, pp. 783-792, 344.
Sluzky, Victoria, Chomatographic Methods for Quantitative Analysis of Native, Denatured, and Aggregated Basic Fibroblast Growth Factor in Solution Formulations, Pharmaceutical Research, 1994, 485-490, vol. 11, No. 4.
Study NCT01295827 posted in Feb. 2011 on ClinicalTrials.gov (see p. 6 "First Posted"), 14 pages.
Sumit Goswami, Developments and Challenges for mAb-based Therapeutics, Antibodies, 2013, 452-500, 2.
Sworn statement of Chakravarthy Nachu Narasimhan, 2 pages.
Te Booy, Marcel, Evaluation of the Physical Stability of Freeze-Dried Sucrose-Containing Formulations by Differential Scanning Calorimetry, Pharmaceutical Research, 1992, 109-114, vol. 9, No. 1.
Tomar, Dheeraj S., Molecular basis of high viscosity in concentrated antibody solutions: Strategies for high concentration drug product development, mAbs, 2016, 216-228, vol. 8, No. 2.
Tysabri prescribing information, Nov. 2004.
Uchiyama, Susumu, Liquid formulation for antibody drugs, Biochimica et Biophysica Acta, 2014, 2041-2052, 1844.

(56) References Cited

OTHER PUBLICATIONS

Usami, A., The effect of pH, hydrogen peroxide and temperature on the stability of human monoclonal antibody, Journal of Pharmaceutical and Biomedical Analysis, 1996, 1133-1140, 14.
Vermeer, Arnoldus W. P. et al., The Thermal Stability of Immunoglobulin: Unfolding and Aggregation of a Multi-Domain Protein, Biophysical Journal, 2000, 394-404, 78(1).
Vlasak, Josef et al., Fragmentation of monoclonal antibodies, MABS, 2011, 253-263, 3(3).
Vlasak, Josef et al., Identification and characterization of asparagine deamidation in the light chain CDR1 of a humanized IgG1 antibody, Anal. Biochem., 2009, 145-154, 392(2).
Von Heijne et al., A new method for predicting signal sequence cleavage sites, Nucleic Acids Res., 1986, pp. 1683-4690, 14.
Walily, EL, Simultaneous determination of tenoxicam and 2-aminopyridine using derivative spectrophotometry and high-performance liquid chromatography, Journal of Pharmaceutical and Biomedical Analysis, 1997, 1923-1928, 15.
Wang, Shujing et al., Viscosity-Lowering Effect of Amino Acids and Salts on Highly Concentrated Solutions of Two IgG1 Monoclonal Antibodies, Mol. Pharmaceutics, 2015, 4478-4487, 12.
Warne, Nicholas W., Formulation Development of Phase 1-2 Biopharmaceuticals: An Efficient and Timely Approach, John Wiley & Sons, Inc., 2010, 147-159, Chapter 6.
Weber, Patricia C., Overview of Protein Crystallization Methods, Methods in Enzymology, 1997, 13-22, 276.
Webster, Simon, Predicting Long-Term Storage Stability of Therapeutic Proteins, Pharmaceutical Technology, 2013, 1-7, 37(11).
Wei, Ziping et al., Identification of a Single Tryptophan Residue as Critical for Binding Activity in a Humanized Monoclonal Antibody against Respiratory Syncytial Virus, Anal. Chem., 2007, 2797-2805, 79(7).
Wiekowski, Maria T. et al., Ubiquitous Transgenic Expression of the IL-23 Subunit p19 Induces Multiorgan Inflammation, Runting, Infertility, and Premature Death, J. Immunol., 2001, 7563-7570, 166(12).
Yang, M. et al., Crystalline monoclonal antibodies for subcutaneous delivery, Proceedings of the the National Academy of Sciences, Jun. 10, 2003, 6934-6939, 100-12.
Yu, Lei et al., Investigation of N-terminal glutamate cyclization of recombinant monoclonal antibody in formulation development, J. Pharm Biomed. Anal., 2006, 455-463, 42(4).
Zang, Yuguo, Towards Protein Crystallization as a Process Step in Downstream Processing of Therapeutic Antibodies: Screening and Optimization at Microbatch Scale, PLoS ONE, 2011, 1-8, 6(9).
Brahmer et al., Safety and Activity of Anti-PD-L1 Antibody in Patients with Advanced Cancer, The New England Journal of Medicine, 2012, pp. 2455-2465, vol. 366, No. 26.
D. M. Pardoll, The blockade of immune checkpoints in cancer immunotherapy, Nature Reviews/Cancer, 2012, pp. 252-264, vol. 12.
Daugherty et al., Formulation and delivery issues for monoclonal antibody therapeutics, Advanced Drug Delivery Reviews, 2006, pp. 686-706, vol. 58, No. 5-6.
European Search Report, European Search Report, European Search Report, dated Nov. 5, 2014, 6, 6 pages.
Fukuda, Masakazu et al., Thermodynamic and Fluorescence Analyses to Determine Mechanisms of IgG1 Stabilization and Destabilization by Arginine, Pharm. Res., 2014, 992-1001, 31.
Garon et al., Pembrolizumab for the Treatment of Non-Small-Cell Lung Cancer, The New England Journal of Medicine, 2015, pp. 2018-2028, vol. 372, No. 21.
Hamid et al. , Safety and Tumor Responses with Lambrolizumab (Anti-PD-1) in Melanoma, New Eng. J. Med., 2013, 134-144, 369(2).
Herold, ANTI-CD3 Monoclonal Antibody in New-Onset Type 1 Diabetes Mellitus, New England Journal of Medicine, 2002, pp. 1692-1698, 346.
International Search Report, International Application PCT/US12/31063, dated Jun. 22, 2012.
Jones, Andrew U.S., Analysis of Polypeptides and proteins, Advanced Drug Delivery Reviews, 1993, 29-90, 10.
Keytruda (Merck & Co., Inc., Whitehouse Station, NJ USA; initial U.S. approval 2014, updated Sep. 2017) 49 pages.
Kheddo, Priscilla et al., The effect of arginine glutamate on the stability of monoclonal antibodies in solution, Int. J. Pharmaceutics, 2014, 126-133, 473.
Liu et al., Randomised, double blind, placebo controlled study of interferon b-1a in relapsing-remitting multiple sclerosis analysed by area under disability/time curves, N. Neurol. Neurosurg. Psych., 1999, pp. 451-456, 67.
Merck Sharp & Dohme Corp., Study of Pembrolizumab (MK-3475) in participants with progressive locally advanced or metastatic carcinoma, melanoma, or non-small cell lung carcinoma (P07990/MK-3475-001/Keynote-001), Clinicaltrials.gov, 2015, 1-12, 1.
Pearlman, Rodney, Analysis of Protein Drugs, Peptide and Protein Drug Delivery, 1991, 247-301, Chapter 6.
Portielje, IL-12: a promising adjuvant for cancer vaccination, Cancer Immunol Immunother, 2003, 133-144, 52.
Presta, Leonard G. et al., Selection, design, and engineering of therapeutic antibodies, J. Allergy Clin. Immunol., 2005, 731-736, 116(4).
Presta, Leonard G., Engineering of therapeutic antibodies to minimize immunogenicity and optimize function, Advanced Drug Delivery Reviews, 2006, 640-656, 58.
Robert et al., Anti-programmed-death-receptor-1 treatment with pembrolizumab in ipilimumab-refractory advanced melanoma: a randomised dose-comparison cohort of a phase 1 trial, The Lancet, 2014, pp. 1109-1117, vol. 384.
Robert et al., Nivolumab in Previously Untreated Melanoma without BRAF Mutation, The New England Journal of Medicine, 2015, pp. 320-330, vol. 372, No. 4.
Robert et al., Pembrolizumab versus Ipilimumab in Advanced Melanoma, The New England Journal of Medicine, Jun. 25, 2015, pp. 2521-2532, 372.
Topalian et al., Safety, Activity, and Immune Correlates of Anti-PD-1 Antibody in Cancer, New Eng. J. Med., 2012, 2443-2454, 366(26).
Topalian et al., Survival, Durable Tumor Remission, and Long-Term Safety in Patients With Advanced Melanoma Receiving Nivolumab, Clinical Journal of Oncology, 2014, pp. 1020-1030, vol. 32, No. 10.
Wang et al., Antibody structure, instability, and formulation, J. Pharm. Sci., 2007, 1-26, 96(1).
Wang, Instability, stabilization, and formulation of liquid protein pharmaceuticals, Int J Pharm, 1999, pp. 129-188, vol. 185, No. 2.
Warne, Development of high concentration protein biopharmaceuticals: the use of platform approaches in formulation development, 2011, 208-212, 78(2), Eur J Pharm Biopharm.
WHO Drug Information, vol. 27, No. 2, pp. 161-162 (2013).
Wolchok et al., Nivolumab plus Ipilimumab in Advanced Melanoma, The New England Journal of Medicine, 2013, pp. 122-133, vol. 369(2).
Written Opinion, International Application No. PCT/US12/31063, dated Jun. 22, 2012.
Yang et al., A Randomized Trial of Bevacizumab, an Anti-Vascular Endothelial Growth Factor Antibody, for Metastatic Renal Cancer, New England Journal of Medicine, 2003, pp. 427-434, 349.
Zhou, Shuxia et al., Biotherapeutic Formulation Factors Affecting Metal Leachables from Stainless Steel Studied by Design of Experiments, AAPS PharmSciTech, 2012, 284-294, 13(1).
Accession No. 2013:400660 (Year: 2013), 1 page.
Accession No. 2017:1215621 (Year: 2017), 2 pages.
Chauhan, Veeren M., Advancements in the co-formulation of biologic therapeutics, Journal of Controlled Release, 2020, pp. 397-405, vol. 327.
Larkin et al., Combined Nivolumab and Ipilmumab or Monotherapy in Untreated Melanoma, The New England Journal of Medicine, Jul. 2, 2015, pp. 23-34, 373.
Mukherjee, Sreya, Crystal Engineering of Pharmaceutical Cocrystals, University of South Florida, 2011, 1-144, N/A.
Reichert, Paul et al., Pembrolizumab microgravity crystallization experimentation, npj Microgravity, 2019, 1-8, 5.

(56) References Cited

OTHER PUBLICATIONS

Sikalidis, Angelos K., Amino Acids and Immune Response: A Role for Cysteine, Glutamine, Phenylalanine, Tryptophan and Arginine in T-cell Function and Cancer?, Pathol. Oncol. Res, 2015, 9-17, 21.

Tyagi, R. et al., The use of chemical modification and chemical crosslinking to stabilize proteins (enzymes), Biochemistry, 1998, 395-407, 63(3).

Yakubke, H.D. et al., Amino acids, peptides, proteins, M: Mir, 1985, 91-94, N/A.

Yu, Lian, Amorphous pharmaceutical solids: preparation, characterization and stabilization, Advanced Drug Delivery Reviews, 2001, 27-42, 48.

Introduction to the textbook which contains D16, Nicholas W. Warne, 2010.

Jorgensen, Lene et al., Recent trends in stabilising peptides and proteins in pharmaceutical formulation—considerations in the choice of excipients, Expert Opinion on Drug Delivery, 2009, 1219-1230, 6(11).

Krishnan, Development of Formulations for Therapeutic Monoclonal Antibodies and Fc Fusion Proteins, Chugai Exhibit 2014, 2010, pp. 1-48.

Liu, Dingjiang et al., Structure and Stability Changes of Human IgG1 Fc as a Consequence of Methionine Oxidation, Biochemistry, 2008, 5088-5100, 47(18).

\* cited by examiner
† cited by third party

SEQUENCE LISTING

<160> NUMBER OF SEQ ID NOS: 34

<210> SEQ ID NO 1
<211> LENGTH: 15
<212> TYPE: PRT
<213> ORGANISM: Artificial sequence
<220> FEATURE:
<223> OTHER INFORMATION: Pembrolizumab-Light chain CDR1

<400> SEQUENCE: 1

```
Arg Ala Ser Lys Gly Val Ser Thr Ser Gly Tyr Ser Tyr Leu His
1               5                   10                  15

<210> SEQ ID NO 2
<211> LENGTH: 7
<212> TYPE: PRT
<213> ORGANISM: Artificial Sequence
<220> FEATURE:
<223> OTHER INFORMATION: Pembrolizumab-Light chain CDR2

<400> SEQUENCE: 2

Leu Ala Ser Tyr Leu Glu Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Pembrolizumab-Light chain CDR3

<400> SEQUENCE: 3

Gln His Ser Arg Asp Leu Pro Leu Thr
1               5

<210> SEQ ID NO 4
<211> LENGTH: 111
<212> TYPE: PRT
<213> ORGANISM: Artificial Sequence
<220> FEATURE:
<223> OTHER INFORMATION: Pembrolizumab-Light chain variable region

<400> SEQUENCE: 4

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
                20                  25                  30

Gly Tyr Ser Tyr Leu His Trp Tyr Gln Gln Lys Pro Gly Gln Ala Pro
            35                  40                  45

Arg Leu Leu Ile Tyr Leu Ala Ser Tyr Leu Glu Ser Gly Val Pro Ala
        50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys
            100                 105                 110

<210> SEQ ID NO 5
<211> LENGTH: 218
<212> TYPE: PRT
<213> ORGANISM: Artificial Sequence
<220> FEATURE:
<223> OTHER INFORMATION: Pembrolizumab-Light chain

<400> SEQUENCE: 5

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
                20                  25                  30

Gly Tyr Ser Tyr Leu His Trp Tyr Gln Gln Lys Pro Gly Gln Ala Pro
            35                  40                  45
```

```
Arg Leu Leu Ile Tyr Leu Ala Ser Tyr Leu Glu Ser Gly Val Pro Ala
     50                  55                  60

Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Tyr Cys Gln His Ser Arg
                 85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 6
<211> LENGTH: 5
<212> TYPE: PRT
<213> ORGANISM: Artificial Sequence
<220> FEATURE:
<223> OTHER INFORMATION: Pembrolizumab-Heavy chain CDR1

<400> SEQUENCE: 6

Asn Tyr Tyr Met Tyr
1               5

<210> SEQ ID NO 7
<211> LENGTH: 17
<212> TYPE: PRT
<213> ORGANISM: Artificial sequence
<220> FEATURE:
<223> OTHER INFORMATION: Pembrolizumab-Heavy chain CDR2

<400> SEQUENCE: 7

Gly Ile Asn Pro Ser Asn Gly Gly Thr Asn Phe Asn Glu Lys Phe Lys
1               5                   10                  15

Asn

<210> SEQ ID NO 8
<211> LENGTH: 11
<212> TYPE: PRT
<213> ORGANISM: Artificial sequence
<220> FEATURE:
<223> OTHER INFORMATION: Pembrolizumab-Heavy chain CDR3

<400> SEQUENCE: 8

Arg Asp Tyr Arg Phe Asp Met Gly Phe Asp Tyr
1               5                   10

<210> SEQ ID NO 9
<211> LENGTH: 120
<212> TYPE: PRT
```

```
<213> ORGANISM: Artificial sequence
<220> FEATURE:
<223> OTHER INFORMATION: Pembrolizumab-Heavy chain variable region

<400> SEQUENCE: 9
```

| | | | | | | | | | | | | | | |
|---|---|---|---|---|---|---|---|---|---|---|---|---|---|---|
| Gln | Val | Gln | Leu | Val | Gln | Ser | Gly | Val | Glu | Val | Lys | Lys | Pro | Gly | Ala |
| 1 | | | | 5 | | | | | 10 | | | | | 15 | |

| Ser | Val | Lys | Val | Ser | Cys | Lys | Ala | Ser | Gly | Tyr | Thr | Phe | Thr | Asn | Tyr |
|---|---|---|---|---|---|---|---|---|---|---|---|---|---|---|---|
| | | | 20 | | | | | 25 | | | | | 30 | | |

| Tyr | Met | Tyr | Trp | Val | Arg | Gln | Ala | Pro | Gly | Gln | Gly | Leu | Glu | Trp | Met |
|---|---|---|---|---|---|---|---|---|---|---|---|---|---|---|---|
| | | 35 | | | | | 40 | | | | | 45 | | | |

| Gly | Gly | Ile | Asn | Pro | Ser | Asn | Gly | Gly | Thr | Asn | Phe | Asn | Glu | Lys | Phe |
|---|---|---|---|---|---|---|---|---|---|---|---|---|---|---|---|
| 50 | | | | | 55 | | | | | 60 | | | | | |

| Lys | Asn | Arg | Val | Thr | Leu | Thr | Thr | Asp | Ser | Ser | Thr | Thr | Thr | Ala | Tyr |
|---|---|---|---|---|---|---|---|---|---|---|---|---|---|---|---|
| 65 | | | | | 70 | | | | | 75 | | | | | 80 |

| Met | Glu | Leu | Lys | Ser | Leu | Gln | Phe | Asp | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Arg | Arg | Asp | Tyr | Arg | Phe | Asp | Met | Gly | Phe | Asp | Tyr | Trp | Gly | Gln |
|---|---|---|---|---|---|---|---|---|---|---|---|---|---|---|---|
| | | | 100 | | | | | 105 | | | | | 110 | | |

| Gly | Thr | Thr | Val | Thr | Val | Ser | Ser |
|---|---|---|---|---|---|---|---|
| | | 115 | | | | | 120 |

```
<210> SEQ ID NO 10
<211> LENGTH: 447
<212> TYPE: PRT
<213> ORGANISM: Artificial sequence
<220> FEATURE:
<223> OTHER INFORMATION: Pembrolizumab-Heavy chain

<400> SEQUENCE: 10
```

| Gln | Val | Gln | Leu | Val | Gln | Ser | Gly | Val | Glu | Val | Lys | Lys | Pro | Gly | Ala |
|---|---|---|---|---|---|---|---|---|---|---|---|---|---|---|---|
| 1 | | | | 5 | | | | | 10 | | | | | 15 | |

| Ser | Val | Lys | Val | Ser | Cys | Lys | Ala | Ser | Gly | Tyr | Thr | Phe | Thr | Asn | Tyr |
|---|---|---|---|---|---|---|---|---|---|---|---|---|---|---|---|
| | | | 20 | | | | | 25 | | | | | 30 | | |

| Tyr | Met | Tyr | Trp | Val | Arg | Gln | Ala | Pro | Gly | Gln | Gly | Leu | Glu | Trp | Met |
|---|---|---|---|---|---|---|---|---|---|---|---|---|---|---|---|
| | | 35 | | | | | 40 | | | | | 45 | | | |

| Gly | Gly | Ile | Asn | Pro | Ser | Asn | Gly | Gly | Thr | Asn | Phe | Asn | Glu | Lys | Phe |
|---|---|---|---|---|---|---|---|---|---|---|---|---|---|---|---|
| 50 | | | | | 55 | | | | | 60 | | | | | |

| Lys | Asn | Arg | Val | Thr | Leu | Thr | Thr | Asp | Ser | Ser | Thr | Thr | Thr | Ala | Tyr |
|---|---|---|---|---|---|---|---|---|---|---|---|---|---|---|---|
| 65 | | | | | 70 | | | | | 75 | | | | | 80 |

| Met | Glu | Leu | Lys | Ser | Leu | Gln | Phe | Asp | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Arg | Arg | Asp | Tyr | Arg | Phe | Asp | Met | Gly | Phe | Asp | Tyr | Trp | Gly | Gln |
|---|---|---|---|---|---|---|---|---|---|---|---|---|---|---|---|
| | | | 100 | | | | | 105 | | | | | 110 | | |

| Gly | Thr | Thr | Val | Thr | Val | Ser | Ser | Ala | Ser | Thr | Lys | Gly | Pro | Ser | Val |
|---|---|---|---|---|---|---|---|---|---|---|---|---|---|---|---|
| | | 115 | | | | | 120 | | | | | 125 | | | |

| Phe | Pro | Leu | Ala | Pro | Cys | Ser | Arg | Ser | Thr | Ser | Glu | Ser | Thr | Ala | Ala |
|---|---|---|---|---|---|---|---|---|---|---|---|---|---|---|---|
| | 130 | | | | | 135 | | | | | 140 | | | | |

| Leu | Gly | Cys | Leu | Val | Lys | Asp | Tyr | Phe | Pro | Glu | Pro | Val | Thr | Val | Ser |
|---|---|---|---|---|---|---|---|---|---|---|---|---|---|---|---|
| 145 | | | | | 150 | | | | | 155 | | | | | 160 |

| Trp | Asn | Ser | Gly | Ala | Leu | Thr | Ser | Gly | Val | His | Thr | Phe | Pro | Ala | Val |
|---|---|---|---|---|---|---|---|---|---|---|---|---|---|---|---|
| | | | | 165 | | | | | 170 | | | | | 175 | |

| Leu | Gln | Ser | Ser | Gly | Leu | Tyr | Ser | Leu | Ser | Val | Val | Thr | Val | Pro |
|---|---|---|---|---|---|---|---|---|---|---|---|---|---|---|
| | | | 180 | | | | | 185 | | | | | 190 | |

| Ser | Ser | Ser | Leu | Gly | Thr | Lys | Thr | Tyr | Thr | Cys | Asn | Val | Asp | His | Lys |
|---|---|---|---|---|---|---|---|---|---|---|---|---|---|---|---|
| | | | 195 | | | | | 200 | | | | | 205 | | |

```
Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
                275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Lys
                435                 440                 445

<210> SEQ ID NO 11
<211> LENGTH: 11
<212> TYPE: PRT
<213> ORGANISM: Homo sapiens

<400> SEQUENCE: 11

Arg Ala Ser Gln Ser Val Ser Ser Tyr Leu Ala
1               5                   10

<210> SEQ ID NO 12
<211> LENGTH: 7
<212> TYPE: PRT
<213> ORGANISM: Homo sapiens

<400> SEQUENCE: 12

Asp Ala Ser Asn Arg Ala Thr
1               5

<210> SEQ ID NO 13
<211> LENGTH: 9
<212> TYPE: PRT
<213> ORGANISM: Homo sapiens

<400> SEQUENCE: 13

Gln Gln Ser Ser Asn Trp Pro Arg Thr
1               5
```

```
<210> SEQ ID NO 14
<211> LENGTH: 107
<212> TYPE: PRT
<213> ORGANISM: Homo sapiens

<400> SEQUENCE: 14

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys
            100                 105

<210> SEQ ID NO 15
<211> LENGTH: 214
<212> TYPE: PRT
<213> ORGANISM: Homo sapiens

<400> SEQUENCE: 15

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 16
<211> LENGTH: 5
<212> TYPE: PRT
<213> ORGANISM: Homo sapiens

<400> SEQUENCE: 16

Asn Ser Gly Met His
1               5

<210> SEQ ID NO 17
<211> LENGTH: 17
<212> TYPE: PRT
<213> ORGANISM: Homo sapiens

<400> SEQUENCE: 17

Val Ile Trp Tyr Asp Gly Ser Lys Arg Tyr Tyr Ala Asp Ser Val Lys
1               5                   10                  15

Gly

<210> SEQ ID NO 18
<211> LENGTH: 4
<212> TYPE: PRT
<213> ORGANISM: Homo sapiens

<400> SEQUENCE: 18

Asn Asp Asp Tyr
1

<210> SEQ ID NO 19
<211> LENGTH: 113
<212> TYPE: PRT
<213> ORGANISM: Homo sapiens

<400> SEQUENCE: 19

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser

<210> SEQ ID NO 20
<211> LENGTH: 440
<212> TYPE: PRT
<213> ORGANISM: Homo sapiens

<400> SEQUENCE: 20

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30
```

```
Gly Met His Trp Val Arg Gln Ala Pro Gly Lys Gly Leu Glu Trp Val
         35                  40                  45
Ala Val Ile Trp Tyr Asp Gly Ser Lys Arg Tyr Ala Asp Ser Val
 50                  55                  60
Lys Gly Arg Phe Thr Ile Ser Arg Asp Asn Ser Lys Asn Thr Leu Phe
 65                  70                  75                  80
Leu Gln Met Asn Ser Leu Arg Ala Glu Asp Thr Ala Val Tyr Tyr Cys
                 85                  90                  95
Ala Thr Asn Asp Asp Tyr Trp Gly Gln Gly Thr Leu Val Thr Val Ser
            100                 105                 110
Ser Ala Ser Thr Lys Gly Pro Ser Val Phe Pro Leu Ala Pro Cys Ser
        115                 120                 125
Arg Ser Thr Ser Glu Ser Thr Ala Ala Leu Gly Cys Leu Val Lys Asp
130                 135                 140
Tyr Phe Pro Glu Pro Val Thr Val Ser Trp Asn Ser Gly Ala Leu Thr
145                 150                 155                 160
Ser Gly Val His Thr Phe Pro Ala Val Leu Gln Ser Ser Gly Leu Tyr
                165                 170                 175
Ser Leu Ser Ser Val Val Thr Val Pro Ser Ser Ser Leu Gly Thr Lys
            180                 185                 190
Thr Tyr Thr Cys Asn Val Asp His Lys Pro Ser Asn Thr Lys Val Asp
        195                 200                 205
Lys Arg Val Glu Ser Lys Tyr Gly Pro Pro Cys Pro Pro Cys Pro Ala
210                 215                 220
Pro Glu Phe Leu Gly Gly Pro Ser Val Phe Leu Phe Pro Pro Lys Pro
225                 230                 235                 240
Lys Asp Thr Leu Met Ile Ser Arg Thr Pro Glu Val Thr Cys Val Val
                245                 250                 255
Val Asp Val Ser Gln Glu Asp Pro Glu Val Gln Phe Asn Trp Tyr Val
            260                 265                 270
Asp Gly Val Glu Val His Asn Ala Lys Thr Lys Pro Arg Glu Glu Gln
        275                 280                 285
Phe Asn Ser Thr Tyr Arg Val Val Ser Val Leu Thr Val Leu His Gln
290                 295                 300
Asp Trp Leu Asn Gly Lys Glu Tyr Lys Cys Lys Val Ser Asn Lys Gly
305                 310                 315                 320
Leu Pro Ser Ser Ile Glu Lys Thr Ile Ser Lys Ala Lys Gly Gln Pro
                325                 330                 335
Arg Glu Pro Gln Val Tyr Thr Leu Pro Pro Ser Gln Glu Glu Met Thr
            340                 345                 350
Lys Asn Gln Val Ser Leu Thr Cys Leu Val Lys Gly Phe Tyr Pro Ser
        355                 360                 365
Asp Ile Ala Val Glu Trp Glu Ser Asn Gly Gln Pro Glu Asn Asn Tyr
370                 375                 380
Lys Thr Thr Pro Pro Val Leu Asp Ser Asp Gly Ser Phe Phe Leu Tyr
385                 390                 395                 400
Ser Arg Leu Thr Val Asp Lys Ser Arg Trp Gln Glu Gly Asn Val Phe
                405                 410                 415
Ser Cys Ser Val Met His Glu Ala Leu His Asn His Tyr Thr Gln Lys
            420                 425                 430
Ser Leu Ser Leu Ser Leu Gly Lys
        435                 440
```

```
<210> SEQ ID NO 21
<211> LENGTH: 15
<212> TYPE: PRT
<213> ORGANISM: Artificial sequence
<220> FEATURE:
<223> OTHER INFORMATION: hPD-1.08A Light Chain CDR1

<400> SEQUENCE: 21

Arg Ala Ser Lys Ser Val Ser Thr Ser Gly Phe Ser Tyr Leu His
1               5                   10                  15

<210> SEQ ID NO 22
<211> LENGTH: 7
<212> TYPE: PRT
<213> ORGANISM: Artificial sequence
<220> FEATURE:
<223> OTHER INFORMATION: hPD-1.08A Light Chain CDR2

<400> SEQUENCE: 22

Leu Ala Ser Asn Leu Glu Ser
1               5

<210> SEQ ID NO 23
<211> LENGTH: 9
<212> TYPE: PRT
<213> ORGANISM: Artificial sequence
<220> FEATURE:
<223> OTHER INFORMATION: hPD-1.08A Light Chain CDR3

<400> SEQUENCE: 23

Gln His Ser Trp Glu Leu Pro Leu Thr
1               5

<210> SEQ ID NO 24
<211> LENGTH: 5
<212> TYPE: PRT
<213> ORGANISM: Artificial sequence
<220> FEATURE:
<223> OTHER INFORMATION: hPD-1.08A Heavy Chain CDR1

<400> SEQUENCE: 24

Ser Tyr Tyr Leu Tyr
1               5

<210> SEQ ID NO 25
<211> LENGTH: 17
<212> TYPE: PRT
<213> ORGANISM: Artificial sequence
<220> FEATURE:
<223> OTHER INFORMATION: hPD-1.08A Heavy Chain CDR2

<400> SEQUENCE: 25

Gly Val Asn Pro Ser Asn Gly Gly Thr Asn Phe Ser Glu Lys Phe Lys
1               5                   10                  15

Ser

<210> SEQ ID NO 26
<211> LENGTH: 11
<212> TYPE: PRT
<213> ORGANISM: Artificial sequence
<220> FEATURE:
<223> OTHER INFORMATION: hPD-1.08A Heavy Chain CDR3

<400> SEQUENCE: 26

Arg Asp Ser Asn Tyr Asp Gly Gly Phe Asp Tyr
1               5                   10
```

<210> SEQ ID NO 27
<211> LENGTH: 120
<212> TYPE: PRT
<213> ORGANISM: Artificial sequence
<220> FEATURE:
<223> OTHER INFORMATION: h109A heavy chain variable region

<400> SEQUENCE: 27

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser
        115                 120

<210> SEQ ID NO 28
<211> LENGTH: 111
<212> TYPE: PRT
<213> ORGANISM: Artificial sequence
<220> FEATURE:
<223> OTHER INFORMATION: K09A light chain variable region

<400> SEQUENCE: 28

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys
            100                 105                 110

<210> SEQ ID NO 29
<211> LENGTH: 111
<212> TYPE: PRT
<213> ORGANISM: Artificial sequence
<220> FEATURE:
<223> OTHER INFORMATION: K09A light chain variable region

<400> SEQUENCE: 29

Glu Ile Val Leu Thr Gln Ser Pro Leu Ser Leu Pro Val Thr Pro Gly
1               5                   10                  15

Glu Pro Ala Ser Ile Ser Cys Arg Ala Ser Lys Gly Val Ser Thr Ser

```
                     20                  25                  30

Gly Tyr Ser Tyr Leu His Trp Tyr Leu Gln Lys Pro Gly Gln Ser Pro
                 35                  40                  45

Gln Leu Leu Ile Tyr Leu Ala Ser Tyr Leu Glu Ser Gly Val Pro Asp
             50                  55                  60

Arg Phe Ser Gly Ser Gly Ser Gly Thr Asp Phe Thr Leu Lys Ile Ser
 65                  70                  75                  80

Arg Val Glu Ala Glu Asp Val Gly Val Tyr Tyr Cys Gln His Ser Arg
                 85                  90                  95

Asp Leu Pro Leu Thr Phe Gly Gln Gly Thr Lys Leu Glu Ile Lys
             100                 105                 110

<210> SEQ ID NO 30
<211> LENGTH: 111
<212> TYPE: PRT
<213> ORGANISM: Artificial sequence
<220> FEATURE:
<223> OTHER INFORMATION: K09A light chain variable region

<400> SEQUENCE: 30

Asp Ile Val Met Thr Gln Thr Pro Leu Ser Leu Pro Val Thr Pro Gly
 1               5                  10                  15

Glu Pro Ala Ser Ile Ser Cys Arg Ala Ser Lys Gly Val Ser Thr Ser
                 20                  25                  30

Gly Tyr Ser Tyr Leu His Trp Tyr Leu Gln Lys Pro Gly Gln Ser Pro
                 35                  40                  45

Gln Leu Leu Ile Tyr Leu Ala Ser Tyr Leu Glu Ser Gly Val Pro Asp
             50                  55                  60

Arg Phe Ser Gly Ser Gly Ser Gly Thr Ala Phe Thr Leu Lys Ile Ser
 65                  70                  75                  80

Arg Val Glu Ala Glu Asp Val Gly Leu Tyr Tyr Cys Gln His Ser Arg
                 85                  90                  95

Asp Leu Pro Leu Thr Phe Gly Gln Gly Thr Lys Leu Glu Ile Lys
             100                 105                 110

<210> SEQ ID NO 31
<211> LENGTH: 447
<212> TYPE: PRT
<213> ORGANISM: Artificial sequence
<220> FEATURE:
<223> OTHER INFORMATION: mature 409 heavy chain

<400> SEQUENCE: 31

Gln Val Gln Leu Val Gln Ser Gly Val Glu Val Lys Lys Pro Gly Ala
 1               5                  10                  15

Ser Val Lys Val Ser Cys Lys Ala Ser Gly Tyr Thr Phe Thr Asn Tyr
                 20                  25                  30

Tyr Met Tyr Trp Val Arg Gln Ala Pro Gly Gln Gly Leu Glu Trp Met
                 35                  40                  45

Gly Gly Ile Asn Pro Ser Asn Gly Gly Thr Asn Phe Asn Glu Lys Phe
             50                  55                  60

Lys Asn Arg Val Thr Leu Thr Thr Asp Ser Ser Thr Thr Thr Ala Tyr
 65                  70                  75                  80

Met Glu Leu Lys Ser Leu Gln Phe Asp Asp Thr Ala Val Tyr Tyr Cys
                 85                  90                  95

Ala Arg Arg Asp Tyr Arg Phe Asp Met Gly Phe Asp Tyr Trp Gly Gln
             100                 105                 110
```

```
Gly Thr Thr Val Thr Val Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 32
<211> LENGTH: 218
<212> TYPE: PRT
<213> ORGANISM: Artificial sequence
<220> FEATURE:
<223> OTHER INFORMATION: mature K09A light chain

<400> SEQUENCE: 32

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30
```

Gly Tyr Ser Tyr Leu His Trp Tyr Gln Gln Lys Pro Gly Gln Ala Pro
            35                  40                  45

Arg Leu Leu Ile Tyr Leu Ala Ser Tyr Leu Glu Ser Gly Val Pro Ala
 50                  55                  60

Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
            210                 215

<210> SEQ ID NO 33
<211> LENGTH: 218
<212> TYPE: PRT
<213> ORGANISM: Artificial sequence
<220> FEATURE:
<223> OTHER INFORMATION: mature K09A light chain

<400> SEQUENCE: 33

Glu Ile Val Leu Thr Gln Ser Pro Leu Ser Leu Pro Val Thr Pro Gly
 1               5                  10                  15

Glu Pro Ala Ser Ile Ser Cys Arg Ala Ser Lys Gly Val Ser Thr Ser
            20                  25                  30

Gly Tyr Ser Tyr Leu His Trp Tyr Leu Gln Lys Pro Gly Gln Ser Pro
            35                  40                  45

Gln Leu Leu Ile Tyr Leu Ala Ser Tyr Leu Glu Ser Gly Val Pro Asp
 50                  55                  60

Arg Phe Ser Gly Ser Gly Ser Gly Thr Asp Phe Thr Leu Lys Ile Ser
 65                  70                  75                  80

Arg Val Glu Ala Glu Asp Val Gly Val Tyr Tyr Cys Gln His Ser Arg
                85                  90                  95

Asp Leu Pro Leu Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

```
Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 34
<211> LENGTH: 218
<212> TYPE: PRT
<213> ORGANISM: Artificial sequence
<220> FEATURE:
<223> OTHER INFORMATION: mature K09A light chain

<400> SEQUENCE: 34

Asp Ile Val Met Thr Gln Thr Pro Leu Ser Leu Pro Val Thr Pro Gly
1               5                   10                  15

Glu Pro Ala Ser Ile Ser Cys Arg Ala Ser Lys Gly Val Ser Thr Ser
            20                  25                  30

Gly Tyr Ser Tyr Leu His Trp Tyr Leu Gln Lys Pro Gly Gln Ser Pro
        35                  40                  45

Gln Leu Leu Ile Tyr Leu Ala Ser Tyr Leu Glu Ser Gly Val Pro Asp
    50                  55                  60

Arg Phe Ser Gly Ser Gly Ser Gly Thr Ala Phe Thr Leu Lys Ile Ser
65                  70                  75                  80

Arg Val Glu Ala Glu Asp Val Gly Leu Tyr Tyr Cys Gln His Ser Arg
                85                  90                  95

Asp Leu Pro Leu Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

STABLE FORMULATIONS OF PROGRAMMED DEATH RECEPTOR 1 (PD-1) ANTIBODIES AND METHODS OF USE THEREOF

CROSS-REFERENCE TO RELATED APPLICATIONS

This application is a U.S. National Phase application under 35 U.S.C. § 371 of PCT Application No. PCT/US2018/030459, filed May 1, 2018, which published as WO 2018/204368 A1 on Nov. 8, 2018, and claims priority under 35 U.S.C. § 119(e) from U.S. provisional patent application No. 62/500,238, filed May 2, 2017, the content of each of which is hereby incorporated by reference in its entirety.

FIELD OF THE INVENTION

The invention relates to stable formulations comprising antibodies or antigen binding fragments thereof that bind to human programmed death receptor 1 (PD-1). Also provided are methods of treating various cancers and chronic infections with the formulations of the invention.

REFERENCE TO SEQUENCE LISTING SUBMITTED ELECTRONICALLY

The sequence listing of the present application is submitted electronically via EFS-Web as an ASCII formatted sequence listing with a file name "24439USPCT-SEQLIST-23OCT2019.txt", creation date of Oct. 23, 2019, and a size of 33.4 Kb. This sequence listing submitted via EFS-Web is part of the specification and is herein incorporated by reference in its entirety.

BACKGROUND OF THE INVENTION

Immune checkpoint therapies targeting the programmed death receptor-1 (PD-1) axis have resulted in groundbreaking improvements in clinical response in multiple human cancers (Brahmer et al., *N Engl J Med* 2012, 366: 2455-65; Garon et al. *N Engl J Med* 2015, 372: 2018-28; Hamid et al., *N Engl J Med* 2013, 369: 134-44; Robert et al., *Lancet* 2014, 384: 1109-17; Robert et al., *N Engl J Med* 2015, 372: 2521-32; Robert et al., *N Engl J Med* 2015, 372: 320-30; Topalian et al., *N Engl J Med* 2012, 366: 2443-54; Topalian et al., *J Clin Oncol* 2014, 32: 1020-30; Wolchok et al., *N Engl J Med* 2013, 369: 122-33). The interaction of the PD-1 receptor on T-cells with its ligands, PD-L1 and PD-L2, on tumor and immune infiltrating cells regulates T-cell mediated immune responses and may play a role in immune escape by human tumors (Pardoll D M. *Nat Rev Cancer* 2012, 12: 252-64). Binding of PD-1 to either of its ligands results in delivery of an inhibitory stimulus to the T cell. Immune therapies targeting the PD-1 axis include monoclonal antibodies directed to the PD-1 receptor (KEYTRUDA™ (pembrolizumab), Merck and Co., Inc., Kenilworth, N.J. and OPDIVO™ (nivolumab), Bristol-Myers Squibb, Princeton, N.J.) and also those that bind to the PD-L1 ligand (MPDL3280A; TECENTRIQ™ (atezolizumab), Genentech, San Francisco, Calif.). Both therapeutic approaches have demonstrated anti-tumor effects in numerous cancer types.

Antibodies for use in human subjects must be stored prior to use and transported to the point of administration. Reproducibly attaining a desired level of antibody drug in a subject requires that the drug be stored in a formulation that maintains the bioactivity of the drug. The need exists for stable formulations of anti-human PD-1 antibodies for pharmaceutical use, e.g., for treating various cancers and infectious diseases. Preferably, such formulations will exhibit a long shelf-life, be stable when stored and transported, and will be amenable to administration at high concentrations, e.g. for use in subcutaneous administration, as well as low concentrations, e.g. for intravenous administration.

SUMMARY OF THE INVENTION

The invention provides an anti-human PD-1 antibody formulation, comprising: a) about 5 mg/mL to about 200 mg/mL of an anti-human PD-1 antibody, or antigen binding fragment thereof; b) about 5 mM to about 20 mM buffer; c) a stabilizer selected from the group consisting of: (i) about 6% to about 8% weight/volume (w/v) sucrose, trehalose or (2-hydroxypropyl)-β-cyclodextrin; (ii) about 3% to about 5% w/v mannitol, sorbitol, L-arginine, a pharmaceutically acceptable salt of L-arginine, L-proline, or a pharmaceutically acceptable salt of L-proline; and (iii) about 1.8 to about 2.2% w/v glycine, or a pharmaceutically acceptable salt thereof; d) about 0.01% to about 0.10% non-ionic surfactant; and e) about 1 mM to about 20 mM anti-oxidant.

In embodiments of the invention, the buffer provides a pH of between 5.0 and 6.0.

In specific embodiments, the stabilizer of the anti-human PD-1 antibody formulation is selected from the group consisting of: (i) about 6% to about 8% w/v sucrose, trehalose or (2-hydroxypropyl)-β-cyclodextrin; (ii) about 3% to about 5% mannitol, sorbitol, or L-proline, or a pharmaceutically acceptable salt of L-proline; and (iii) about 1.8 to about 2.2% w/v glycine, or a pharmaceutically acceptable salt thereof.

In certain embodiments, the anti-human PD-1 antibody formulation further comprises from about 1% to about 3% w/v L-arginine, or a pharmaceutically acceptable salt thereof.

The invention also provides an anti-human PD-1 antibody formulation comprising: a) about 25 mg/mL to about 200 mg/mL of an anti-human PD-1 antibody, or antigen binding fragment thereof; b) about 5 mM to about 20 mM histidine buffer; c) about 6% to about 8% w/v sucrose; d) about 0.01% to about 0.04% w/v polysorbate 80; and e) about 1 mM to about 20 mM L-methionine, or a pharmaceutically acceptable salt thereof.

In specific embodiments, the anti-human PD-1 antibody formulation further comprises from about 1% to about 3% w/v L-arginine, or a pharmaceutically acceptable salt thereof.

The invention further provides an anti-human PD-1 antibody formulation comprising: a) about 75 to about 200 mg/mL of an anti-human PD-1 antibody, or antigen binding fragment thereof; b) about 8 mM to about 12 mM histidine buffer; c) about 5 mM to about 10 mM methionine; d) about 6% to about 8% w/v sucrose; and e) 0.01% to about 0.04% w/v polysorbate 80.

Also provided by the invention is an anti-human PD-1 antibody formulation, comprising: a) about 125 to about 200 mg/mL of an anti-human PD-1 antibody, or antigen binding fragment thereof; b) about 10 mM histidine buffer; c) about 10 mM L-methionine or a pharmaceutically acceptable salt thereof, d) about 7 w/v sucrose; and e) about 0.02% to w/v polysorbate 80.

In some embodiments, the anti-human PD-1 antibody formulation further comprises from about 1.25% to about 2.5% w/v L-arginine, or a pharmaceutically acceptable salt thereof. In some embodiments, the arginine is L-arginine. In other embodiments, the arginine is L-arginine HCL.

The invention also provides an anti-human PD-1 antibody formulation, comprising: a) about 5 mg/mL to about 75 mg/mL of an anti-human PD-1 antibody, or antigen binding fragment thereof; b) about 8 mM to about 12 mM histidine buffer; c) a stabilizer selected from the group consisting of: (i) about 6% to about 8% w/v sucrose, trehalose or (2-hydroxypropyl)-β-cyclodextrin; (ii) about 3% to about 5% w/v mannitol, sorbitol, L-proline or a pharmaceutically acceptable salt of L-proline; and (iii) about 1.8 to about 2.2% w/v glycine, or a pharmaceutically acceptable salt thereof; d) about 0.01% to about 0.04% polysorbate 80; and e) about 5 mM to about 10 mM methionine or a pharmaceutically acceptable salt thereof.

In certain embodiments, the anti-human PD-1 antibody formulation further comprises a metal chelator. In specific embodiments, the metal chelator is DTPA. In certain embodiments the DTPA is present at a concentration of about 10 μM to about 30 μM.

The invention also provides a liquid anti-human PD-1 antibody formulation that is reconstituted from a lyophilized formulation wherein the reconstituted solution comprises: a) about 125 mg/mL to about 175 mg/mL of an anti-human PD-1 antibody, or antigen binding fragment thereof; b) about 8 mM to about 12 mM histidine buffer; c) a stabilizer selected from the group consisting of: (i) about 3% to about 8% w/v sucrose; (ii) about 2% to about 5% w/v L-arginine, or a pharmaceutically acceptable salt thereof; (iii) about 3% to about 5% mannitol and about 1% to about 2% sucrose; and (iv) a combination of i) and ii); and d) about 0.01% to about 0.04% polysorbate 80.

In specific embodiments of the invention the anti-PD-1 antibody is pembrolizumab or an antigen binding fragment of pembrolizumab.

Also provided herein are methods of treating cancer and methods of treating chronic infection in a human patient in need thereof comprising: administering an effective amount of the anti-human PD-1 antibody formulations of the invention to the patient.

BRIEF DESCRIPTION OF THE DRAWINGS

(FIG. 1A), 25° C. (FIG. 1B), and 40° C. (FIG. 1C).

(FIG. 2A), 25° C. (FIG. 2B), and 40° C. (FIG. 2C) over a 9-month period.

(FIG. 3A), 25° C. (FIG. 3B) and 40° C. (FIG. 3C).

(FIG. 3A), 25° C. (FIG. 3B) and 40° C. (FIG. 3C) over 12 weeks. The dashed lines in FIG. 4B and FIG. 4C shows results from Formulation 1, Example 3, as a comparator.

DETAILED DESCRIPTION OF THE INVENTION

Figure 1A:
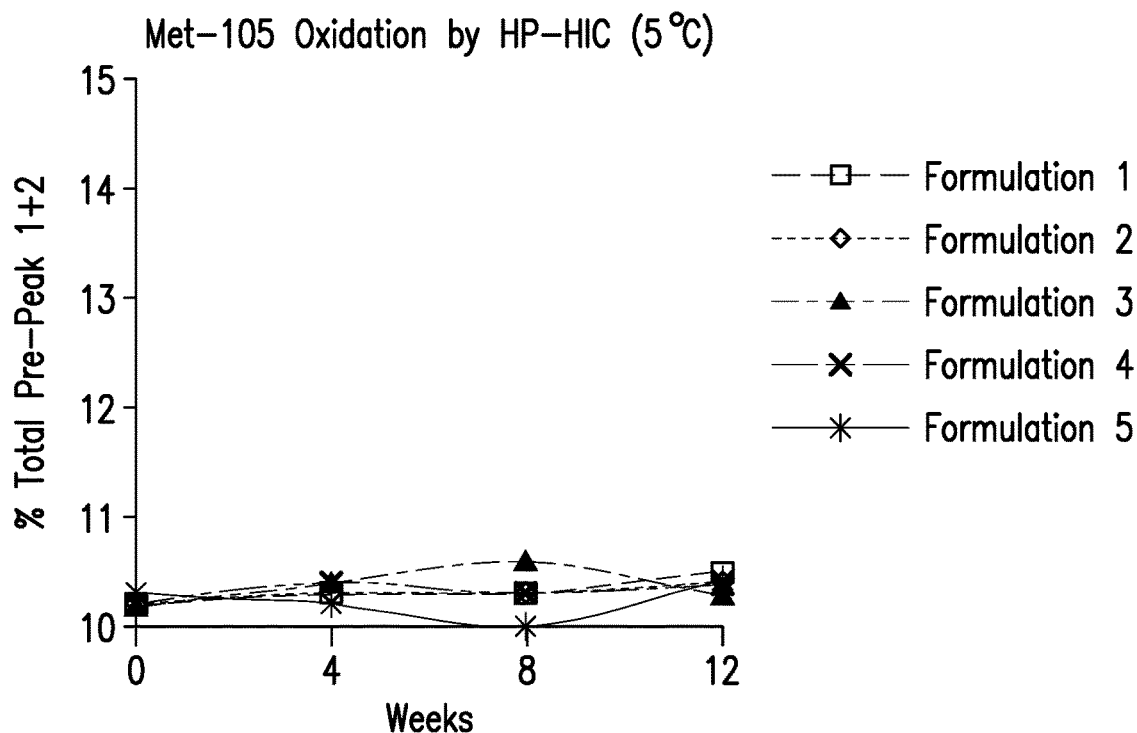
FIGS. 1A-1C show results of an HP-HIC study, which measures oxidation of Met-105, for high concentration pembrolizumab formulations over a 12-week time period. Results are provided for test formulations (see EXAMPLE 2) stored at 5° C.

The invention provides stable formulations comprising an anti-PD-1 antibody, or antigen binding fragment thereof that binds to human PD-1, which are useful for methods of treatment of cancer or an immune disorder or immune condition which comprise intravenous or subcutaneous administration to a patient in need thereof. In certain embodiments of the invention, the anti-PD-1 antibody is pembrolizumab or an antigen binding fragment of pembrolizumab. The formulations of the invention address the issues of high viscosity and increased aggregation associated with antibody formulations comprising a high concentration of anti-PD1 antibodies. The invention further provides formulations comprising pembrolizumab or an antigen binding fragment thereof with reduced methionine oxidation, including reduced oxidation of methionine-105, which is located in CDR3 of the heavy chains of pembrolizumab.

The formulations of the invention are useful for subcutaneous delivery to a patient in need thereof. In order to deliver maximum therapeutic benefits to patients, it is desirable that formulations for subcutaneous (SC) delivery comprise a high antibody concentration (75-200 mg/ml). A high concentration of API is often required for SC formulations due to the historical bioavailability of 50-60% for SC injections and the expected dose range of an antibody product. However, high concentration of antibody, or antigen binding fragment thereof, may contribute to other properties of the product which would be undesirable, e.g. low injectability due to increased viscosity and higher than physiological osmolality and increased aggregation. Therefore, it is preferred that an antibody product intended for SC administration balances the effects of concentration while maintaining a level of drug that will provide the highest therapeutic benefit. An ideal product comprises a high protein concentration, low viscosity, an osmolality similar to physiological conditions, and a low level of aggregation under typical storage conditions. Increased viscosity at high protein concentration may not only make it difficult to extract the product from its container with a syringe, but also to inject the necessary dose into a patient from the syringe (syringeability). Advantageously, embodiments of the invention provide formulations that comprise a high concentration of antibody, or antigen binding fragment thereof, and a viscosity level that is acceptable for subcutaneous delivery. Additionally, the formulations of the invention do not lead to high levels of aggregation, as shown in more detail throughout the Examples.

Previous forced degradation studies were conducted on pembrolizumab drug substance (DS) to investigate product degradation pathways and to isolate and characterize impurities. In these studies, pembrolizumab DS was exposed to various stress conditions, and analysis of stressed samples indicated that, under the stress conditions employed, pembrolizumab DS was sensitive to light, peroxide, and high pH. Major degradation pathways of pembrolizumab included oxidation of methionine 105 (Met105) in the heavy chain CDR upon peroxide stress and oxidation of Met105 and Fc methionine residues when exposed to light. Pembrolizumab maintained its bioactivity under most stress conditions for the degradation levels tested. However, reduction in affinity to PD-1 was observed for peroxide stressed samples by Surface Plasmon Resonance (SPR). An exposed methionine residue or a methionine residue in the CDR of an antibody has the potential of impacting the biological activity of the antibody through oxidation. It is shown herein that the formulations of the invention are able to reduce oxidation of Met105 within the pembrolizumab heavy chain CDR.

I. Definitions and Abbreviations

As used throughout the specification and appended claims, the following abbreviations apply:
API active pharmaceutical ingredient
CDR complementarity determining region in the immunoglobulin variable regions
CE-SDS capillary electrophoresis-sodium dodecyl sulfate
CHO Chinese hamster ovary
CI confidence interval
DS drug substance
EC50 concentration resulting in 50% efficacy or binding
ELISA enzyme-linked immunosorbant assay
FFPE formalin-fixed, paraffin-embedded
FR framework region
HC heavy chain
HNSCC head and neck squamous cell carcinoma
HPBC 2-Hydroxypropyl)-β-cyclodextrin
HP-HIC high performance hydrophobic interaction chromatography
HP-IEX high performance ion-exchange chromatography
HP-SEC high performance size exclusion chromatography
IC50 concentration resulting in 50% inhibition
IgG immunoglobulin G
IHC immunohistochemistry or immunohistochemical
mAb monoclonal antibody
MES 2-(N-morpholino)ethanesulfonic acid
NCBI National Center for Biotechnology Information
NSCLC non-small cell lung cancer
PCR polymerase chain reaction
PD-1 programmed death 1 (a.k.a. programmed cell death-1 and programmed death receptor 1)
PD-L1 programmed cell death 1 ligand 1
PD-L2 programmed cell death 1 ligand 2
PS80 or PS-80 polysorbate 80
SBEC (sulfobutylether)-β-cyclodextrin
SWFI sterile water for injection
TNBC triple negative breast cancer
$V_H$ immunoglobulin heavy chain variable region
VK immunoglobulin kappa light chain variable region
$V_L$ immunoglobulin light chain variable region
VP-DSC Valerian-Plotnikov differential scanning calorimetry
v/v volume per volume
WFI water for injection
w/v weight per volume So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

As used throughout the specification and in the appended claims, the singular forms "a," "an," and "the" include the plural reference unless the context clearly dictates otherwise.

Reference to "or" indicates either or both possibilities unless the context clearly dictates one of the indicated possibilities. In some cases, "and/or" was employed to highlight either or both possibilities.

"Treat" or "treating" a cancer as used herein means to administer a formulation of the invention to a subject having an immune condition or cancerous condition, or diagnosed with a cancer or pathogenic infection (e.g. viral, bacterial, fungal), to achieve at least one positive therapeutic effect, such as for example, reduced number of cancer cells, reduced tumor size, reduced rate of cancer cell infiltration into peripheral organs, or reduced rate of tumor metastasis or tumor growth. "Treatment" may include one or more of the following: inducing/increasing an antitumor immune response, stimulating an immune response to a pathogen, toxin, and/or self-antigen, stimulating an immune response to a viral infection, decreasing the number of one or more tumor markers, halting or delaying the growth of a tumor or blood cancer or progression of disease associated with PD-1 binding to its ligands PD-L1 and/or PD-L2 ("PD-1-related disease") such as cancer, stabilization of PD-1-related disease, inhibiting the growth or survival of tumor cells, eliminating or reducing the size of one or more cancerous lesions or tumors, decreasing the level of one or more tumor markers, ameliorating, abrogating the clinical manifestations of PD-1-related disease, reducing the severity or duration of the clinical symptoms of PD-1-related disease such as cancer, prolonging the survival of a patient relative to the expected survival in a similar untreated patient, inducing complete or partial remission of a cancerous condition or other PD-1 related disease.

"Immune condition" or "immune disorder" encompasses, e.g., pathological inflammation, an inflammatory disorder, and an autoimmune disorder or disease. "Immune condition" also refers to infections, persistent infections, and proliferative conditions, such as cancer, tumors, and angiogenesis, including infections, tumors, and cancers that resist eradication by the immune system. "Cancerous condition" includes, e.g., cancer, cancer cells, tumors, angiogenesis, and precancerous conditions such as dysplasia.

Positive therapeutic effects in cancer can be measured in a number of ways (See, W. A. Weber, *J. Nucl. Med.* 50:1 S-10S (2009)). For example, with respect to tumor growth inhibition, according to NCI standards, a T/C≤42% is the minimum level of anti-tumor activity. A T/C<10% is considered a high anti-tumor activity level, with T/C (%)=Median tumor volume of the treated/Median tumor volume of the control×100. In some embodiments, the treatment achieved by administration of a formulation of the invention is any of progression free survival (PFS), disease free survival (DFS) or overall survival (OS). PFS, also referred to as "Time to Tumor Progression" indicates the length of time during and after treatment that the cancer does not grow, and includes the amount of time patients have experienced a complete response or a partial response, as well as the amount of time patients have experienced stable disease. DFS refers to the length of time during and after treatment that the patient remains free of disease. OS refers to a prolongation in life expectancy as compared to naive or untreated individuals or patients. While an embodiment of the formulations, treatment methods, and uses of the invention may not be effective in achieving a positive therapeutic effect in every patient, it should do so in a statistically significant number of subjects as determined by any statistical test known in the art such as the Student's t-test, the chi²-test, the U-test according to Mann and Whitney, the Kruskal-Wallis test (H-test), Jonckheere-Terpstra-test and the Wilcoxon-test.

The term "patient" (alternatively referred to as "subject" or "individual" herein) refers to a mammal (e.g., rat, mouse, dog, cat, rabbit) capable of being treated with the formulations of the invention, most preferably a human. In some embodiments, the patient is an adult patient. In other embodiments, the patient is a pediatric patient. Those "in need of treatment" include those patients that may benefit from treatment with the formulations of the invention, e.g. a patient suffering from cancer or an immune condition.

The term "antibody" refers to any form of antibody that exhibits the desired biological activity. Thus, it is used in the broadest sense and specifically covers, but is not limited to, monoclonal antibodies (including full length monoclonal antibodies), polyclonal antibodies, humanized, fully human antibodies, and chimeric antibodies.

In general, the basic antibody structural unit comprises a tetramer. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The variable regions of each light/heavy chain pair form the antibody binding site. Thus, in general, an intact antibody has two binding sites. The carboxy-terminal portion of the heavy chain may define a constant region primarily responsible for effector function. Typically, human light chains are classified as kappa and lambda light chains. Furthermore, human heavy chains are typically classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989).

Typically, the variable domains of both the heavy and light chains comprise three hypervariable regions, also called complementarity determining regions (CDRs), which are located within relatively conserved framework regions (FR). The CDRs are usually aligned by the framework regions, enabling binding to a specific epitope. In general, from N-terminal to C-terminal, both light and heavy chains variable domains comprise FR1, CDR1, FR2, CDR2, FR3, CDR3 and FR4. The assignment of amino acids to each domain is, generally, in accordance with the definitions of Sequences of Proteins of Immunological Interest, Kabat, et al.; National Institutes of Health, Bethesda, Md.; $5^{th}$ ed.; NIH Publ. No. 91-3242 (1991); Kabat (1978) *Adv. Prot. Chem.* 32:1-75; Kabat, et al., (1977) *J. Biol. Chem.* 252: 6609-6616; Chothia, et al., (1987) *J Mol. Biol.* 196:901-917 or Chothia, et al., (1989) *Nature* 342:878-883.

An antibody or antigen-binding fragment that "specifically binds to" a specified target protein is an antibody that exhibits preferential binding to that target as compared to other proteins, but this specificity does not require absolute binding specificity. An antibody is considered "specific" for its intended target if its binding is determinative of the presence of the target protein in a sample, e.g. without producing undesired results such as false positives. Antibodies, or binding fragments thereof, useful in the invention will bind to the target protein with an affinity that is at least two fold greater, preferably at least ten times greater, more preferably at least 20-times greater, and most preferably at least 100-times greater than the affinity with non-target proteins. As used herein, an antibody is said to bind specifically to a polypeptide comprising a given amino acid sequence, e.g. the amino acid sequence of a mature human PD-1 or human PD-L1 molecule, if it binds to polypeptides comprising that sequence but does not bind to proteins lacking that sequence.

"Chimeric antibody" refers to an antibody in which a portion of the heavy and/or light chain is identical with or homologous to corresponding sequences in an antibody derived from a particular species (e.g., human) or belonging to a particular antibody class or subclass, while the remainder of the chain(s) is identical with or homologous to corresponding sequences in an antibody derived from another species (e.g., mouse) or belonging to another antibody class or subclass, as well as fragments of such antibodies, so long as they exhibit the desired biological activity.

The term "pharmaceutically effective amount" or "effective amount" means an amount whereby sufficient therapeutic composition or formulation is introduced to a patient to treat a diseased or condition. One skilled in the art recognizes that this level may vary according the patient's characteristics such as age, weight, etc.

The term "about", when modifying the quantity (e.g., mM, or M) of a substance or composition, the percentage (v/v or w/v) of a formulation component, the pH of a solution/formulation, or the value of a parameter characterizing a step in a method, or the like refers to variation in the numerical quantity that can occur, for example, through typical measuring, handling and sampling procedures involved in the preparation, characterization and/or use of the substance or composition; through inadvertent error in these procedures; through differences in the manufacture, source, or purity of the ingredients employed to make or use the compositions or carry out the procedures; and the like. In certain embodiments, "about" can mean a variation of ±0.1%, 0.5%, 1%, 2%, 3%, 4%, 5% or 10%.

The terms "cancer", "cancerous", or "malignant" refer to or describe the physiological condition in mammals that is typically characterized by unregulated cell growth. Examples of cancer include but are not limited to, carcinoma, lymphoma, leukemia, blastoma, and sarcoma. More particular examples of such cancers include squamous cell carcinoma, myeloma, small-cell lung cancer, non-small cell lung cancer, glioma, Hodgkin's lymphoma, non-Hodgkin's lymphoma, gastrointestinal (tract) cancer, renal cancer, ovarian cancer, liver cancer, lymphoblastic leukemia, lymphocytic leukemia, colorectal cancer, endometrial cancer, kidney cancer, prostate cancer, thyroid cancer, melanoma, chondrosarcoma, neuroblastoma, pancreatic cancer, glioblastoma multiforme, cervical cancer, brain cancer, stomach cancer, bladder cancer, hepatoma, breast cancer, colon carcinoma, and head and neck cancer.

A "chemotherapeutic agent" is a chemical compound useful in the treatment of cancer. Anti-PD-1 antibodies can be used with any one or more suitable chemotherapeutic agent. Examples of such chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin gammaII and calicheamicin phiI1, see, e.g., Agnew, Chem. Intl. Ed. Engl., 33:183-186 (1994); dynemicin, including dynemicin A; bisphosphonates, such as clodronate; an esperamicin; as well as neocarzinostatin chromophore and related chromoprotein enediyne antibiotic chromomophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; losoxantrone; podophyllinic acid; 2-ethylhydrazide; procarbazine; razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel and doxetaxel; chlorambucil; gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids or derivatives of any of the above. Also included are anti-hormonal agents that act to regulate or inhibit hormone action on tumors such as anti-estrogens and selective estrogen receptor modulators (SERMs), including, for example, tamoxifen, raloxifene, droloxifene, 4-hydroxytamoxifen, trioxifene, keoxifene, LY117018, onapristone, and toremifene (Fareston); aromatase inhibitors that inhibit the enzyme aromatase, which regulates estrogen production in the adrenal glands, such as, for example, 4(5)-imidazoles, aminoglutethimide, megestrol acetate, exemestane, formestane, fadrozole, vorozole, letrozole, and anastrozole; and anti-androgens such as flutamide, nilutamide, bicalutamide, leuprolide, and goserelin; and pharmaceutically acceptable salts, acids or derivatives of any of the above.

"Chothia" means an antibody numbering system described in Al-Lazikani et al., *JMB* 273:927-948 (1997).

"Kabat" as used herein means an immunoglobulin alignment and numbering system pioneered by Elvin A. Kabat ((1991) Sequences of Proteins of Immunological Interest, 5th Ed. Public Health Service, National Institutes of Health, Bethesda, Md.).

A "growth inhibitory agent" when used herein refers to a compound or composition which inhibits growth of a cell, especially cancer cell over expressing any of the genes identified herein, either in vitro or in vivo. Thus, the growth inhibitory agent is one which significantly reduces the percentage of cells over expressing such genes in S phase. Examples of growth inhibitory agents include agents that block cell cycle progression (at a place other than S phase), such as agents that induce G1 arrest and M-phase arrest. Classical M-phase blockers include the vincas (vincristine and vinblastine) taxanes, and topo II inhibitors such as doxorubicin, epirubicin, daunorubicin, and etoposide. Those agents that arrest G1 also spill over into S-phase arrest, for example, DNA alkylating agents such as dacarbazine, mechlorethamine, and cisplatin. Further information can be found in *The Molecular Basis of Cancer*, Mendelsohn and Israel, eds., Chapter 1, entitled "Cell cycle regulation, oncogens, and antineoplastic drugs" by Murakami et al. (WB Saunders: Philadelphia, 1995).

The terms "PD-1 binding fragment," "antigen binding fragment thereof," "binding fragment thereof" or "fragment thereof" encompass a fragment or a derivative of an antibody that still substantially retains its biological activity of binding to antigen (human PD-1) and inhibiting its activity (e.g., blocking the binding of PD-1 to PDL1 and PDL2). Therefore, the term "antibody fragment" or PD-1 binding fragment refers to a portion of a full length antibody, generally the antigen binding or variable region thereof. Examples of antibody fragments include Fab, Fab', F(ab')2, and Fv fragments. Typically, a binding fragment or derivative retains at least 10% of its PD-1 inhibitory activity. In some embodiments, a binding fragment or derivative retains at least 25%, 50%, 60%, 70%, 80%, 90%, 95%, 99% or 100% (or more) of its PD-1 inhibitory activity, although any binding fragment with sufficient affinity to exert the desired biological effect will be useful. In some embodiments, an antigen binding fragment binds to its antigen with an affinity that is at least two fold greater, preferably at least ten times greater, more preferably at least 20-times greater, and most preferably at least 100-times greater than the affinity with unrelated antigens. In one embodiment the antibody has an affinity that is greater than about $10^9$ liters/mol, as determined, e.g., by Scatchard analysis. Munsen et al. (1980) *Analyt. Biochem.* 107:220-239. It is also intended that a PD-1 binding fragment can include variants having conservative amino acid substitutions that do not substantially alter its biologic activity.

"Humanized antibody" refers to forms of antibodies that contain sequences from non-human (e.g., murine) antibodies as well as human antibodies. Such antibodies contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. The humanized forms of rodent antibodies will generally comprise the same CDR sequences of the parental rodent antibodies, although certain amino acid substitutions may be included to increase affinity, increase stability of the humanized antibody, or for other reasons.

The antibodies of the invention also include antibodies with modified (or blocked) Fc regions to provide altered effector functions. See, e.g., U.S. Pat. No. 5,624,821; WO2003/086310; WO2005/120571; WO2006/0057702; Presta (2006) *Adv. Drug Delivery Rev.* 58:640-656. Such modification can be used to enhance or suppress various reactions of the immune system, with possible beneficial effects in diagnosis and therapy. Alterations of the Fc region include amino acid changes (substitutions, deletions and insertions), glycosylation or deglycosylation, and adding multiple Fc. Changes to the Fc can also alter the half-life of antibodies in therapeutic antibodies, and a longer half-life would result in less frequent dosing, with the concomitant increased convenience and decreased use of material. See Presta (2005) *J. Allergy Clin. Immunol.* 116:731 at 734-35.

"Fully human antibody" refers to an antibody that comprises human immunoglobulin protein sequences only. A fully human antibody may contain murine carbohydrate chains if produced in a mouse, in a mouse cell, or in a hybridoma derived from a mouse cell. Similarly, "mouse antibody" refers to an antibody which comprises mouse immunoglobulin sequences only. A fully human antibody may be generated in a human being, in a transgenic animal having human immunoglobulin germline sequences, by phage display or other molecular biological methods.

"Hypervariable region" refers to the amino acid residues of an antibody that are responsible for antigen-binding. The hypervariable region comprises amino acid residues from a "complementarity determining region" or "CDR" (e.g. residues 24-34 (CDRL1), 50-56 (CDRL2) and 89-97 (CDRL3) in the light chain variable domain and residues 31-35 (CDRH1), 50-65 (CDRH2) and 95-102 (CDRH3) in the heavy chain variable domain as measured by the Kabat numbering system (Kabat et al. (1991) Sequences of Proteins of Immunological Interest, 5th Ed. Public Health Service, National Institutes of Health, Bethesda, Md.) and/or those residues from a "hypervariable loop" (i.e. residues 26-32 (L1), 50-52 (L2) and 91-96 (L3) in the light chain variable domain and 26-32 (H1), 53-55 (H2) and 96-101 (H3) in the heavy chain variable domain (Chothia and Lesk (1987) *J Mol. Biol.* 196: 901-917). As used herein, the term "framework" or "FR" residues refers to those variable domain residues other than the hypervariable region residues defined herein as CDR residues. CDR and FR residues are determined according to the standard sequence definition of Kabat. Kabat et al. (1987) Sequences of Proteins of Immunological Interest, National Institutes of Health, Bethesda Md.

"Conservatively modified variants" or "conservative substitution" refers to substitutions of amino acids are known to those of skill in this art and may be made generally without altering the biological activity of the resulting molecule, even in essential regions of the polypeptide. Such exemplary substitutions are preferably made in accordance with those set forth in Table 1 as follows:

TABLE 1

Exemplary Conservative Amino Acid Substitutions

| Original residue | Conservative substitution |
| --- | --- |
| Ala (A) | Gly; Ser |
| Arg (R) | Lys, His |
| Asn (N) | Gln;His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

In addition, those of skill in this art recognize that, in general, single amino acid substitutions in non-essential regions of a polypeptide do not substantially alter biological activity. See, e.g., Watson et al. (1987) *Molecular Biology of the Gene*, The Benjamin/Cummings Pub. Co., p. 224 (4th Edition).

The phrase "consists essentially of," or variations such as "consist essentially of" or "consisting essentially of," as used throughout the specification and claims, indicate the inclusion of any recited elements or group of elements, and the optional inclusion of other elements, of similar or different nature than the recited elements, that do not materially change the basic or novel properties of the specified dosage regimen, method, or composition. As a non-limiting example, a binding compound that consists essentially of a recited amino acid sequence may also include one or more amino acids, including substitutions of one or more amino acid residues, that do not materially affect the properties of the binding compound.

"Comprising" or variations such as "comprise", "comprises" or "comprised of" are used throughout the specification and claims in an inclusive sense, i.e., to specify the presence of the stated features but not to preclude the presence or addition of further features that may materially enhance the operation or utility of any of the embodiments of the invention, unless the context requires otherwise due to express language or necessary implication.

"Isolated antibody" and "isolated antibody fragment" refers to the purification status and in such context means the named molecule is substantially free of other biological molecules such as nucleic acids, proteins, lipids, carbohydrates, or other material such as cellular debris and growth media. Generally, the term "isolated" is not intended to refer to a complete absence of such material or to an absence of water, buffers, or salts, unless they are present in amounts that substantially interfere with experimental or therapeutic use of the binding compound as described herein.

"Monoclonal antibody" or "mAb" or "Mab", as used herein, refers to a population of substantially homogeneous antibodies, i.e., the antibody molecules comprising the population are identical in amino acid sequence except for possible naturally occurring mutations that may be present in minor amounts. In contrast, conventional (polyclonal) antibody preparations typically include a multitude of different antibodies having different amino acid sequences in their variable domains, particularly their CDRs, which are often specific for different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the invention may be made by the hybridoma method first described by Kohler et al. (1975) Nature 256: 495, or may be made by recombinant DNA methods (see, e.g., U.S. Pat. No. 4,816,567). The "monoclonal antibodies" may also be isolated from phage antibody libraries using the techniques described in Clackson et al. (1991) Nature 352: 624-628 and Marks et al. (1991) J. Mol. Biol. 222: 581-597, for example. See also Presta (2005)J. Allergy Clin. Immunol. 116:731.

"Tumor" as it applies to a subject diagnosed with, or suspected of having, a cancer refers to a malignant or potentially malignant neoplasm or tissue mass of any size, and includes primary tumors and secondary neoplasms. A solid tumor is an abnormal growth or mass of tissue that usually does not contain cysts or liquid areas. Different types of solid tumors are named for the type of cells that form them. Examples of solid tumors are sarcomas, carcinomas, and lymphomas. Leukemias (cancers of the blood) generally do not form solid tumors (National Cancer Institute, Dictionary of Cancer Terms).

The term "tumor size" refers to the total size of the tumor which can be measured as the length and width of a tumor. Tumor size may be determined by a variety of methods known in the art, such as, e.g. by measuring the dimensions of tumor(s) upon removal from the subject, e.g., using calipers, or while in the body using imaging techniques, e.g., bone scan, ultrasound, CT or MRI scans.

"Variable regions" or "V region" as used herein means the segment of IgG chains which is variable in sequence between different antibodies. It extends to Kabat residue 109 in the light chain and 113 in the heavy chain.

The term "buffer" encompasses those agents which maintain the solution pH of the formulations of the invention in an acceptable range, or, for lyophilized formulations of the invention, provide an acceptable solution pH prior to lyophilization.

The terms "lyophilization," "lyophilized," and "freeze-dried" refer to a process by which the material to be dried is first frozen and then the ice or frozen solvent is removed by sublimation in a vacuum environment. An excipient may be included in pre-lyophilized formulations to enhance stability of the lyophilized product upon storage.

The term "pharmaceutical formulation" refers to preparations which are in such form as to permit the active ingredients to be effective, and which contains no additional components which are toxic to the subjects to which the formulation would be administered. The term "formulation" and "pharmaceutical formulation" are used interchangeably throughout.

"Pharmaceutically acceptable" refers to excipients (vehicles, additives) and compositions that can reasonably be administered to a subject to provide an effective dose of the active ingredient employed and that are "generally regarded as safe" e.g., that are physiologically tolerable and do not typically produce an allergic or similar untoward reaction, such as gastric upset and the like, when administered to a human. In another embodiment, this term refers to molecular entities and compositions approved by a regulatory agency of the federal or a state government or listed in the U.S. Pharmacopeia or another generally recognized pharmacopeia for use in animals, and more particularly in humans.

A "reconstituted" formulation is one that has been prepared by dissolving a lyophilized protein formulation in a diluent such that the protein is dispersed in the reconstituted formulation. The reconstituted formulation is suitable for administration, e.g. parenteral administration), and may optionally be suitable for subcutaneous administration.

"Reconstitution time" is the time that is required to rehydrate a lyophilized formulation with a solution to a particle-free clarified solution.

A "stable" formulation is one in which the protein therein essentially retains its physical stability and/or chemical stability and/or biological activity upon storage. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10:29-90 (1993). Stability can be measured at a selected temperature for a selected time period.

A "stable" formulation is one in which the protein therein essentially retains its physical stability and/or chemical stability and/or biological activity upon storage. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10:29-90 (1993). Stability can be measured at a selected temperature for a selected time period. For example, in one embodiment, a stable formulation is a formulation with no significant changes observed at a refrigerated temperature (2-8° C.) for at least 12 months. In another embodiment, a stable formulation is a formulation with no significant changes observed at a refrigerated temperature (2-8° C.) for at least 18 months. In another embodiment, stable formulation is a formulation with no significant changes observed at room temperature (23-27° C.) for at least 3 months. In another embodiment, stable formulation is a formulation with no significant changes observed at room temperature (23-27° C.) for at least 6 months. In another embodiment, stable formulation is a formulation with no significant changes observed at room temperature (23-27° C.) for at least 12 months. In another embodiment, stable formulation is a formulation with no significant changes observed at room temperature (23-27° C.) for at least 18 months. The criteria for stability for an antibody formulation are as follows. Typically, no more than 10%, preferably 5%, of antibody monomer is degraded as measured by SEC-HPLC. Typically, the formulation is colorless, or clear to slightly opalescent by visual analysis. Typically, the concentration, pH and osmolality of the formulation have no more than +/−10% change. Potency is typically within 60-140%, preferably 80-120% of the control or reference. Typically, no more than 10%, preferably 5% of clipping of the antibody is observed, i.e., % low molecular weight species as determined, for example, by HP-SEC. Typically, no more than 10%, preferably no more than 5% of aggregation of the antibody is observed, i.e. % high molecular weight species as determined, for example, by HP-SEC.

An antibody "retains its physical stability" in a pharmaceutical formulation if it shows no significant increase of aggregation, precipitation and/or denaturation upon visual examination of color and/or clarity, or as measured by UV light scattering, size exclusion chromatography (SEC) and dynamic light scattering. The changes of protein conformation can be evaluated by fluorescence spectroscopy, which determines the protein tertiary structure, and by FTIR spectroscopy, which determines the protein secondary structure.

An antibody "retains its chemical stability" in a pharmaceutical formulation, if it shows no significant chemical alteration. Chemical stability can be assessed by detecting and quantifying chemically altered forms of the protein. Degradation processes that often alter the protein chemical structure include hydrolysis or clipping (evaluated by methods such as size exclusion chromatography and SDS-PAGE), oxidation (evaluated by methods such as by peptide mapping in conjunction with mass spectroscopy or MALDI/TOF/MS), deamidation (evaluated by methods such as ion-exchange chromatography, capillary isoelectric focusing, peptide mapping, isoaspartic acid measurement), and isomerization (evaluated by measuring the isoaspartic acid content, peptide mapping, etc.).

An antibody "retains its biological activity" in a pharmaceutical formulation, if the biological activity of the antibody at a given time is within a predetermined range of the biological activity exhibited at the time the pharmaceutical formulation was prepared. The biological activity of an antibody can be determined, for example, by an antigen binding assay. Formulations of the invention include antibodies and fragments thereof that are biologically active when reconstituted or in liquid form The term "isotonic" means that the formulation of interest has essentially the same osmotic pressure as human blood. Isotonic formulations will generally have an osmotic pressure from about 270-328 mOsm. Slightly hypotonic pressure is 250-269 and slightly hypertonic pressure is 328-350 mOsm. Osmotic pressure can be measured, for example, using a vapor pressure or ice-freezing type osmometer.

A "non-reducing sugar" is a sugar not capable of acting as a reducing agent because it does not contain or cannot be converted to contain a free aldehyde group or a free ketone group. Examples of non-reducing sugars include but are not limited to disaccharides such as sucrose and trehalose.

"Pembrolizumab" (formerly known as MK-3475, SCH 900475 and lambrolizumab) alternatively referred to herein as "pembro," is a humanized IgG4 mAb with the structure described in *WHO Drug Information*, Vol. 27, No. 2, pages 161-162 (2013) and which comprises the heavy and light chain amino acid sequences and CDRs described in Table 2. Pembrolizumab has been approved by the U.S. FDA for the treatment of patients with unresectable or metastatic melanoma and for the treatment of certain patients with recurrent or metastatic head and neck squamous cell cancer (HNSCC), classical Hodgkin lymphoma (cHL), urothelial carcinoma, gastric cancer, microsatellite instability-high (MSI-H) cancer and non-small cell lung cancer, as described in the Prescribing Information for KEYTRUDA™ (Merck & Co., Inc., Whitehouse Station, N.J. USA; initial U.S. approval 2014, updated September 2017).

II. Formulations of the Invention

The formulations of the invention minimize the formation of antibody aggregates and particulates, high and low molecular weight species, minimize oxidation of methionine residues, and Met105 of pembrolizumab in particular, and ensure that the antibody retains biological activity over time.

The invention includes various formulations of a PD-1 antibody, or antigen binding fragment thereof, as described in more detail, infra. For example, the invention includes formulations comprising (i) an anti-PD-1 antibody or antigen binding fragment thereof, (ii) a buffer (e.g., histidine or acetate), (iii) a stabilizer (e.g., a non-reducing sugar such as sucrose or trehalose, or sorbitol, mannitol, (2-hydroxypropyl)-β-cyclodextrin, arginine, proline, or glycine); (iv) a non-ionic surfactant (e.g., polysorbate 80); and (v) an anti-oxidant (e.g., methionine). In further embodiments, the formulations of the invention comprise a viscosity-reducer (e.g. arginine, or a pharmaceutically acceptable salt thereof) and/or a metal chelator (e.g. DTPA).

Anti-PD-1 Antibodies and Antigen-Binding Fragments Thereof

The invention provides stable biological formulations comprising antibodies or antigen binding fragments thereof, which specifically bind to human PD-1 (e.g. a human or humanized anti-PD-1 antibody) as the active pharmaceutical ingredient (API), as well as methods for using the formulations of the invention. Any anti-PD-1 antibody or antigen binding fragment thereof can be used in the formulations and methods of the invention. In particular embodiments, the API is an anti-PD-1 antibody, which is selected from pembrolizumab and nivolumab. In specific embodiments, the anti-PD-1 antibody is pembrolizumab. In alternative embodiments, the anti-PD-1 antibody is nivolumab. Table 2 provides amino acid sequences for exemplary anti-human PD-1 antibodies pembrolizumab and nivolumab. Alternative PD-1 antibodies and antigen-binding fragments that are useful in the formulations and methods of the invention are shown in Table 3.

In some embodiments, an anti-human PD-1 antibody or antigen binding fragment thereof for use in the formulations of the invention comprises three light chain CDRs of CDRL1, CDRL2 and CDRL3 and/or three heavy chain CDRs of CDRH1, CDRH2 and CDRH3.

In one embodiment of the invention, CDRL1 is SEQ ID NO:1 or a variant of SEQ ID NO:1, CDRL2 is SEQ ID NO:2 or a variant of SEQ ID NO:2, and CDRL3 is SEQ ID NO:3 or a variant of SEQ ID NO:3.

In one embodiment, CDRH1 is SEQ ID NO:6 or a variant of SEQ ID NO:6, CDRH2 is SEQ ID NO: 7 or a variant of SEQ ID NO:7, and CDRH3 is SEQ ID NO:8 or a variant of SEQ ID NO:8.

In one embodiment, the three light chain CDRs are SEQ ID NO: 1, SEQ ID NO:2, and SEQ ID NO:3 and the three heavy chain CDRs are SEQ ID NO:6, SEQ ID NO:7 and SEQ ID NO:8.

In an alternative embodiment of the invention, CDRL1 is SEQ ID NO: 11 or a variant of SEQ ID NO:11, CDRL2 is SEQ ID NO:12 or a variant of SEQ ID NO:12, and CDRL3 is SEQ ID NO:13 or a variant of SEQ ID NO:13.

In one embodiment, CDRH1 is SEQ ID NO:16 or a variant of SEQ ID NO:16, CDRH2 is SEQ ID NO:17 or a variant of SEQ ID NO:17, and CDRH3 is SEQ ID NO:18 or a variant of SEQ ID NO:18.

In one embodiment, the three light chain CDRs are SEQ ID NO:1, SEQ ID NO:2, and SEQ ID NO:3 and the three heavy chain CDRs are SEQ ID NO:6, SEQ ID NO:7 and SEQ ID NO:8.

In an alternative embodiment, the three light chain CDRs are SEQ ID NO: 11, SEQ ID NO: 12, and SEQ ID NO: 13 and the three heavy chain CDRs are SEQ ID NO: 16, SEQ ID NO:17 and SEQ ID NO:18.

In a further embodiment of the invention, CDRL1 is SEQ ID NO:21 or a variant of SEQ ID NO:21, CDRL2 is SEQ ID NO:22 or a variant of SEQ ID NO:22, and CDRL3 is SEQ ID NO:23 or a variant of SEQ ID NO:23.

In yet another embodiment, CDRH1 is SEQ ID NO:24 or a variant of SEQ ID NO:24, CDRH2 is SEQ ID NO: 25 or a variant of SEQ ID NO:25, and CDRH3 is SEQ ID NO:26 or a variant of SEQ ID NO:26.

In another embodiment, the three light chain CDRs are SEQ ID NO:21, SEQ ID NO:22, and SEQ ID NO:23 and the three heavy chain CDRs are SEQ ID NO:24, SEQ ID NO:25 and SEQ ID NO:26.

Some antibody and antigen binding fragments of the formulations of the invention comprise a light chain variable region and a heavy chain variable region. In some embodiments, the light chain variable region comprises SEQ ID NO:4 or a variant of SEQ ID NO:4, and the heavy chain variable region comprises SEQ ID NO:9 or a variant of SEQ ID NO:9. In further embodiments, the light chain variable region comprises SEQ ID NO: 14 or a variant of SEQ ID NO: 14, and the heavy chain variable region comprises SEQ ID NO: 19 or a variant of SEQ ID NO: 19. In further embodiments, the heavy chain variable region comprises SEQ ID NO:27 or a variant of SEQ ID NO:27 and the light chain variable region comprises SEQ ID NO:28 or a variant of SEQ ID NO:28, SEQ ID NO:29 or a variant of SEQ ID NO:29, or SEQ ID NO:30 or a variant of SEQ ID NO:30. In such embodiments, a variant light chain or heavy chain variable region sequence is identical to the reference sequence except having one, two, three, four or five amino acid substitutions. In some embodiments, the substitutions are in the framework region (i.e., outside of the CDRs). In some embodiments, one, two, three, four or five of the amino acid substitutions are conservative substitutions.

In one embodiment of the formulations of the invention, the antibody or antigen binding fragment comprises a light chain variable region comprising or consisting of SEQ ID NO:4 and a heavy chain variable region comprising or consisting SEQ ID NO:9. In a further embodiment, the antibody or antigen binding fragment comprises a light chain variable region comprising or consisting of SEQ ID NO: 14 and a heavy chain variable region comprising or consisting of SEQ ID NO: 19. In one embodiment of the formulations of the invention, the antibody or antigen binding fragment comprises a light chain variable region comprising or consisting of SEQ ID NO:28 and a heavy chain variable region comprising or consisting SEQ ID NO:27. In a further embodiment, the antibody or antigen binding fragment comprises a light chain variable region comprising or consisting of SEQ ID NO:29 and a heavy chain variable region comprising or consisting SEQ ID NO:27. In another embodiment, the antibody or antigen binding fragment comprises a light chain variable region comprising or consisting of SEQ ID NO:30 and a heavy chain variable region comprising or consisting SEQ ID NO:27.

In another embodiment, the formulations of the invention comprise an antibody or antigen binding protein that has a $V_L$ domain and/or a $V_H$ domain with at least 95%, 90%, 85%, 80%, 75% or 50% sequence homology to one of the $V_L$ domains or $V_H$ domains described above, and exhibits specific binding to PD-1. In another embodiment, the antibody or antigen binding protein of the formulations of the invention comprises $V_L$ and $V_H$ domains having up to 1, 2, 3, 4, or 5 or more amino acid substitutions, and exhibits specific binding to PD-1.

In any of the embodiments above, the API may be a full-length anti-PD-1 antibody or an antigen binding fragment thereof that specifically binds human PD-1. In certain embodiments, the API is a full-length anti-PD-1 antibody selected from any class of immunoglobulins, including IgM, IgG, IgD, IgA, and IgE. Preferably, the antibody is an IgG antibody. Any isotype of IgG can be used, including $IgG_1$, $IgG_2$, $IgG_3$, and $IgG_4$. Different constant domains may be appended to the $V_L$ and $V_H$ regions provided herein. For example, if a particular intended use of an antibody (or fragment) of the invention were to call for altered effector functions, a heavy chain constant domain other than IgG1 may be used. Although IgG1 antibodies provide for long half-life and for effector functions, such as complement activation and antibody-dependent cellular cytotoxicity, such activities may not be desirable for all uses of the antibody. In such instances an IgG4 constant domain, for example, may be used.

In embodiments of the invention, the API is an anti-PD-1 antibody comprising a light chain comprising or consisting of a sequence of amino acid residues as set forth in SEQ ID NO:5 and a heavy chain comprising or consisting of a sequence of amino acid residues as set forth in SEQ ID NO: 10. In alternative embodiments, the API is an anti-PD-1 antibody comprising a light chain comprising or consisting of a sequence of amino acid residues as set forth in SEQ ID NO: 15 and a heavy chain comprising or consisting of a sequence of amino acid residues as set forth in SEQ ID NO:20. In further embodiments, the API is an anti-PD-1 antibody comprising a light chain comprising or consisting of a sequence of amino acid residues as set forth in SEQ ID NO:32 and a heavy chain comprising or consisting of a sequence of amino acid residues as set forth in SEQ ID NO:31. In additional embodiments, the API is an anti-PD-1 antibody comprising a light chain comprising or consisting of a sequence of amino acid residues as set forth in SEQ ID NO:33 and a heavy chain comprising or consisting of a sequence of amino acid residues as set forth in SEQ ID NO:31. In yet additional embodiments, the API is an anti-PD-1 antibody comprising a light chain comprising or consisting of a sequence of amino acid residues as set forth in SEQ ID NO:34 and a heavy chain comprising or consisting of a sequence of amino acid residues as set forth in SEQ ID NO:31. In some formulations of the invention, the API is pembrolizumab or a pembrolizumab biosimilar. In some formulations of the invention, the API is nivolumab or a nivolumab biosimilar.

Ordinarily, amino acid sequence variants of the anti-PD-1 antibodies and antigen binding fragments of the invention will have an amino acid sequence having at least 75% amino acid sequence identity with the amino acid sequence of a reference antibody or antigen binding fragment (e.g. heavy chain, light chain, $V_H$, $V_L$, or humanized sequence), more preferably at least 80%, more preferably at least 85%, more preferably at least 90%, and most preferably at least 95, 98, or 99%. Identity or homology with respect to a sequence is defined herein as the percentage of amino acid residues in the candidate sequence that are identical with the anti-PD-1 residues, after aligning the sequences and introducing gaps, if necessary, to achieve the maximum percent sequence identity, and not considering any conservative substitutions as part of the sequence identity. None of N-terminal, C-terminal, or internal extensions, deletions, or insertions into the antibody sequence shall be construed as affecting sequence identity or homology.

Sequence identity refers to the degree to which the amino acids of two polypeptides are the same at equivalent positions when the two sequences are optimally aligned. Sequence identity can be determined using a BLAST algorithm wherein the parameters of the algorithm are selected to give the largest match between the respective sequences over the entire length of the respective reference sequences. The following references relate to BLAST algorithms often used for sequence analysis: BLAST ALGORITHMS: Altschul, S. F., et al., (1990) J. Mol. Biol. 215:403-410; Gish, W., et al., (1993) *Nature* Genet. 3:266-272; Madden, T. L., et al., (1996) Meth. Enzymol. 266:131-141; Altschul, S. F., et al., (1997) Nucleic Acids Res. 25:3389-3402; Zhang, J., et al., (1997) Genome Res. 7:649-656; Wootton, J. C., et al., (1993) Comput. Chem. 17:149-163; Hancock, J. M. et al., (1994) Comput. Appl. Biosci. 10:67-70; ALIGNMENT SCORING SYSTEMS: Dayhoff, M. O., et al., "A model of evolutionary change in proteins." in Atlas of Protein Sequence and Structure, (1978) vol. 5, suppl. 3. M. O. Dayhoff (ed.), pp. 345-352, Natl. Biomed. Res. Found., Washington, D.C.; Schwartz, R. M., et al., "Matrices for detecting distant relationships." in Atlas of Protein Sequence and Structure, (1978) vol. 5, suppl. 3. "M. O. Dayhoff (ed.), pp. 353-358, Natl. Biomed. Res. Found., Washington, D.C.; Altschul, S. F., (1991) J. Mol. Biol. 219:555-565; States, D. J., et al., (1991) Methods 3:66-70; Henikoff, S., et al., (1992) Proc. Natl. Acad. Sci. USA 89:10915-10919; Altschul, S. F., et al., (1993) J. Mol. Evol. 36:290-300; ALIGNMENT STATISTICS: Karlin, S., et al., (1990) Proc. Natl. Acad. Sci. USA 87:2264-2268; Karlin, S., et al., (1993) Proc. Natl. Acad. Sci. USA 90:5873-5877; Dembo, A., et al., (1994) Ann. Prob. 22:2022-2039; and Altschul, S. F. "Evaluating the statistical significance of multiple distinct local alignments." in Theoretical and Computational Methods in Genome Research (S. Suhai, ed.), (1997) pp. 1-14, Plenum, N.Y.

Likewise, either class of light chain can be used in the compositions and methods herein. Specifically, kappa, lambda, or variants thereof are useful in the present compositions and methods.

TABLE 2

Exemplary PD-1 Antibody Sequences

| Antibody Feature | Amino Acid Sequence | SEQ ID NO. |
|---|---|---|
| *Pembrolizumab Light Chain* | | |
| CDR1 | RASKGVSTSGYSYLH | 1 |
| CDR2 | LASYLES | 2 |
| CDR3 | QHSRDLPLT | 3 |
| Variable Region | EIVLTQSPATLSLSPGERATLSCRASKGVSTSGYSYLHWYQQKPGQAPRLLIYLASYLESGVPARFSGSGSGTDFTLTISSLEPEDFAVYYCQHSRDLPLTFGGGTKVEIK | 4 |
| Light Chain | EIVLTQSPATLSLSPGERATLSCRASKGVSTSGYSYLHWYQQKPGQAPRLLIYLASYLESGVPARFSGSGSGTDFTLTISSLEPEDFAVYYCQHSRDLPLTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 5 |
| *Pembrolizumab Heavy Chain* | | |
| CDR1 | NYYMY | 6 |
| CDR2 | GINPSNGGTNFNEKFKN | 7 |
| CDR3 | RDYRFDMGFDY | 8 |
| Variable Region | QVQLVQSGVEVKKPGASVKVSCKASGYTFTNYYMYWVRQAPGQGLEWMGGINPSNGGTNFNEKFKNRVTLTTDSSTTTAYMELKSLQFDDTAVYYCARRDYRFDMGFDYWGQGTTVTVSS | 9 |
| Heavy Chain | QVQLVQSGVEVKKPGASVKVSCKASGYTFTNYYMYWVRQAPGQGLEWMGGINPSNGGTNFNEKFKNRVTLTTDSSTTTAYMELKSLQFDDTAVYYCARRDYRFDMGFDYWGQGTTVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK | 10 |

TABLE 2-continued

Exemplary PD-1 Antibody Sequences

| Antibody Feature | Amino Acid Sequence | SEQ ID NO. |
|---|---|---|
| *Nivolumab Light Chain* | | |
| CDR1 | RASQSVSSYLA | 11 |
| CDR2 | DASNRAT | 12 |
| CDR3 | QQSSNWPRT | 13 |
| Variable Region | EIVLTQSPATLSLSPGERATLSCRASQSVSSYLAWYQQKPGQAPRLLIYDASNRATGIPARFSGSGSGTDFTLTISSLEPEDFAVYYCQQSSNWPRTFGQGTKVEIK | 14 |
| Light Chain | EIVLTQSPATLSLSPGERATLSCRASQSVSSYLAWYQQKPGQAPRLLIYDASNRATGIPARFSGSGSGTDFTLTISSLEPEDFAVYYCQQSSNWPRTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 15 |
| *Nivolumab Heavy Chain* | | |
| CDR1 | NSGMH | 16 |
| CDR2 | VIWYDGSKRYYADSVKG | 17 |
| CDR3 | NDDY | 18 |
| Variable Region | QVQLVESGGGVVQPGRSLRLDCKASGITFSNSGMHWVRQAPGKGLEWVAVIWYDGSKRYYADSVKGRFTISRDNSKNTLFLQMNSLRAEDTAVYYCATNDDYWGQGTLVTVSS | 19 |
| Heavy Chain | QVQLVESGGGVVQPGRSLRLDCKASGITFSNSGMHWVRQAPGKGLEWVAVIWYDGSKRYYADSVKGRFTISRDNSKNTLFLQMNSLRAEDTAVYYCATNDDYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK | 20 |

TABLE 3

Additional PD-1 Antibodies and Antigen Binding Fragments Useful in the Formulations, Methods and Uses of the Invention.

A. Antibodies and antigen binding fragments comprising light and heavy chain CDRs of hPD-1.08A in WO2008/156712

| | |
|---|---|
| CDRL1 | SEQ ID NO: 21 |
| CDRL2 | SEQ ID NO: 22 |
| CDRL3 | SEQ ID NO: 23 |
| CDRH1 | SEQ ID NO: 24 |
| CDRH2 | SEQ ID NO: 25 |
| CDRH3 | SEQ ID NO: 26 |

TABLE 3-continued

Additional PD-1 Antibodies and Antigen Binding Fragments Useful
in the Formulations, Methods and Uses of the Invention.

C. Antibodies and antigen binding fragments comprising the mature
h109A heavy chain variable region and one of the mature K09A
light chain variable regions in WO 2008/156712

| | |
|---|---|
| Heavy chain VR | SEQ ID NO: 27 |
| Light chain VR | SEQ ID NO: 28 or SEQ ID NO: 29 or SEQ ID NO: 30 |

D. Antibodies and antigen binding fragments comprising the
mature 409 heavy chain and one of the mature K09A light
chains in WO 2008/156712

| | |
|---|---|
| Heavy chain | SEQ ID NO: 31 |
| Light chain | SEQ ID NO: 32 or SEQ ID NO: 33 or SEQ ID NO: 34 |

In some embodiments of the formulations of the invention, the API (i.e. the anti-PD-1 antibody or antigen binding fragment thereof) is present in a concentration of about 25 mg/mL to about 200 mg/mL. In additional embodiments, the API is present in a concentration of from about 5 mg/mL to about 25 mg/mL. In some embodiments of the formulations of the invention, the API (i.e. the anti-PD-1 antibody or antigen binding fragment thereof) is present in a concentration of about 5 mg/mL to about 200 mg/mL. In alternative embodiments, the API is present in a concentration of about 5 mg/mL, about 10 mg/mL, about 25 mg/mL, about 50 mg/mL, about 75 mg/mL, about 100 mg/mL, about 125 mg/mL, about 130 mg/mL about 150 mg/mL, about 165 mg/mL, about 167 mg/mL about 175 mg/mL, about 200 mg/mL.

In one embodiment, the API is present in a concentration of about 165 to about 170 mg/mL.

In one embodiment, the API is present in a concentration of about 167 mg/mL.

In one embodiment, the API is present in a concentration of about 130 mg/mL.

In additional embodiments, the API is present in a concentration of from about 5 mg/mL to about 75 mg/mL, from about 50 mg/mL to about 200 mg/mL; from about 75 mg/mL to about 200 mg/mL; from about 100 mg/mL to about 200 mg/mL; from about 25 mg/mL to about 175 mg/mL; from about 50 mg/mL to about 175 mg/mL; from about 75 mg/mL to about 175 mg/mL; from about 100 mg/mL to about 175 mg/mL; from about 25 mg/mL to about 150 mg/mL; from about 50 mg/mL to about 150 mg/mL; from about 75 mg/mL to about 150 mg/mL; from about 100 mg/mL to about 150 mg/mL; from about 25 mg/mL to about 125 mg/mL; from about 50 mg/mL to about 125 mg/mL; from about 75 mg/mL to about 125 mg/mL; from about 25 mg/mL to about 100 mg/mL, from about 125 mg/mL to about 175 mg/mL, from about 125 mg/mL to about 200 mg/mL, or from about 5 mg/mL to 200 mg/mL.

Formulation Excipients

The formulations of the invention comprise at least one excipient that stabilizes the formulation. In some embodiments, the formulation comprises more than one stabilizer.

In some embodiments of the formulations of the invention, the stabilizer is a non-reducing sugar. In embodiments of the invention, the non-reducing sugar is glucose. In further embodiments, the non-reducing sugar is sucrose. In additional embodiments, the non-reducing sugar is trehalose. In still further embodiments, the non-reducing sugar is lactose. In other embodiments, the non-reducing sugar is raffinose.

In some embodiments, the anti-human PD-1 antibody formulations of the invention comprise a stabilizer selected from the group consisting of: about 6% to about 8% weight/volume (w/v) sucrose, trehalose or (2-hydroxypropyl)-β-cyclodextrin; about 3% to about 5% w/v mannitol, sorbitol, L-arginine, or a pharmaceutically acceptable salt of L-arginine, or L-proline, or a pharmaceutically acceptable salt of L-proline; and about 1.8 to about 2.2% w/v glycine, or a pharmaceutically acceptable salt thereof.

In some embodiments, the stabilizer is about 6% to about 8% w/v sucrose.

In some embodiments, the stabilizer is about 6% to about 8% w/v trehalose.

In some embodiments, the stabilizer is about 6% to about 8% w/v (2-hydroxypropyl)-β-cyclodextrin.

In some embodiments, the stabilizer is sucrose, trehalose or (2-hydroxypropyl)-3-cyclodextrin, which is present in an amount of about 6% to about 8% w/v. In further embodiments, the sucrose, trehalose or (2-hydroxypropyl)-β-cyclodextrin is present in an amount of about 6.5% to about 7.5% w/v. In still further embodiments, the sucrose, trehalose or (2-hydroxypropyl)-β-cyclodextrin is present in an amount of about 6% w/v, about 6.25% w/v, about 6.5% w/v, about 6.75% w/v, about 7% w/v, about 7.25% w/v, about 7.5% w/v, about 7.75% w/v or about 8% w/v.

In some embodiments, the stabilizer is about 3% to about 5% w/v mannitol.

In some embodiments, the stabilizer is about 3% to about 5% w/v sorbitol.

In some embodiments, the stabilizer is about 3% to about 5% w/v L-arginine, or a pharmaceutically acceptable salt thereof.

In certain embodiments, the formulation of the invention comprises arginine, e.g., L-arginine or a pharmaceutically acceptable salt thereof. In additional embodiments, the formulations of the invention comprise arginine hydrochloride (i.e. arginine HCl). In further embodiments, the formulations comprise arginine succinate. In further embodiments, the arginine is L-arginine.

In some embodiments, the stabilizer is about 3% to about 5% w/v proline, e.g., L-proline, or a pharmaceutically acceptable salt thereof. In additional embodiments, the formulations of the invention comprise proline hydrochloride (i.e. proline HCl). In further embodiments, the formulations comprise L-proline.

In some embodiments, the stabilizer is mannitol, sorbitol, L-arginine, a pharmaceutically acceptable salt of L-arginine, L-proline, or a pharmaceutically acceptable salt of L-proline, which is present in an amount of about 3% to about 5% w/v. In further embodiments, the mannitol, sorbitol, L-arginine, pharmaceutically acceptable salt of L-arginine, L-proline, or a pharmaceutically acceptable salt of L-proline, is present in an amount of about 3.5% to about 4.5% w/v. In still further embodiments, the mannitol, sorbitol, L-arginine, pharmaceutically acceptable salt of L-arginine, L-proline, or pharmaceutically acceptable salt of L-proline, is present in an amount of about 3% w/v, about 3.25% w/v, about 3.5% w/v, about 3.75% w/v, about 4% w/v, about 4.25% w/v, about 4.5% w/v, about 4.75% w/v, or about 5% w/v.

In some embodiments, the stabilizer is about 1.8 to about 2.2% w/v glycine, or a pharmaceutically acceptable salt thereof.

In certain embodiments, the formulation of the invention comprises glycine or a pharmaceutically acceptable salt thereof. In additional embodiments, the formulations of the invention comprise sodium glycinate.

In specific embodiments, the stabilizer is glycine, which is present in an amount of about 150 mM to about 200 mM, or about 150 mM, about 160 mM, about 170 mM, about 175 mM, about 180 mM, about 190 mM or about 200 mM.

In certain embodiments, the stabilizer is glycine, which is present in an amount of about 1.8 to about 2.2% w/v, about 1.5 to about 2.5%, or about 1.8 to about 2.5% or about 1.5 to about 2.2%. In specific embodiments, the glycine is present in an amount of about 1.8%, about 2.0% about 2.2%, or about 2.5%.

In some embodiments, the anti-human PD-1 antibody formulations of the invention comprise a stabilizer selected from the group consisting of (1) about 6% to about 8% w/v sucrose, trehalose or (2-hydroxypropyl)-β-cyclodextrin; (2) about 3% to about 5% mannitol, sorbitol, L-proline, or a pharmaceutically acceptable salt of L-proline; and (3) about 1.8 to about 2.2% w/v glycine, or a pharmaceutically acceptable salt thereof.

The formulations of the invention optionally comprise arginine, e.g., L-arginine, or a pharmaceutically acceptable salt thereof, which may provide additional stability to the formulation, as well as control viscosity, which allows formulation at high API concentration. In some embodiments of the invention, the L-arginine or pharmaceutically acceptable salt is present in the formulations in an amount of 0.25% to about 3% weight/volume. In additional embodiments, the L-arginine or pharmaceutically acceptable salt is present in an amount of about 0.25% w/v, about 0.50% w/v, about 0.75% w/v, about 1.0% w/v, about 1.25% w/v, about 1.5% w/v, about 1.75% w/v, about 2.0% w/v, about 2.25% w/v, about 2.5% w/v, about 2.75% w/v or about 3.0% w/v. In further embodiments, the L-arginine or pharmaceutically acceptable salt is present in an amount of about 0 to about 2.75% w/v, 0 to about 2.5% w/v, 0 to about 2.25% w/v, 0 to about 2% w/v, 0 to about 1.75% w/v, 0 to about 1.5% w/v, 0 to about 1.25% w/v, 0 to about 1.0% w/v, about 0.5% to about 3.0% w/v, about 0.5% to about 2.75% w/v, about 0.5% to about 2.5% w/v, about 0.5% to about 2.25% w/v, about 0.5% to about 2% w/v, about 0.5% to about 1.75% w/v, about 0.5% to about 1.5% w/v, about 0.5% to about 1.25% w/v, about 0.5% to about 1.0% w/v, about 1.0% to about 3.0% w/v, about 1.0% to about 2.75% w/v, about 1.0% to about 2.5% w/v, about 1.0% to about 2.25% w/v, about 1.0% to about 2% w/v, about 1.0% to about 1.75% w/v, 1.0% to about 1.5% w/v, about 1.5% to about 3.0% w/v, about 1.5% to about 2.75% w/v, about 1.5% to about 2.5% w/v, about 1.5% to about 2.25% w/v, about 1.5% to about 2% w/v, or about 2% to about 3% w/v.

In some embodiments of the invention, the stabilizer is selected from the group consisting of: about 6% to about 8% w/v sucrose, trehalose or (2-hydroxypropyl)-β-cyclodextrin; about 3% to about 5% w/v mannitol, sorbitol, or proline, or a pharmaceutically acceptable salt thereof; and about 1.8 to about 2.2% w/v glycine, or a pharmaceutically acceptable salt thereof, and the formulation further comprises L-arginine or a pharmaceutically acceptable salt thereof, which can be added in any of the amounts above to reduce viscosity of the formulation, especially when the API is present in high concentration (e.g. 75 mg/mL-200 mg/mL). It is understood that although L-arginine, or pharmaceutically acceptable salt thereof, may be added to reduce viscosity in such embodiments, the L-arginine or pharmaceutically acceptable salt, may also be serving to stabilize the formulation and may impart additional stability relative to the formulation without L-arginine or pharmaceutically acceptable salt.

As noted above, in specific embodiments, the formulations of the invention comprise a high concentration of API (e.g. about 75 mg/mL to about 200 mg/mL). In particular embodiments wherein a high concentration of API is employed, the formulations of the invention also comprise arginine, e.g., L-arginine, or a pharmaceutically acceptable salt thereof, e.g. an amount of L-arginine from about 0.25% to about 3.0% w/v.

In addition to an anti-PD-1 antibody or antigen binding fragment thereof, and a stabilizer in the amounts/concentrations specified above, the formulations of the invention also comprise a buffer. In some embodiments the buffer is present in an amount of about 5 mM to about 20 mM, which provides for a pH in the range of about 4.5 to 6.4.

In some embodiments of the invention, the buffer provides the formulation a pH in the range from about 4.5 to about 6.5. In further embodiments, the buffer has a pH in a range of about 5.0 to about 6.0. In still further embodiments, the pH is from about 5.3 to about 5.8. In other embodiments, the pH is from about 6.0 to about 6.4.

In particular embodiments, the buffer has a pH of about 5.0, about 5.1, about 5.2, about 5.3, about 5.4, about 5.5, about 5.6, about 5.7, about 5.8, about 5.9, about 6.0, about 6.2 or about 6.4. Examples of buffers that will control the pH in this range include succinate (sodium or potassium), histidine, sodium acetate, phosphate (sodium or potassium), Tris (tris (hydroxymethyl)aminomethane), diethanolamine, citrate (sodium) and other organic acid buffers.

In specific embodiments of the invention, the buffer is histidine or acetate at a pH of about 5.0 to about 6.0. In some embodiments, the buffer is an L-histidine buffer. In some preferred embodiments, the buffer is acetate. In embodiments where the formulation is lyophilized, it is preferred that the buffer is not acetate because acetate buffer systems are not compatible with the lyophilization process.

When a range of pH values is recited, such as "a pH between pH 5.5 and 6.0," the range is intended to be inclusive of the recited values. Unless otherwise indicated, for lyophilized formula the pH refers to the pH after reconstitution of the lyophilized formulations of the invention. The pH is typically measured at 25° C. using standard glass bulb pH meter. As used herein, a solution comprising "histidine buffer at pH X" refers to a solution at pH X and comprising the histidine buffer, i.e. the pH is intended to refer to the pH of the solution.

In addition to an anti-PD-1 antibody or antigen binding fragment thereof, a stabilizer, and a buffer in the amounts/concentrations specified above, the formulations of the invention also comprise an anti-oxidant. In embodiments of the invention, the anti-oxidant is methionine. In embodiments of the invention, the anti-oxidant is L-methionine, or a pharmaceutically acceptable salt thereof. In further embodiments, the methionine is L-methionine. In other embodiments, the anti-oxidants is L-methionine HCl. In other embodiments, the anti-oxidant is histidine.

In some embodiments, the anti-oxidant (e.g. L-methionine) is present in the formulations of the invention in an amount of amount 1 mM to about 20 mM. In further embodiments, the anti-oxidant is present in an amount of about 5 mM to about 20 mM, about 5 mM to about 15 mM, about 5 mM to about 10 mM. In additional embodiments, the anti-oxidant is present in an amount of about 1 mM, about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM or about 20 mM.

In embodiments wherein the anti-oxidant is histidine, the histidine can be present in amounts up to 100 mM. In such embodiments, histidine can serve as a buffer and as an anti-oxidant in the formulations of the invention.

In addition to an anti-PD-1 antibody or antigen binding fragment thereof, a stabilizer, a buffer, and an anti-oxidant in the amounts/concentrations specified above, the formulations of the invention also comprise a surfactant. Surfactants are typically added to formulations to provide stability, reduce and/or prevent aggregation or to prevent and/or inhibit protein damage during processing conditions such as purification, filtration, freeze-drying, transportation, storage, and delivery. In some embodiments of the invention, a surfactant is useful for providing additional stability to the active ingredient(s), i.e. the anti-PD-1 antibody or antigen binding fragment thereof.

Surfactants that may be useful in the formulations of the invention include, but are not limited to: nonionic surfactants such as polyoxyethylene sorbitan fatty acid esters (Polysorbates, sold under the trade name Tween® (Uniquema Americas LLC, Wilmington, Del.)) including Polysorbate-20 (polyoxyethylene sorbitan monolaurate), Polysorbate-40 (polyoxyethylene sorbitan monopalmitate), Polysorbate-60 (polyoxyethylene sorbitan monostearate), and Polysorbate-80 (polyoxyethylene sorbitan monooleate); polyoxyethylene alkyl ethers such as Brij® 58 (Uniquema Americas LLC, Wilmington, Del.) and Brij® 35; poloxamers (e.g., poloxamer 188); Triton® X-100 (Union Carbide Corp., Houston, Tex.) and Triton® X-114; NP40; Span 20, Span 40, Span 60, Span 65, Span 80 and Span 85; copolymers of ethylene and propylene glycol (e.g., the Pluronic® series of nonionic surfactants such as Pluronic® F68, Pluronic® 10R5, Pluronic® F108, Pluronic® F127, Pluronic® F38, Pluronic® L44, Pluronic® L62 (BASF Corp., Ludwigshafen, Germany); and sodium dodecyl sulfate (SDS).

The amount of surfactant to be included in the formulations of the invention is an amount sufficient to perform the desired function, i.e. a minimal amount necessary to stabilize the active pharmaceutical ingredient (i.e. the anti-PD-1 antibody or antigen binding fragment thereof) in the formulation. Typically, the surfactant is present in a concentration of from about 0.008% to about 0.1% w/v % w/v. In some embodiments of this aspect of the invention, the surfactant is present in the formulation in an amount from about 0.01% to about 0.04%; from about 0.01% to about 0.03%, from about 0.01% to about 0.02%, from about 0.015% to about 0.04%; from about 0.015% to about 0.03%, from about 0.015% to about 0.02%, from about 0.02% to about 0.04%, from about 0.02% to about 0.035%, or from about 0.02% to about 0.03%. In specific embodiments, the surfactant is present in an amount of about 0.02%. In alternative embodiments, the surfactant is present in an amount of about 0.01%, about 0.015%, about 0.025%, about 0.03%, about 0.035%, or about 0.04%.

In exemplary embodiments of the invention, the surfactant is a nonionic surfactant selected from the group consisting of: Polysorbate 20, Polysorbate 80 and F127. In preferred embodiments, the surfactant is Polysorbate 80.

In specific embodiments, the PD-1 formulations of the invention comprise about 0.01% to about 0.04% PS80. In further embodiments, the formulations of the invention comprise PS80 in an amount of about 0.008%, about 0.01%, about 0.015%, about 0.02%, about 0.025%, about 0.03%, about 0.035%, about 0.04% or about 0.045%. In particular embodiments, the formulations of the invention comprise about 0.02% PS80.

The invention also provides an anti-human PD-1 antibody formulation as described herein, wherein the formulation is contained in a glass vial or injection device (e.g. a syringe).

In embodiments of the formulations of the invention, the anti-human PD-1 antibody formulation has one or more of the following attributes after storage at 2-8° C. for 12 months:
  a) the % heavy chain and light chain as measured by reducing CE-SDS is ≥90.0%,
  b) the % intact IgG as measured by non-reducing CE-SDS is ≥90.0%, and
  c) the % monomer as measured by HP-SEC is ≥95%.

In further embodiments, the invention provides anti-human PD-1 antibody formulations as described herein, wherein after storage of the formulation at 2-8° C. for 12 months, the % heavy chain and light chain measured by reducing CE-SDS is ≥96%.

In further embodiments, the invention provides anti-human PD-1 antibody formulations as described herein, wherein after storage of the formulation at 2-8° C. for 12 months the % intact IgG in the formulation measured by non-reducing CE-SDS is ≥97%.

In further embodiments, the invention provides anti-human PD-1 antibody formulations as described herein, wherein after storage of the formulation at 2-8° C. for 12 months, the % monomer as measured by HP-SEC is ≥98.5.

In additional embodiments, the invention provides anti-human PD-1 antibody formulations as described herein, wherein after storage of the formulation at 2-8° C. for 12 months, the % high molecular weight species as measured by HP-SEC is ≤1.5%.

In further embodiments, the invention provides anti-human PD-1 antibody formulations as described herein, wherein after storage of the formulation at 25° C. for 12 months, the % monomer as measured by HP-SEC is ≥98.0%.

In additional embodiments, the invention provides anti-human PD-1 antibody formulations as described herein, wherein after storage of the formulation at 25° C. for 6 months, the % high molecular weight species as measured by HP-SEC is ≤2%.

In further embodiments, the invention provides anti-human PD-1 antibody formulations as described herein, wherein after storage of the formulation at 40° C. for 3 months, the % monomer as measured by HP-SEC is ≥94.0%, ≥94.5% or ≥95.0%.

In additional embodiments, the invention provides anti-human PD-1 antibody formulations as described herein, wherein after storage of the formulation at 40° C. for 3 months, the % high molecular weight species as measured by HP-SEC is ≤5.5%, ≤5.0%, or ≤4.4%.

Specific Aspects and Embodiments of the Invention

In one aspect (A1), the invention provides an anti-human PD-1 antibody formulation, comprising: (a) about 5 mg/mL to about 200 mg/mL of an anti-human PD-1 antibody, or antigen binding fragment thereof; (b) about 5 mM to about 20 mM buffer; (c) a stabilizer selected from the group consisting of: (i) about 6% to about 8% weight/volume (w/v) sucrose, trehalose or (2-hydroxypropyl)-β-cyclodextrin; (ii) about 3% to about 5% w/v mannitol, sorbitol, L-arginine, a pharmaceutically acceptable salt of L-arginine, L-proline, or a pharmaceutically acceptable salt of L-proline; and (iii) about 1.8 to about 2.2% w/v glycine, or a pharmaceutically acceptable salt thereof; (d) about 0.01% to about 0.10% non-ionic surfactant; and (e) about 1 mM to about 20 mM anti-oxidant.

In one embodiment of aspect (A1), formulation has a pH between 4.5 and 6.4.

In one embodiment of aspect (A1), formulation has a pH between 5.0 and 6.0.

In one embodiment of aspect (A1), formulation has a pH between 5.3 and 5.8.

In one embodiment of aspect (A1), formulation has a pH around 5.5.

In one embodiment of aspect (A1), the buffer is histidine or acetate.

In one embodiment of aspect (A1), the buffer is about 10 mM histidine.

In one embodiment of aspect (A1), the buffer is about 10 mM L-histidine.

In one embodiment of aspect (A1), the buffer is about 10 mM acetate.

In one embodiment of aspect (A1), the stabilizer is about 6% to about 8% w/v sucrose.

In one embodiment of aspect (A1), the stabilizer is about 6% to about 8% w/v trehalose.

In one embodiment of aspect (A1), the stabilizer is about 6% to about 8% w/v (2-hydroxypropyl)-β-cyclodextrin.

In one embodiment of aspect (A1), the stabilizer is about 3% to about 5% w/v mannitol.

In one embodiment of aspect (A1), the stabilizer is about 3% to about 5% w/v sorbitol.

In one embodiment of aspect (A1), the stabilizer is about 3% to about 5% w/v L-arginine, or a pharmaceutically acceptable salt thereof.

In one embodiment of aspect (A1), the stabilizer is about 3% to about 5% w/v L-arginine, or a pharmaceutically acceptable salt thereof, and the pH of the formulation is from about 6.0 to about 6.4.

In one embodiment of aspect (A1), the stabilizer is about 3% to about 5% w/v L-arginine.

In one embodiment of aspect (A1), the stabilizer is about 3% to about 5% w/v arginine-HCl.

In one embodiment of aspect (A1), the stabilizer is about 3% to about 5% w/v L-proline, or a pharmaceutically acceptable salt thereof.

In one embodiment of aspect (A1), the stabilizer is about 3% to about 5% w/v L-proline.

In one embodiment of aspect (A1), the stabilizer is about 3% to about 5% w/v L-proline HCl.

In one embodiment of aspect (A1), the stabilizer is about 160 mM to about 200 mM glycine, or a pharmaceutically acceptable salt thereof.

In one embodiment of aspect (A1), the stabilizer is about 1.8 to about 2.2% w/v glycine, or pharmaceutically acceptable salt thereof.

In one embodiment of aspect (A1), the non-ionic surfactant is about 0.01% to about 0.04% polysorbate 80.

In one embodiment of aspect (A1), the non-ionic surfactant is about 0.02% polysorbate 80.

In one embodiment of aspect (A1), the anti-oxidant is about 1 mM to about 20 mM L-methionine or a pharmaceutically acceptable salt thereof.

In one embodiment of aspect (A1), the anti-oxidant is about 5 mM to about 15 mM L-methionine or a pharmaceutically acceptable salt thereof.

In one embodiment of aspect (A1), the anti-oxidant is about 10 mM L-methionine or a pharmaceutically acceptable salt thereof.

In one embodiment of aspect (A1), the anti-oxidant is L-methionine.

In one aspect (A2), the invention provides an anti-human PD-1 antibody formulation, comprising: (a) about 5 mg/mL to about 200 mg/mL of an anti-human PD-1 antibody, or antigen binding fragment thereof; (b) about 5 mM to about 20 mM buffer; (c) a stabilizer selected from the group consisting of: (i) about 6% to about 8% weight/volume (w/v) sucrose, trehalose or (2-hydroxypropyl)-β-cyclodextrin; (ii) about 3% to about 5% w/v mannitol, sorbitol, L-proline, or a pharmaceutically acceptable salt of L-proline; and (iii) about 1.8 to about 2.2% w/v glycine, or a pharmaceutically acceptable salt thereof; (d) about 0.01% to about 0.10% non-ionic surfactant; and (e) about 1 mM to about 20 mM anti-oxidant.

In one embodiment of aspect (A2), the formulation further comprises from about 1% to about 3% w/v L-arginine, or a pharmaceutically acceptable salt thereof.

In one aspect (A3), the invention provides an anti-human PD-1 antibody formulation comprising: (a) about 25 mg/mL to about 200 mg/mL of an anti-human PD-1 antibody, or antigen binding fragment thereof; (b) about 5 mM to about 20 mM histidine buffer; (c) about 6% to about 8% w/v sucrose; (d) about 0.01% to about 0.04% w/v polysorbate 80; and (e) about 1 mM to about 20 mM L-methionine, or a pharmaceutically acceptable salt thereof.

In one embodiment of aspect (A3), the formulation further comprises from about 1% to about 3% w/v L-arginine, or a pharmaceutically acceptable salt thereof.

In one embodiment of aspect (A3), the formulation further comprises from about 1.25% to about 2.5% w/v L-arginine, or a pharmaceutically acceptable salt thereof.

In one embodiment of aspect (A3), the histidine buffer is present at a concentration of about 8 mM to about 12 mM.

In one embodiment of aspect (A3), the histidine buffer is L-histidine.

In one embodiment of aspect (A3), the L-methionine or pharmaceutically acceptable salt is present at a concentration of about 5 mM to about 15 mM.

In one embodiment of aspect (A3), the polysorbate 80 is present at a weight ratio of approximately 0.02% w/v.

In one embodiment of aspect (A3), the sucrose is present at a weight ratio of approximately 7% w/v.

In one aspect (A4), the invention provides an anti-human PD-1 antibody formulation, comprising: (a) about 75 to about 200 mg/mL of an anti-human PD-1 antibody, or antigen binding fragment thereof; (b) about 8 mM to about 12 mM histidine buffer; (c) about 5 mM to about 10 mM L-methionine, or a pharmaceutically acceptable salt thereof; (d) about 6% to about 8% w/v sucrose; and (e) 0.01% to about 0.04% w/v polysorbate 80.

In one aspect (A5), the invention provides an anti-human PD-1 antibody formulation, comprising: (a) about 125 to about 200 mg/mL of an anti-human PD-1 antibody, or antigen binding fragment thereof; (b) about 10 mM histidine buffer; (c) about 10 mM L-methionine or pharmaceutically acceptable salt thereof; (d) about 7% w/v sucrose; and (e) about 0.02% to w/v polysorbate 80.

In one embodiment of aspect (A5), the formulation further comprises from about 1.25% to about 2.5% w/v L-arginine, or a pharmaceutically acceptable salt thereof.

In one embodiment of aspect (A5), the formulation further comprises from about 1.25% to about 2.5% w/v L-arginine.

In one embodiment of aspect (A5), the formulation further comprises from about 1.25% to about 2.5% w/v L-arginine-HCl.

In one embodiment of aspect (A5), the formulation has a pH between 5.0 and 6.0.

In one embodiment of aspect (A5), the formulation has a pH between 5.3 and 5.8.

In one aspect (A6), the invention provides an anti-human PD-1 antibody formulation, comprising: (a) about 5 mg/mL to about 75 mg/mL of an anti-human PD-1 antibody, or antigen binding fragment thereof; (b) about 8 mM to about 12 mM histidine buffer; (c) a stabilizer selected from the group consisting of: (i) about 6% to about 8% weight/volume (w/v) sucrose, trehalose or (2-hydroxypropyl)-β-cyclodextrin; (ii) about 3% to about 5% w/v mannitol, sorbitol, L-arginine, a pharmaceutically acceptable salt of L-arginine, L-proline, or a pharmaceutically acceptable salt of L-proline; and (iii) about 1.8 to about 2.2% w/v glycine, or a pharmaceutically acceptable salt thereof; (d) about 0.01% to about 0.04% polysorbate 80; and (e) about 5 mM to about 10 mM L-methionine or a pharmaceutically acceptable salt thereof.

In one embodiment of aspect (A6), the anti-human PD-1 antibody, or antigen binding fragment thereof is present at a concentration of about 5 mg/mL to about 25 mg/mL.

In one aspect (A7), the invention provides an anti-human PD-1 antibody formulation, comprising: (a) about 5 mg/mL to about 75 mg/mL of an anti-human PD-1 antibody, or antigen binding fragment thereof; (b) about 8 mM to about 12 mM histidine buffer; (c) about 6% to about 8% weight/volume w/v sucrose; (d) about 0.01% to about 0.04% polysorbate 80; and (e) about 5 mM to about 10 mM L-methionine or a pharmaceutically acceptable salt thereof.

In one embodiment of aspect (A7), the anti-human PD-1 antibody, or antigen binding fragment thereof is present at a concentration of about 5 mg/mL to about 25 mg/mL.

In one embodiment of aspect (A7), the L-methionine or a pharmaceutically acceptable salt thereof is L-methionine-HCl.

In one aspect (A8), the invention provides an anti-human PD-1 antibody formulation, comprising: (a) about 5 mg/mL to about 75 mg/mL of an anti-human PD-1 antibody, or antigen binding fragment thereof; (b) about 8 mM to about 12 mM histidine buffer; (c) about 6% to about 8% w/v trehalose; (d) about 0.01% to about 0.04% polysorbate 80; and (e) about 5 mM to about 10 mM methionine or a pharmaceutically acceptable salt thereof.

In one embodiment of aspect (A8), the anti-human PD-1 antibody, or antigen binding fragment thereof is present at a concentration of about 5 mg/mL to about 25 mg/mL.

In one aspect (A9), the invention provides an anti-human PD-1 antibody formulation, comprising: (a) about 5 mg/mL to about 75 mg/mL of an anti-human PD-1 antibody, or antigen binding fragment thereof; (b) about 8 mM to about 12 mM histidine buffer; (c) about 6% to about 8% w/v (2-hydroxypropyl)-β-cyclodextrin; (d) about 0.01% to about 0.04% polysorbate 80; and (e) about 5 mM to about 10 mM L-methionine or a pharmaceutically acceptable salt thereof.

In one embodiment of aspect (A9), the anti-human PD-1 antibody, or antigen binding fragment thereof is present at a concentration of about 5 mg/mL to about 25 mg/mL.

In one aspect (A10), the invention provides an anti-human PD-1 antibody formulation, comprising: (a) about 5 mg/mL to about 75 mg/mL of an anti-human PD-1 antibody, or antigen binding fragment thereof; (b) about 8 mM to about 12 mM histidine buffer; (c) about 3% to about 5% w/v mannitol; (d) about 0.01% to about 0.04% polysorbate 80; and (e) about 5 mM to about 10 mM L-methionine or a pharmaceutically acceptable salt thereof.

In one embodiment of aspect (A10), the anti-human PD-1 antibody, or antigen binding fragment thereof is present at a concentration of about 5 mg/mL to about 25 mg/mL.

In one aspect (A11), the invention provides an anti-human PD-1 antibody formulation, comprising: (a) about 5 mg/mL to about 75 mg/mL of an anti-human PD-1 antibody, or antigen binding fragment thereof; (b) about 8 mM to about 12 mM histidine buffer; (c) about 3% to about 5% w/v sorbitol; (d) about 0.01% to about 0.04% polysorbate 80; and (e) about 5 mM to about 10 mM L-methionine or a pharmaceutically acceptable salt thereof.

In one embodiment of aspect (A11), the anti-human PD-1 antibody, or antigen binding fragment thereof is present at a concentration of about 5 mg/mL to about 25 mg/mL.

In one aspect (A12), the invention provides an anti-human PD-1 antibody formulation, comprising: (a) about 5 mg/mL to about 75 mg/mL of an anti-human PD-1 antibody, or antigen binding fragment thereof; (b) about 8 mM to about 12 mM histidine buffer; (c) about 3% to about 5% w/v L-proline, or a pharmaceutically acceptable salt thereof; (d) about 0.01% to about 0.04% polysorbate 80; and (e) about 5 mM to about 10 mM L-methionine or a pharmaceutically acceptable salt thereof.

In one embodiment of aspect (A12), the anti-human PD-1 antibody, or antigen binding fragment thereof is present at a concentration of about 5 mg/mL to about 25 mg/mL.

In one embodiment of aspect (A12), the L-proline, or a pharmaceutically acceptable salt thereof is L-proline.

In one embodiment of aspect (A12), the L-proline, or a pharmaceutically acceptable salt thereof is L-proline HCl.

In one aspect (A13), the invention provides an anti-human PD-1 antibody formulation, comprising: (a) about 5 mg/mL to about 75 mg/mL of an anti-human PD-1 antibody, or antigen binding fragment thereof; (b) about 8 mM to about 12 mM histidine buffer; (c) about 3% to about 5% w/v L-arginine, or a pharmaceutically acceptable salt thereof; (d) about 0.01% to about 0.04% polysorbate 80; and (e) about 5 mM to about 10 mM L-methionine or a pharmaceutically acceptable salt thereof.

In one embodiment of aspect (A13), the anti-human PD-1 antibody, or antigen binding fragment thereof is present at a concentration of about 5 mg/mL to about 25 mg/mL.

In one embodiment of aspect (A13), the pH of the formulation is about 6.0 to about 6.4.

In one embodiment of aspect (A13), the L-arginine, or a pharmaceutically acceptable salt thereof is L-arginine.

In one embodiment of aspect (A13), the L-arginine, or a pharmaceutically acceptable salt thereof is L-arginine HCl.

In one aspect (A14), the invention provides an anti-human PD-1 antibody formulation, comprising: (a) about 5 mg/mL to about 75 mg/mL of an anti-human PD-1 antibody, or antigen binding fragment thereof; (b) about 8 mM to about 12 mM histidine buffer; (c) about 160 mM to about 200 mM glycine, or a pharmaceutically acceptable salt thereof; (d) about 0.01% to about 0.04% polysorbate 80; and (e) about 5 mM to about 10 mM L-methionine or a pharmaceutically acceptable salt thereof.

In one embodiment of aspect (A14), the anti-human PD-1 antibody, or antigen binding fragment thereof is present at a concentration of about 5 mg/mL to about 25 mg/mL.

In one embodiment of aspect (A14), the glycine, or pharmaceutically acceptable salt thereof is glycine.

In one embodiment of aspect (A14), the glycine, or pharmaceutically acceptable salt thereof is glycine HCl.

In one embodiment of aspect (A14), the glycine, or pharmaceutically acceptable salt thereof is glycine succinate.

In one embodiment of any of aspects (A6)-(A14), the formulation further comprises a metal chelator.

In one embodiment of any of aspects (A6)-(A14), the formulation further comprises DTPA, which is present at a concentration of about 10 µM to about 3 µM.

In some embodiments of any of aspects (A1)-(A14), the formulation is a liquid.

In some embodiments of any of aspects (A1)-(A14), the formulation is a reconstituted solution from a lyophilized formulation.

In any of the specific aspects and embodiments described herein, any anti-PD-1 antibody or antigen binding fragment thereof (i.e. an antibody or antigen binding fragment that specifically binds human PD-1, e.g. pembrolizumab or an antigen-binding fragment thereof) can be used. In particular embodiments, one of the anti-PD-1 antibodies, or antigen binding fragments thereof, described herein, e.g. described in the section entitled Anti-PD-1 Antibodies and Antigen-Binding Fragments Thereof, is used.

In some embodiments of the invention, any of the formulations described herein is in aqueous solution. In alternative embodiment, the invention provides lyophilized formulations made by lyophilizing an aqueous formulation to provide a reconstituted formulation of the invention, as discussed more fully, infra.

Lyophilized Pharmaceutical Compositions

Lyophilized formulations of therapeutic proteins provide several advantages.

Lyophilized formulations in general offer better chemical stability than solution formulations, and thus increased half-life. A lyophilized formulation may also be reconstituted at different concentrations depending on clinical factors, such as route of administration or dosing. For example, a lyophilized formulation may be reconstituted at a high concentration (i.e. in a small volume) if necessary for subcutaneous administration, or at a lower concentration if administered intravenously. High concentrations may also be necessary if high dosing is required for a particular subject, particularly if administered subcutaneously where injection volume must be minimized. One such lyophilized antibody formulation is disclosed at U.S. Pat. No. 6,267,958, which is hereby incorporated by reference in its entirety. Lyophilized formulations of another therapeutic protein are disclosed at U.S. Pat. No. 7,247,707, which is hereby incorporated by reference in its entirety.

Typically, the lyophilized formulation is prepared in anticipation of reconstitution at high concentration of drug product (DP, in an exemplary embodiment humanized anti-PD-1 antibody pembrolizumab, or antigen binding fragment thereof), i.e. in anticipation of reconstitution in a low volume of water. Subsequent dilution with water or isotonic buffer can then readily be used to dilute the DP to a lower concentration. Typically, excipients are included in a lyophilized formulation of the invention at levels that will result in a roughly isotonic formulation when reconstituted at high DP concentration, e.g. for subcutaneous administration. Reconstitution in a larger volume of water to give a lower DP concentration will necessarily reduce the tonicity of the reconstituted solution, but such reduction may be of little significance in non-subcutaneous, e.g. intravenous, administration. If isotonicity is desired at lower DP concentration, the lyophilized powder may be reconstituted in the standard low volume of water and then further diluted with isotonic diluent, such as 0.9% sodium chloride.

In an embodiment of the invention, humanized anti-PD-1 antibody (or antigen binding fragment thereof) is formulated as a lyophilized powder for reconstituting and utilizing for intravenous administration. In certain embodiments, the antibody (or antigen binding fragment thereof) is provided at about 50 mg/vial, and is reconstituted with sterile water for injection prior to use. If desired, the reconstituted antibody may be aseptically diluted with 0.9% sodium chloride Injection USP in a sterile IV container. In some embodiments, the target pH of the reconstituted formulation is 5.5±0.5. In various embodiments, the lyophilized formulation of the invention enables reconstitution of the anti-PD-1 antibody to high concentrations, such as about 20, 25, 30, 40, 50, 60, 75, 100, 125, 150, 175 or more mg/mL.

Lyophilized formulations are by definition essentially dry, and thus the concept of concentration is not useful in describing them. Describing a lyophilized formulation in the terms of the weight of the components in a unit dose vial is more useful, but is problematic because it varies for different doses or vial sizes. In describing the lyophilized formulations of the invention, it is useful to express the amount of a component as the ratio of the weight of the component compared to the weight of the drug substance (DS) in the same sample (e.g. a vial). This ratio may be expressed as a percentage. Such ratios reflect an intrinsic property of the lyophilized formulations of the invention, independent of vial size, dosing, and reconstitution protocol.

In other embodiments, the lyophilized formulation of anti-human PD-1 antibody, or antigen binding fragment, is defined in terms of the pre-lyophilization solution used to make the lyophilized formulation, such as the pre-lyophilization solution. In one embodiment the pre-lyophilization solution comprises antibody, or antigen-binding fragment thereof, at a concentration of about 10 mg/mL about 25 mg/mL or about 50 mg/mL. Such pre-lyophilization solutions may be at pH 4.4-5.2 (including about 4.4, 4.5, 4.6, 4.7, 4.8, 4.9, 5.0, 5.1, and 5.2), e.g. preferably about pH 4.8, or about pH 5.5.

In yet other embodiments, the lyophilized formulation of anti-human PD-1 antibody, or antigen binding fragment, is defined in terms of the reconstituted solution generated from the lyophilized formulation.

Reconstituted solutions may comprise antibody, or antigen-binding fragment thereof, at concentrations of about 10, 15, 20, 25, 30, 40, 50, 60, 75, 80, 90 or 100 mg/mL or higher concentrations such as 150 mg/mL, 167 mg/mL, 200 mg/mL, or up to about 250 mg/mL. Such reconstituted solutions may be at about pH 5.5, or range from about pH 5.0 to about 6.0

The lyophilized formulations of the invention are formed by lyophilization (freeze-drying) of a pre-lyophilization solution. Freeze-drying is accomplished by freezing the formulation and subsequently subliming water at a temperature suitable for primary drying. Under this condition, the product temperature is below the eutectic point or the collapse temperature of the formulation. Typically, the shelf temperature for the primary drying will range from about −30 to 25° C. (provided the product remains frozen during primary drying) at a suitable pressure, ranging typically from about 50 to 250 mTorr. The formulation, size and type of the container holding the sample (e.g., glass vial) and the volume of liquid will dictate the time required for drying, which can range from a few hours to several days (e.g. 40-60 hrs). A secondary drying stage may be carried out at about 0-40° C., depending primarily on the type and size of container and the type of protein employed. The secondary drying time is dictated by the desired residual moisture level in the product and typically takes at least about 5 hours. Typically, the moisture content of a lyophilized formulation is less than about 5%, and preferably less than about 3%. The pressure may be the same as that employed during the primary drying step. Freeze-drying conditions can be varied depending on the formulation and vial size.

In some instances, it may be desirable to lyophilize the protein formulation in the container in which reconstitution of the protein is to be carried out in order to avoid a transfer step. The container in this instance may, for example, be a 3, 5, 10, 20, 50 or 100 cc vial.

The lyophilized formulations of the invention are reconstituted prior to administration. The protein may be reconstituted at a concentration of about 10, 15, 20, 25, 30, 40, 50, 60, 75, 80, 90 or 100 mg/mL or higher concentrations such as 150 mg/mL, 200 mg/mL, 250 mg/mL, or 300 mg/mL up to about 500 mg/mL. High protein concentrations are particularly useful where subcutaneous delivery of the reconstituted formulation is intended. However, for other routes of administration, such as intravenous administration, lower concentrations of the protein may be desired (e.g. from about 5-50 mg/mL).

Reconstitution generally takes place at a temperature of about 25° C. to ensure complete hydration, although other temperatures may be employed as desired. The time required for reconstitution will depend, e.g., on the type of diluent, amount of excipient(s) and protein. Exemplary diluents include sterile water, bacteriostatic water for injection (BWFI), a pH buffered solution (e.g. phosphate-buffered saline), sterile saline solution, Ringer's solution or dextrose solution.

The invention provides a liquid anti-human PD-1 antibody formulation that is reconstituted from a lyophilized formulation wherein the reconstituted solution comprises: a) about 125 mg/mL to about 175 mg/mL of an anti-human PD-1 antibody, or antigen binding fragment thereof; b) about 8 mM to about 12 mM histidine buffer; c) a stabilizer selected from the group consisting of: (i) about 3% to about 8% weight/volume (w/v) sucrose; (ii) about 2% to about 5% w/v L-arginine, or a pharmaceutically acceptable salt thereof; (iii) about 3% to about 5% mannitol and about 1% to about 2% sucrose, and (iv) a combination of i) and ii); and d) about 0.01% to about 0.04% polysorbate 80.

In embodiments of the invention, the stabilizer comprises about 3% to about 8% weight/volume (w/v) sucrose.

In embodiments of the invention, the stabilizer comprises about 2% to about 5% w/v L-arginine, or a pharmaceutically acceptable salt thereof.

In embodiments of the invention, the stabilizer comprises about 3% to about 5% mannitol and about 1% to about 2% sucrose.

In embodiments of the invention, the stabilizer comprises about 4% to about 4.5% mannitol and about 1% to about 2% sucrose.

In embodiments of the invention, the stabilizer comprises about 3% to about 8% weight/volume (w/v) sucrose and about 2% to about 5% w/v L-arginine, or a pharmaceutically acceptable salt thereof. In specific embodiments, the stabilizer comprises sucrose and L-arginine. In other embodiments, the stabilizer comprises sucrose and L-arginine-HCl.

In specific embodiments, the stabilizer comprises a combination of 2-4% w/v L-arginine, or a pharmaceutically acceptable salt thereof and 3.5-6% w/v sucrose. In other embodiments, the stabilizer comprises a combination of about 3% L-arginine or a pharmaceutically acceptable salt thereof and about 5.5% sucrose. In other embodiments, the stabilizer comprises a combination of about 2% L-arginine or a pharmaceutically acceptable salt thereof and about 5% sucrose. In other embodiments, the stabilizer comprises a combination of about 2% L-arginine or a pharmaceutically acceptable salt thereof and about 3.7% sucrose.

Liquid Pharmaceutical Compositions

A liquid antibody formulation can be made by taking the drug substance (e.g., anti-humanized PD-1) which is in liquid form (e.g., pembrolizumab in an aqueous pharmaceutical formulation) and buffer exchanging it into the desired buffer as the last step of the purification process. There is no lyophilization step in this embodiment. The drug substance in the final buffer is concentrated to a desired concentration. Excipients such as sucrose, methionine and polysorbate 80 are added to the drug substance and it is diluted using the appropriate buffer to final protein concentration. The final formulated drug substance is filtered, e.g. using 0.22 µm filters, and filled into a final container (e.g. glass vials or syringes). Such a liquid formulation is exemplified by a final liquid formulation comprising 10 mM histidine pH 5.5, 7% sucrose, 0.02% polysorbate 80, 25-200 mg/mL pembrolizumab and 1.5-2.5% arginine, or a pharmaceutically acceptable salt thereof.

III. Methods of Use

The invention also relates to a method of treating cancer in a subject, the method comprising administering an effective amount of any of the formulations of the invention; i.e., any formulation described herein (including the formulations of the invention defined as aspects (A1)-(A14) in the Specific Aspects and Embodiments of the Invention section herein (referred to hereafter as "aspects (A1)-(A14)")), to the subject. In some embodiments of this method, the formulation is administered to the subject via intravenous administration. In other embodiments, the formulation is administered to the subject by subcutaneous administration.

In any of the methods of the invention, the cancer can be selected from the group consisting of: melanoma, lung cancer, head and neck cancer, bladder cancer, breast cancer, gastrointestinal cancer, multiple myeloma, hepatocellular cancer, lymphoma, renal cancer, mesothelioma, ovarian cancer, esophageal cancer, anal cancer, biliary tract cancer, colorectal cancer, cervical cancer, thyroid cancer, salivary cancer, prostate cancer (e.g. hormone refractory prostate adenocarcinoma), pancreatic cancer, colon cancer, esophageal cancer, liver cancer, thyroid cancer, glioblastoma, glioma, and other neoplastic malignancies.

In some embodiments the lung cancer in non-small cell lung cancer.

In alternate embodiments, the lung cancer is small-cell lung cancer.

In some embodiments, the lymphoma is Hodgkin lymphoma.

In other embodiments, the lymphoma is non-Hodgkin lymphoma. In particular embodiments, the lymphoma is mediastinal large B-cell lymphoma. In some embodiments, the lymphoma is diffuse large B-cell lymphoma (DLBCL).

In some embodiments, the breast cancer is triple negative breast cancer.

In further embodiments, the breast cancer is ER+/HER2− breast cancer.

In some embodiments, the bladder cancer is urothelial cancer.

In some embodiments, the head and neck cancer is nasopharyngeal cancer. In some embodiments, the cancer is thyroid cancer. In other embodiments, the cancer is salivary cancer. In other embodiments, the cancer is squamous cell carcinoma of the head and neck.

In some embodiments, the cancer is metastatic colorectal cancer with high levels of microsatellite instability (MSI-H).

In some embodiments, the cancer is a solid tumor with a high level of microsatellite instability (MSI-H).

In some embodiments, the cancer is a solid tumor with a high mutational burden.

In some embodiments, the cancer is selected from the group consisting of: melanoma, non-small cell lung cancer, relapsed or refractory classical Hodgkin lymphoma, head and neck squamous cell carcinoma, urothelial cancer, esophageal cancer, gastric cancer, DLBCL and hepatocellular cancer.

In other embodiments of the above treatment methods, the cancer is a Heme malignancy. In certain embodiments, the Heme malignancy is acute lymphoblastic leukemia (ALL), acute myeloid leukemia (AML), chronic lymphocytic leukemia (CLL), chronic myeloid leukemia (CML), DLBCL, EBV-positive DLBCL, primary mediastinal large B-cell lymphoma, T-cell/histiocyte-rich large B-cell lymphoma, follicular lymphoma, Hodgkin's lymphoma (HL), mantle cell lymphoma (MCL), multiple myeloma (MM), myeloid cell leukemia-1 protein (Mcl-1), myelodysplastic syndrome (MDS), non-Hodgkin lymphoma (NHL), or small lymphocytic lymphoma (SLL).

Malignancies that demonstrate improved disease-free and overall survival in relation to the presence of tumor-infiltrating lymphocytes in biopsy or surgical material, e.g. melanoma, colorectal, liver, kidney, stomach/esophageal, breast, pancreas, and ovarian cancer are encompassed in the methods and treatments described herein. Such cancer subtypes are known to be susceptible to immune control by T lymphocytes. Additionally, included are refractory or recurrent malignancies whose growth may be inhibited using the antibodies described herein.

In some embodiments, the formulations of the invention (e.g. aspects (A1)-(A14)) are administered to a subject having a cancer characterized by elevated expression of PD-L1 and/or PD-L2 in tested tissue samples, including: ovarian, renal, colorectal, pancreatic, breast, liver, gastric, esophageal cancers and melanoma. Additional cancers that can benefit from treatment with anti-PD-1 antibodies such as humanized anti-PD-1 antibody pembrolizumab include those associated with persistent infection with viruses such as human immunodeficiency viruses, hepatitis viruses class A, B and C, Epstein Barr virus, human papilloma viruses that are known to be causally related to for instance Kaposi's sarcoma, liver cancer, nasopharyngeal cancer, lymphoma, cervical, vulval, anal, penile and oral cancers.

In one embodiment, the invention comprises a method of treating cancer in a human patient comprising administering any formulation of the invention (e.g. aspects (A1)-(A14)) to the patient.

In one embodiment, the invention comprises a method of treating unresectable or metastatic melanoma in a human patient comprising administering any formulation of the invention (e.g. aspects (A1)-(A14)) to the patient.

In one embodiment, the invention comprises a method of treating metastatic non-small cell lung cancer (NSCLC) in a human patient comprising administering a formulation of the invention (e.g. aspects (A1)-(A14)) to the patient. In specific embodiments, the patient has a tumor with high PD-L1 expression [(Tumor Proportion Score (TPS)≥50%)] and was not previously treated with platinum-containing chemotherapy. In other embodiments, the patient has a tumor with PD-L1 expression (TPS≥1%) and was previously treated with platinum-containing chemotherapy. In still other embodiments, the patient has a tumor with PD-L1 expression (TPS≥1%) and was not previously treated with platinum-containing chemotherapy. In specific embodiments, the patient had disease progression on or after receiving platinum-containing chemotherapy.

In certain embodiments, the PD-L1 TPS is determined by an FDA-approved test.

In certain embodiments, the patient's tumor has no EGFR or ALK genomic aberrations.

In certain embodiments, the patient's tumor has an EGFR or ALK genomic aberration and had disease progression on or after receiving treatment for the EGFR or ALK aberration(s) prior to receiving the anti-PD-1 antibody, or antigen binding fragment thereof.

In one embodiment, the invention comprises a method of treating metastatic non-small cell lung cancer (NSCLC) in a human patient comprising: (1) administering a formulation of the invention (e.g. aspects (A1)-(A14)) to the patient, and (2) administering pemetrexed and carboplatin to the patient. In specific embodiments, the patient was not previously treated with an anti-cancer therapeutic prior to starting the combination treatment regimen with the formulation of the invention, pemetrexed and carboplatin.

In a certain embodiments, the patient has nonsquamous non-small cell lung cancer.

In certain embodiments, pemetrexed is administered to the patient in an amount of 500 mg/m$^2$. In sub-embodiments, pemetrexed is administered to the patient via intravenous infusion every 21 days. In specific embodiments, the infusion time is about 10 minutes.

In embodiments of the invention where the patient is treated with a formulation of the invention in combination with pemetrexed, the invention further comprises administering about 400 μg to about 1000 μg of folic acid to the patient once per day, beginning about 7 days prior to administering pemetrexed to the patient and continuing until about 21 days after the patient is administered the last dose of pemetrexed. In certain embodiments the folic acid is administered orally. In some embodiments, the invention further comprises administering about 1 mg of vitamin $B_{12}$ to the patient about 1 week prior to the first administration of pemetrexed and about every three cycles of pemetrexed administration (i.e., approximately every 9 weeks). In certain embodiments the vitamin $B_{12}$ is administered intramuscularly. In certain embodiments, the invention further comprises administering about 4 mg of dexamethasone to the patient twice a day on the day before, the day of, and the day after pemetrexed administration. In certain embodiments the dexamethasone is administered orally.

In one embodiment, the invention comprises a method of treating recurrent or metastatic head and neck squamous cell cancer (HNSCC) in a human patient comprising administering any formulation of the invention (e.g. aspects (A1)-(A14)) to the patient. In certain embodiments, the patient was previously treated with platinum-containing chemotherapy. In certain embodiments, the patient had disease progression on or after platinum-containing chemotherapy.

In one embodiment, the invention comprises a method of treating refractory classical Hodgkin lymphoma (cHL) in a human patient comprising administering a formulation of the invention (e.g. aspects (A1)-(A14)) to the patient. In certain embodiments, the patient has relapsed after 3 or more lines of therapy for cHL. In specific embodiments, the patient is an adult patient. in alternative embodiments, the patient is a pediatric patient.

In one embodiment, the invention comprises a method of treating locally advanced or metastatic urothelial carcinoma in a human patient comprising administering a formulation of the invention (e.g. aspects (A1)-(A14)) to the patient. In certain embodiments, the patient is not eligible for cisplatin-containing chemotherapy. In certain embodiments, the patient has disease progression during or following platinum-containing chemotherapy or within 12 months of neoadjuvant or adjuvant treatment with platinum-containing chemotherapy.

In one embodiment, the invention comprises a method of treating unresectable or metastatic, microsatellite instability-high (MSI-H) or mismatch repair deficient solid tumors in a human patient comprising administering a formulation of the invention (e.g. aspects (A1)-(A14)) to the patient. In specific embodiments, the patient had disease progression following prior anti-cancer treatment.

In one embodiment, the invention comprises a method of treating unresectable or metastatic, microsatellite instability-high (MSI-H) or mismatch repair deficient colorectal cancer in a human patient comprising administering a formulation of the invention (e.g. aspects (A1)-(A14)) to the patient. In specific embodiments, the patient had disease progression following prior treatment with a fluoropyrimidine, oxaliplatin, and irinotecan.

In one embodiment, the invention comprises a method of treating recurrent locally advanced or metastatic gastric cancer in a human patient comprising administering a formulation of the invention (e.g. aspects (A1)-(A14)) to the patient.

In one embodiment, the invention comprises a method of treating recurrent locally advanced or metastatic gastroesophageal junction adenocarcinoma in a human patient comprising administering a formulation of the invention (e.g. aspects (A1)-(A14)) to the patient. In specific embodiments, the patient's tumor expresses PD-L1 [Combined Positive Score (CPS)≥1]. In specific embodiments, the patient has disease progression on or after two or more prior lines of therapy including fluoropyrimidine- and platinum-containing chemotherapy. In specific embodiments, the patient has disease progression on or after two or more prior lines of therapy including HER2/neu-targeted therapy.

In one embodiment, the invention comprises a method of treating cancer in a human patient comprising administering a formulation of the invention (e.g. aspects (A1)-(A14)) to the patient, wherein the patient has a cancer selected from the group consisting of: melanoma, lung cancer, head and neck cancer, bladder cancer, breast cancer, gastrointestinal cancer, multiple myeloma, hepatocellular cancer, lymphoma, renal cancer, mesothelioma, ovarian cancer, esophageal cancer, anal cancer, biliary tract cancer, colorectal cancer, cervical cancer, thyroid cancer, and salivary cancer.

In one embodiment, the invention comprises a method of treating small cell lung cancer in a human patient comprising administering a formulation of the invention (e.g. aspects (A1)-(A14)) to the patient.

In one embodiment, the invention comprises a method of treating non-Hodgkin lymphoma in a human patient comprising administering a formulation of the invention (e.g. aspects (A1)-(A14)) to the patient. In specific embodiments, the non-Hodgkin lymphoma is mediastinal large B-cell lymphoma. In specific embodiments, the non-Hodgkin lymphoma is diffuse large B-cell lymphoma.

In one embodiment, the invention comprises a method of treating breast cancer in a human patient comprising administering a formulation of the invention (e.g. aspects (A1)-(A14)) to the patient. In certain embodiments, the breast cancer is triple negative breast cancer. In certain embodiments, the breast cancer is ER+/HER2− breast cancer.

In one embodiment, the invention comprises a method of treating nasopharyngeal cancer in a human patient comprising administering a formulation of the invention (e.g. aspects (A1)-(A14)) to the patient.

In one embodiment, the invention comprises a method of treating thyroid cancer in a human patient comprising administering a formulation of the invention (e.g. aspects (A1)-(A14)) to the patient.

In one embodiment, the invention comprises a method of treating salivary cancer in a human patient comprising administering a formulation of the invention (e.g. aspects (A1)-(A14)) to the patient.

Antagonist anti-PD-1 antibodies or antibody fragments can also be used to prevent or treat infections and infectious disease. Thus, the invention provides a method for treating chronic infection in a mammalian subject comprising administering an effective amount of a formulation of the invention to the subject. In some specific embodiments of this method, the formulation is administered to the subject via intravenous administration. In other embodiments, the formulation is administered to the subject by subcutaneous administration.

These agents can be used alone, or in combination with vaccines, to stimulate the immune response to pathogens, toxins, and self-antigens. The antibodies or antigen-binding fragment thereof can be used to stimulate immune response to viruses infectious to humans, including but not limited to: human immunodeficiency viruses, hepatitis viruses class A, B and C, Epstein Barr virus, human cytomegalovirus, human papilloma viruses, and herpes viruses. Antagonist anti-PD-1 antibodies or antibody fragments can be used to stimulate immune response to infection with bacterial or fungal parasites, and other pathogens. Viral infections with hepatitis B and C and HIV are among those considered to be chronic viral infections.

The formulations of the invention may be administered to a patient in combination with one or more "additional therapeutic agents". The additional therapeutic agent may be a biotherapeutic agent (including but not limited to antibodies to VEGF, EGFR, Her2/neu, VEGF receptors, other growth factor receptors, CD20, CD40, CD-40L, OX-40, 4-1BB, and ICOS), a growth inhibitory agent, an immunogenic agent (for example, attenuated cancerous cells, tumor antigens, antigen presenting cells such as dendritic cells pulsed with tumor derived antigen or nucleic acids, immune stimulating cytokines (for example, IL-2, IFNα2, GM-CSF), and cells transfected with genes encoding immune stimulating cytokines such as but not limited to GM-CSF).

As noted above, in some embodiments of the methods of the invention, the method further comprises administering an additional therapeutic agent. In particular embodiments, the additional therapeutic agent is an anti-LAG3 antibody or antigen binding fragment thereof, an anti-GITR antibody, or antigen binding fragment thereof, an anti-TIGIT antibody, or antigen binding fragment thereof, an anti-CD27 antibody or antigen binding fragment thereof. In one embodiment, the additional therapeutic agent is a Newcastle disease viral vector expressing IL-12. In a further embodiment, the additional therapeutic agent is dinaciclib. In still further embodiments, the additional therapeutic agent is a STING agonist.

Suitable routes of administration may, for example, include parenteral delivery, including intramuscular, subcutaneous, as well as intrathecal, direct intraventricular, intravenous, intraperitoneal. Drugs can be administered in a variety of conventional ways, such as intraperitoneal, parenteral, intraarterial or intravenous injection. Modes of administration in which the volume of solution must be limited (e.g. subcutaneous administration) require a lyophilized formulation to enable reconstitution at high concentration.

Selecting a dosage of the additional therapeutic agent depends on several factors, including the serum or tissue turnover rate of the entity, the level of symptoms, the immunogenicity of the entity, and the accessibility of the target cells, tissue or organ in the individual being treated. The dosage of the additional therapeutic agent should be an amount that provides an acceptable level of side effects. Accordingly, the dose amount and dosing frequency of each additional therapeutic agent (e.g. biotherapeutic or chemotherapeutic agent) will depend in part on the particular therapeutic agent, the severity of the cancer being treated, and patient characteristics. Guidance in selecting appropriate doses of antibodies, cytokines, and small molecules are available. See, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, N.Y.; Bach (ed.) (1993) *Monoclonal Antibodies and Peptide Therapy in Autoimmune Diseases*, Marcel Dekker, New York, N.Y.; Baert et al. (2003) *New Engl. J. Med.* 348:601-608; Milgrom et al. (1999) *New Engl. J. Med.* 341:1966-1973; Slamon et al. (2001) *New Engl. J. Med.* 344:783-792; Beniaminovitz et al. (2000) *New Engl. J. Med.* 342:613-619; Ghosh et al. (2003) *New Engl. J. Med.* 348:24-32; Lipsky et al. (2000) *New Engl. J. Med.* 343:1594-1602; Physicians' Desk Reference 2003 (Physicians' Desk Reference, 57th Ed); Medical Economics Company; ISBN: 1563634457; 57th edition (November 2002). Determination of the appropriate dosage regimen may be made by the clinician, e.g., using parameters or factors known or suspected in the art to affect treatment or predicted to affect treatment, and will depend, for example, the patient's clinical history (e.g., previous therapy), the type and stage of the cancer to be treated and biomarkers of response to one or more of the therapeutic agents in the combination therapy.

Various literature references are available to facilitate selection of pharmaceutically acceptable carriers or excipients for the additional therapeutic agent. See, e.g., *Remington's Pharmaceutical Sciences and U.S. Pharmacopeia: National Formulary*, Mack Publishing Company, Easton, Pa. (1984); Hardman et al. (2001) *Goodman and Gilman's The Pharmacological Basis of Therapeutics*, McGraw-Hill, New York, N.Y.; Gennaro (2000) *Remington: The Science and Practice of Pharmacy*, Lippincott, Williams, and Wilkins, New York, N.Y.; Avis et al. (eds.) (1993) *Pharmaceutical Dosage Forms: Parenteral Medications*, Marcel Dekker, N.Y.; Lieberman, et al. (eds.) (1990) *Pharmaceutical Dosage Forms: Tablets*, Marcel Dekker, N.Y.; Lieberman et al. (eds.) (1990) *Pharmaceutical Dosage Forms: Disperse Systems*, Marcel Dekker, N.Y.; Weiner and Kotkoskie (2000) *Excipient Toxicity and Safety*, Marcel Dekker, Inc., New York, N.Y.

A pharmaceutical antibody formulation can be administered by continuous infusion, or by doses at intervals of, e.g., one day, 1-7 times per week, one week, two weeks, three weeks, monthly, bimonthly, etc. A preferred dose protocol is one involving the maximal dose or dose frequency that avoids significant undesirable side effects. A total weekly dose is generally at least 0.05 µg/kg, 0.2 µg/kg, 0.5 µg/kg, 1 µg/kg, 10 µg/kg, 100 µg/kg, 0.2 µg/kg, 1.0 mg/kg, 2.0 mg/kg, 10 mg/kg, 25 mg/kg, 50 mg/kg body weight or more. See, e.g., Yang et al. (2003) *New Engl. J. Med.* 349:427-434; Herold et al. (2002) *New Engl. J. Med.* 346:1692-1698; Liu et al. (1999)*J. Neurol. Neurosurg. Psych.* 67:451-456; Portielji et al. (20003) *Cancer Immunol. Immunother.* 52:133-144. The desired dose of a small molecule therapeutic, e.g., a peptide mimetic, natural product, or organic chemical, is about the same as for an antibody or polypeptide, on a moles/kg basis.

In certain embodiments, dosing will comprise administering to a subject escalating doses of 1.0, 3.0, and 10 mg/kg of the pharmaceutical formulation, i.e, a formulation comprising pembrolizumab, over the course of treatment. The formulation comprising pembrolizumab can be a reconstituted liquid formulation, or it can be a liquid formulation not previously lyophilized. Time courses can vary, and can continue as long as desired effects are obtained. In certain embodiments, dose escalation will continue up to a dose of about 10 mg/kg. In certain embodiments, the subject will have a histological or cytological diagnosis of melanoma, or other form of solid tumor, and in certain instances, a subject may have non-measurable disease. In certain embodiments, the subject will have been treated with other chemotherapeutics, while in other embodiments, the subject will be treatment naïve.

In yet additional embodiments, the dosing regimen will comprise administering a dose of 1, 3, or 10 mg/kg of any of the pharmaceutical formulations described herein (i.e, a formulation comprising pembrolizumab), throughout the course of treatment. For such a constant dosing regimen, the interval between doses will be about 14 days (±2 days). In certain embodiments, the interval between doses will be about 21 days (±2 days).

In certain embodiments, the dosing regimen will comprise administering a dose of from about 0.005 mg/kg to about 10 mg/kg, with intra-patient dose escalation. In certain embodiments, a dose of 5 mg/kg or 10 mg/kg will be administered at intervals of every 3 weeks, or every 2 weeks. In yet additional embodiments, a dose of 3 mg/kg will be administered at three week intervals for melanoma patients or patients with other solid tumors. In these embodiments, patients should have non-resectable disease; however, patients may have had previous surgery.

In certain embodiments, a subject will be administered a 30 minute IV infusion of any of the pharmaceutical formulations described herein. In certain embodiments for the escalating dose, the dosing interval will be about 28 days ((±1 day) between the first and second dose. In certain embodiments, the interval between the second and third doses will be about 14 days (±2 days). In certain embodiments, the dosing interval will be about 14 days (±2 days), for doses subsequent to the second dose.

In certain embodiments, the use of cell surface markers and/or cytokine markers, as described in WO2012/018538 or WO2008/156712 will be used in bioassays for monitoring, diagnostic, patient selection, and/or treatment regimens involving blockade of the PD-1 pathway.

Subcutaneous administration may performed by injected using a syringe, or using other injection devices (e.g. the Inject-Ease® device); injector pens; or needleless devices (e.g. MediJector and BioJector®).

Embodiments of the invention also include one or more of the biological formulations described herein (i) for use in, (ii) for use as a medicament or composition for, or (iii) for use in the preparation of a medicament for: (a) therapy (e.g., of the human body); (b) medicine; (c) induction of or increasing of an antitumor immune response (d) decreasing the number of one or more tumor markers in a patient; (e) halting or delaying the growth of a tumor or a blood cancer; (f) halting or delaying the progression of PD-1-related disease; (g) halting or delaying the progression cancer; (h)

stabilization of PD-1-related disease; (i) inhibiting the growth or survival of tumor cells; (j) eliminating or reducing the size of one or more cancerous lesions or tumors; (k) reduction of the progression, onset or severity of PD-1-related disease; (l) reducing the severity or duration of the clinical symptoms of PD-1-related disease such as cancer (m) prolonging the survival of a patient relative to the expected survival in a similar untreated patient n) inducing complete or partial remission of a cancerous condition or other PD-1 related disease, or o) treatment of cancer.

General Methods

Standard methods in molecular biology are described Sambrook, Fritsch and Maniatis (1982 & 1989 $2^{nd}$ Edition, 2001 $3^{rd}$ Edition) *Molecular Cloning, A Laboratory Manual*, Cold Spring Harbor Laboratory Press, Cold Spring Harbor, N.Y.; Sambrook and Russell (2001) *Molecular Cloning, $3^{rd}$ ed.*, Cold Spring Harbor Laboratory Press, Cold Spring Harbor, N.Y.; Wu (1993) *Recombinant DNA*, Vol. 217, Academic Press, San Diego, Calif.). Standard methods also appear in Ausbel, et al. (2001) *Current Protocols in Molecular Biology*, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science*, Vol. 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science*, Vol. 2, John Wiley and Sons, Inc., New York; Ausubel, et al. (2001) *Current Protocols in Molecular Biology*, Vol. 3, John Wiley and Sons, Inc., NY, NY, pp. 16.0.5-16.22.17; Sigma-Aldrich, Co. (2001) *Products for Life Science Research*, St. Louis, Mo.; pp. 45-89; Amersham Pharmacia Biotech (2001) BioDirectory, Piscataway, N.J., pp. 384-391). Production, purification, and fragmentation of polyclonal and monoclonal antibodies are described (Coligan, et al. (2001) *Current Protocols in Immunology*, Vol. 1, John Wiley and Sons, Inc., New York; Harlow and Lane (1999) *Using Antibodies*, Cold Spring Harbor Laboratory Press, Cold Spring Harbor, N.Y.; Harlow and Lane, supra). Standard techniques for characterizing ligand/receptor interactions are available (see, e.g., Coligan, et al. (2001) *Current Protocols in Immunology*, Vol. 4, John Wiley, Inc., New York).

Monoclonal, polyclonal, and humanized antibodies can be prepared (see, e.g., Sheperd and Dean (eds.) (2000) *Monoclonal Antibodies*, Oxford Univ. Press, New York, N.Y.; Kontermann and Dubel (eds.) (2001) *Antibody Engineering*, Springer-Verlag, New York; Harlow and Lane (1988) *Antibodies A Laboratory Manual*, Cold Spring Harbor Laboratory Press, Cold Spring Harbor, N.Y., pp. 139-243; Carpenter, et al. (2000) *J. Immunol*. 165:6205; He, et al. (1998) *J. Immunol*. 160:1029; Tang et al. (1999) *J. Biol. Chem*. 274:27371-27378; Baca et al. (1997)*J. Biol. Chem*. 272:10678-10684; Chothia et al. (1989) *Nature* 342:877-883; Foote and Winter (1992) *J. Mol. Biol*. 224:487-499; U.S. Pat. No. 6,329,511).

An alternative to humanization is to use human antibody libraries displayed on phage or human antibody libraries in transgenic mice (Vaughan et al. (1996) *Nature* Biotechnol. 14:309-314; Barbas (1995) *Nature Medicine* 1:837-839; Mendez et al. (1997) *Nature Genetics* 15:146-156; Hoogenboom and Chames (2000) *Immunol. Today* 21:371-377; Barbas et al. (2001) *Phage Display: A Laboratory Manual*, Cold Spring Harbor Laboratory Press, Cold Spring Harbor, N.Y.; Kay et al. (1996) *Phage Display of Peptides and Proteins: A Laboratory Manual*, Academic Press, San Diego, Calif.; de Bruin et al. (1999) *Nature Biotechnol*. 17:397-399).

Purification of antigen is not necessary for the generation of antibodies. Animals can be immunized with cells bearing the antigen of interest. Splenocytes can then be isolated from the immunized animals, and the splenocytes can fused with a myeloma cell line to produce a hybridoma (see, e.g., Meyaard et al. (1997) *Immunity* 7:283-290; Wright et al. (2000) *Immunity* 13:233-242; Preston et al., supra; Kaithamana et al. (1999) *J. Immunol*. 163:5157-5164).

Antibodies can be conjugated, e.g., to small drug molecules, enzymes, liposomes, polyethylene glycol (PEG). Antibodies are useful for therapeutic, diagnostic, kit or other purposes, and include antibodies coupled, e.g., to dyes, radioisotopes, enzymes, or metals, e.g., colloidal gold (see, e.g., Le Doussal et al. (1991) *J. Immunol*. 146:169-175; Gibellini et al. (1998) *J. Immunol*. 160:3891-3898; Hsing and Bishop (1999) *J. Immunol*. 162:2804-2811; Everts et al. (2002) *J. Immunol*. 168:883-889).

Methods for flow cytometry, including fluorescence activated cell sorting (FACS), are available (see, e.g., Owens, et al. (1994) *Flow Cytometry Principles for Clinical Laboratory Practice*, John Wiley and Sons, Hoboken, N.J.; Givan (2001) *Flow Cytometry*, $2^{nd}$ ed.; Wiley-Liss, Hoboken, N.J.; Shapiro (2003) *Practical Flow Cytometry*, John Wiley and Sons, Hoboken, N.J.). Fluorescent reagents suitable for modifying nucleic acids, including nucleic acid primers and probes, polypeptides, and antibodies, for use, e.g., as diagnostic reagents, are available (Molecular Probesy (2003) *Catalogue*, Molecular Probes, Inc., Eugene, Oreg.; Sigma-Aldrich (2003) *Catalogue*, St. Louis, Mo.).

Standard methods of histology of the immune system are described (see, e.g., Muller-Harmelink (ed.) (1986) *Human Thymus: Histopathology and Pathology*, Springer Verlag, New York, N.Y.; Hiatt, et al. (2000) *Color Atlas of Histology*, Lippincott, Williams, and Wilkins, Phila, Pa.; Louis, et al. (2002) *Basic Histology: Text and Atlas*, McGraw-Hill, New York, N.Y.).

Software packages and databases for determining, e.g., antigenic fragments, leader sequences, protein folding, functional domains, glycosylation sites, and sequence alignments, are available (see, e.g., GenBank, Vector NTI® Suite (Informax, Inc, Bethesda, Md.); GCG Wisconsin Package (Accelrys, Inc., San Diego, Calif.); DeCypher® (TimeLogic Corp., Crystal Bay, Nev.); Menne, et al. (2000) *Bioinformatics* 16: 741-742; Menne, et al. (2000) *Bioinformatics Applications Note* 16:741-742; Wren, et al. (2002) *Comput. Methods Programs Biomed*. 68:177-181; von Heijne (1983) *Eur. J. Biochem*. 133:17-21; von Heijne (1986) *Nucleic Acids Res*. 14:4683-4690).

Analytical Methods

Analytical methods suitable for evaluating the product stability include size exclusion chromatography (SEC), dynamic light scattering test (DLS), differential scanning calorimetery (DSC), iso-asp quantification, potency, UV at 340 nm, UV spectroscopy, and FTIR. SEC (J. Pharm. Scien., 83:1645-1650, (1994); Pharm. Res., 11:485 (1994); J. Pharm. Bio. Anal., 15:1928 (1997); J. Pharm. Bio. Anal., 14:1133-1140 (1986)) measures percent monomer in the product and gives information of the amount of soluble aggregates. DSC (Pharm. Res., 15:200 (1998); Pharm. Res., 9:109 (1982)) gives information of protein denaturation temperature and glass transition temperature. DLS (American Lab., November (1991)) measures mean diffusion coefficient, and gives information of the amount of soluble and insoluble aggregates. UV at 340 nm measures scattered light intensity at 340 nm and gives information about the amounts of soluble and insoluble aggregates. UV spectroscopy measures absorbance at 278 nm and gives information of protein concentration. FTIR (Eur. J. Pharm. Biopharm., 45:231 (1998); Pharm. Res., 12:1250 (1995); J. Pharm. Scien., 85:1290 (1996); J. Pharm. Scien., 87:1069 (1998)) measures IR spectrum in the amide one region, and gives information of protein secondary structure.

The iso-asp content in the samples is measured using the Isoquant Isoaspartate Detection System (Promega). The kit uses the enzyme Protein Isoaspartyl Methyltransferase (PIMT) to specifically detect the presence of isoaspartic acid residues in a target protein. PIMT catalyzes the transfer of a methyl group from S-adenosyl-L-methionine to isoaspartic acid at the .alpha.-carboxyl position, generating S-adenosyl-L-homocysteine (SAH) in the process. This is a relatively small molecule, and can usually be isolated and quantitated by reverse phase HPLC using the SAH HPLC standards provided in the kit.

The potency or bioidentity of an antibody can be measured by its ability to bind to its antigen. The specific binding of an antibody to its antigen can be quantitated by any method known to those skilled in the art, for example, an immunoassay, such as ELISA (enzyme-linked immunosorbant assay).

All publications mentioned herein are incorporated by reference for the purpose of describing and disclosing methodologies and materials that might be used in connection with the invention.

Having described different embodiments of the invention herein with reference to the accompanying drawings, it is to be understood that the invention is not limited to those precise embodiments, and that various changes and modifications may be effected therein by one skilled in the art without departing from the scope or spirit of the invention as defined in the appended claims.

Example 1

Materials and Methods

CE-SDS:

Samples were analyzed by a CE-SDS technique in which protein was denatured with sodium dodecyl sulfate (SDS) under reducing and non-reducing conditions and separated using capillary electrophoresis (CE) (Beckman-Coulter ProteomeLab PA800 CE system and IgG Purity/Heterogeneity Assay Kit). The method separates proteins based on their apparent molecular weight. Under non-reducing conditions, all species other than the main IgG peak were classified as impurities. Under reducing conditions, the IgG was resolved into the heavy and light chains. All other species were classified as impurities. In both cases, the result was reported as corrected area percent of each peak as calculated from the total corrected peak area percent.

HP-IEX:

High performance ion-exchange chromatography (HP-IEX) was used to assess the charge profile. An ion exchange HPLC method was performed using a Dionex Dionex ProPac WCX-10 column and a UV detector at 280 nm. Samples were diluted in purified water, and 80 μg were injected for analysis. The mobile phase used for the IEX analysis was a gradient of the following mobile phases (mobile phase A: 24 mM MES, pH 6, 4% acetonitrile (v/v); mobile phase B: 20 mM phosphate, 95 mM NaCl, pH 8, 4% acetonitrile (v/v). The main peak is the major component of the chromatogram and it serves as a control for the characterization of acidic and basic variants. Acidic variants elute earlier than main peak and the main cause of the formation of acidic variants is due to the deamidation of the Asn in main peak and the presence of sialic acid compared to main peak. Basic variants elute later than main peak and the main cause of the formation of basic variants is due to the incomplete removal of C-terminal Lys from the main peak. Other causes are incomplete cyclization of the N-terminal glutamine (Gln) to pyroGlu of the light chain or heavy chain or both and also due to the Isomerization of Asp in the main peak to isoAsp.

HP-SEC:

Purity of the sample was assessed by size exclusion chromatography (SEC) in which the percentage of monomer was determined, as well as the percentages of high molecular weight species (HMW) and late eluting peaks (LMW species). The presence of HMW species indicates protein aggregates and the presence of LMW species indicate protein fragments. High Performance-Size Exclusion Chromatography (HP-SEC) was performed by diluting the samples to 1.0 mg/mL with water. The diluted samples were injected (10 μL) into a HPLC equipped with a YMC-pack-Diol 200 column and a UV detector. Proteins in the sample were separated by size and detected by UV absorption at 280 nm.

HP-SEC Arg:

Purity of the sample was assessed by size exclusion chromatography (SEC) in which the percentage of monomer was determined, as well as the percentages of high molecular weight species (HMW) and late eluting peaks (LMW species). High Performance-Size Exclusion Chromatography (HP-SEC) was performed by diluting the samples to 5.0 mg/mL in mobile phase (50 mM sodium phosphate, 450 mM arginine mono hydrochloride, pH 7.0). The column temperature was set at 25° C. and the flow rate was maintained at 0.5 mL/min using an isocratic elution. The diluted samples were injected (30 μL) into a HPLC equipped with YMC-PACK Diol-200 column and a UV detector. Proteins in the sample were separated by size and detected by UV absorption at 280 nm.

A350:

UV absorption at 350 nm was measured using 96 well plate Spectramax reader as an indication of turbidity. The absorption readings were blanked against empty plate reading and normalized for sample pathlength.

HP-HIC:

High performance hydrophobic interaction chromatography (HP-HIC) was used to assess oxidized products from the non-oxidized molecule. The percentage of pre-peaks, determined to be oxidized species comprising heavy chain Met105 oxidation on one heavy chain by previous analytical characterization, as well as the percentage of the main and percentage of the post peaks were determined. A HP-HIC method was performed by diluting the sample to 5.0 mg/mL in purified water. The sample was then injected (10 μL) into an HPLC equipped with a Tosoh Phenyl-5PW column and a UV detector at 280 nm. For the HIC analysis a mobile phase containing a gradient of the following components (mobile phase A: 5 mM sodium phosphate in 2% acetonitrile, pH 7.0; mobile phase B: 400 mM ammonium sulfate, 5 mM sodium phosphate in 2% acetonitrile, pH 6.9; was used.

VP-DSC:

Valerian-Plotnikov differential scanning calorimetry (VP-DSC) can be used to determine the thermal and conformational stability of monoclonal antibodies. DSC determines the heat capacity ($C_p$) of the protein solution relative to that of the placebo solution for increasing temperatures, producing a thermal transition upon protein unfolding. For monoclonal antibodies, multiple unfolding transitions (Tonset, Tm1, Tm2) are typically seen in the DSC thermogram corresponding to unfolding of individual domains Example 2

Evaluation of the Stability of High Concentration Pembrolizumab Formulations

An initial study was performed to evaluate the stability of formulations comprising a high (160 mg/ml) concentration of pembrolizumab and to evaluate the impact of different formulation excipients.

Pembrolizumab drug substance stock solutions were prepared in 10 mM acetate pH 5.0 (189 mg/mL) and 10 mM histidine pH 5.5 (187 mg/mL) by tangential flow filtration. Pembrolizumab formulations were prepared to 160 mg/mL target concentration by spiking the protein stock solution with excipient stock solutions and respective buffer. Test formulations comprising a high concentration of pembrolizumab (see Table 4) were prepared in 6R glass vials at a volume of between 3 mL and 4 mL. Excipients were spiked into the protein solution to achieve target levels of each excipient and brought to final volume using either acetate or histidine buffer. Formulation 2 was prepared at 125 mg/mL (without surfactant) and concentrated to greater than 160 mg/mL using a Millipore centricon device (10,000MWCO). PS80 was added after the concentration was adjusted to 160 mg/mL with placebo (i.e., formulated matrix, with all components except Ab and surfactant). Samples were stored at 2-8° C. after preparation until they were filled into vials.

TABLE 4

High Concentration Pembrolizumab Formulations

| Formulation | Pembro Concentration | Buffer | Stabilizer | Surfactant | Anti-Oxidant |
|---|---|---|---|---|---|
| 1 | 160 mg/mL | Histidine | 7% sucrose | 0.02% PS80 | — |
| 2 | 160 mg/mL | Histidine | 5% sorbitol | 0.02% PS80 | — |
| 3 | 160 mg/mL | Histidine | 7% sucrose | 0.1% F127 | — |
| 4 | 160 mg/mL | Histidine | 7% sucrose | 0.02% PS80 | 10 mM Met |
| 5 | 160 mg/mL | Acetate | 7% sucrose | 0.02% PS80 | — |

Pembrolizumab formulated solutions were filtered using Millex GV 0.22 μm PVDF 33 mm filter and filled into glass low volume HPLC vials (Waters #186000384c, 12×32 mm glass screw neck vial, 200 μL per vial). Vials were capped, and the caps were wrapped with parafilm to minimize potential evaporation. Samples were staged in 2-8° C., 25° C. and 40° C. environmental stability chambers. Each sample box was double bagged prior to placement into the stability chamber for a period of twelve weeks.

Stability of the formulations was evaluated using HP-SEC (to assess purity) and HP-IEX (charge profile) over a period of twelve weeks. Results demonstrate that there were no changes for any of the formulations that were stored at 5° C. (as used herein and throughout the Examples, the term "5° C." is used interchangeably with "2-8° C.", which indicates 5° C.+/−3° C. (standard deviation) during the 12-week time period. Therefore, all formulations were considered stable at the 5° C. storage condition. At 25° C., changes were observed via HP-SEC (a slight decrease in % mAb) and HP-IEX (slight decrease in % main) for each of the formulations over the time period tested. No differences were observed among results for the five formulations at 25° C. using either of these two techniques (data not shown). More pronounced changes were observed for all of the formulations stored at 40° C. evaluated by both techniques relative to the same formulations stored at 25° C. The lowest decrease in % mAb by HP-SEC after 12 weeks was observed with formulation 4 at 40° C. compared to the other formulations stored at 40° C. for 12 weeks, suggesting that this formulation may have improved stability (data not shown). There were no differences in charge profile among the five formulations at any of the temperatures for the length of the testing period (i.e. data at each 4-week interval was similar among the five formulations). Data not shown.

Figure 1B:
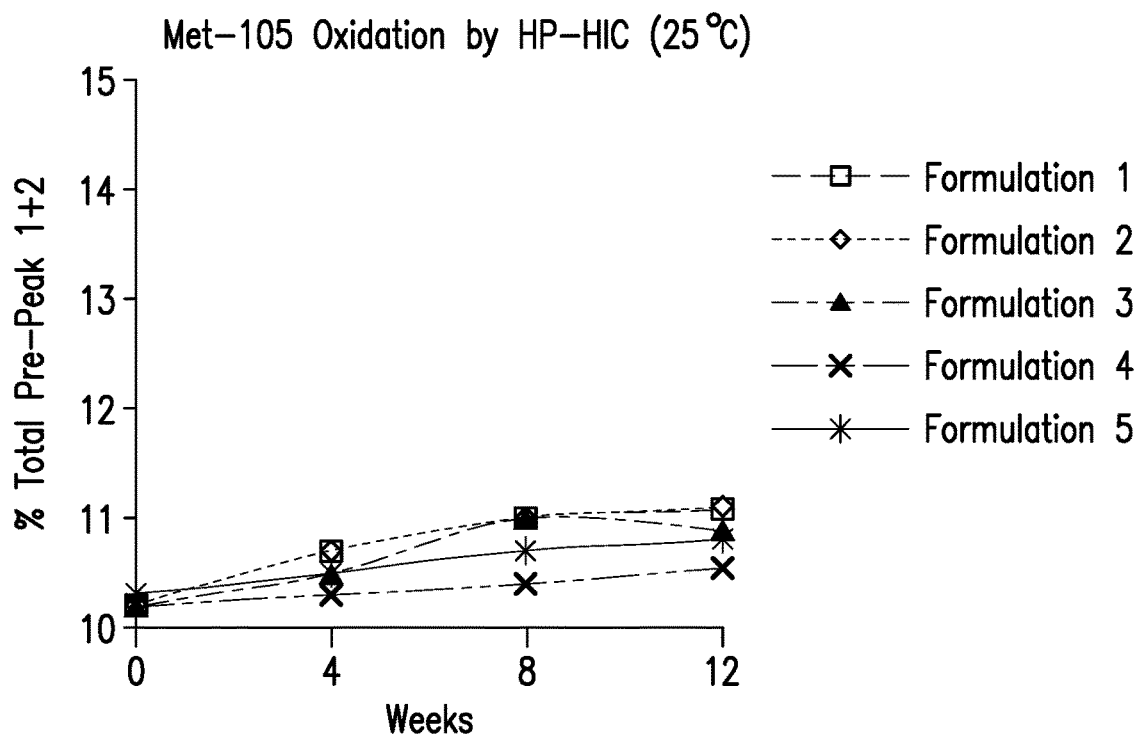
Figure 1C:
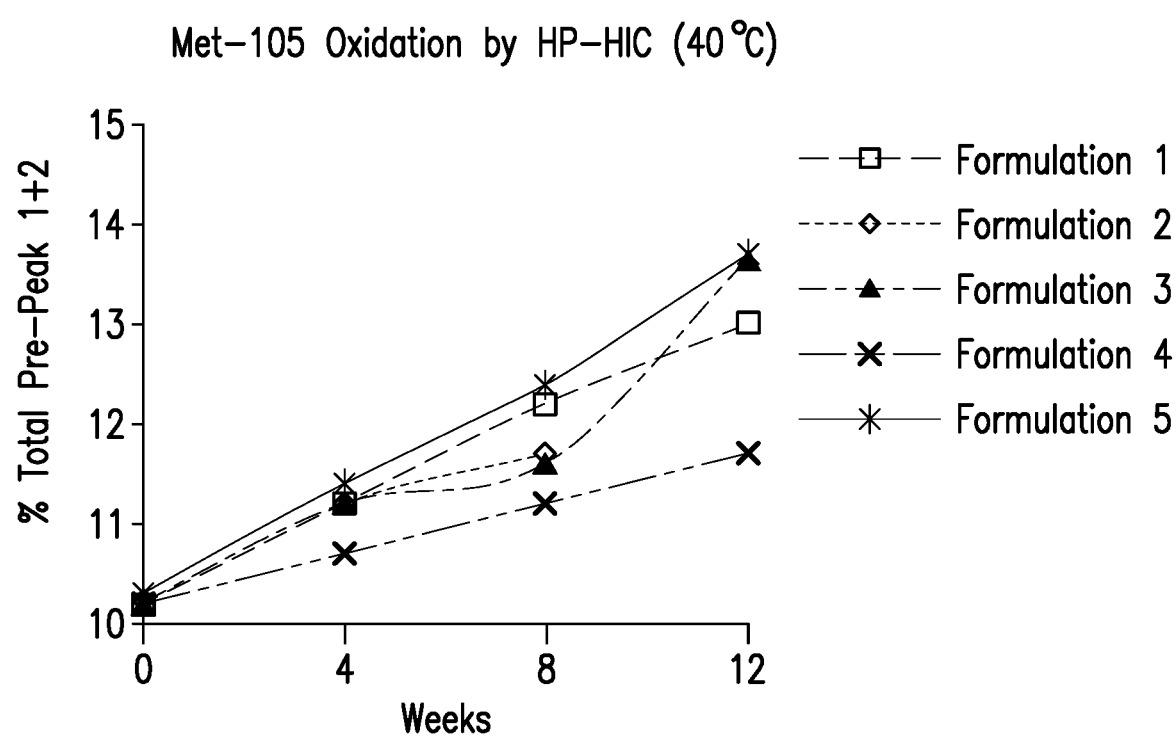

Oxidation of methionine-105 (Met-105) was also monitored by HP-HIC for each of the test formulations over the 12-week period. No changes in Met-105 oxidation were observed for any of the formulations at 5° C. (FIG. 1A). At 25° C., a trend of slight increase of % total pre-peak 1+2 (representing approximately 50% oxidized Met-105 or one oxidized Met-105 per molecule) was observed among all five formulations (FIG. 1B), which was more pronounced at 40° C. (FIG. 1C). The lowest amount of % total pre-peak 1+2 was observed with formulation 4 over the 12-week period, suggesting that this formulation might be improving stability.

Example 3

Evaluation of the Stability of High Concentration Pembrolizumab Formulations Comprising Arginine as a Viscosity-Lowering Agent A further study was performed to evaluate the stability of formulations comprising an even higher concentration of pembrolizumab (200 mg/mL as compared to 160 mg/mL used in EXAMPLE 2). In this study, arginine (3%, 2%) was used as a viscosity lowering agent, alone or in combination with sucrose, and the impact on storage stability of pembrolizumab was evaluated.

For this study, pembrolizumab concentrated drug substance was prepared at 234 mg/mL in 10 mM histidine pH 5.4 by concentration and diafiltration. Pembrolizumab drug product formulations (#1 to #3) were prepared to 200 mg/mL target concentration in 200 mL volumetric flasks by spiking the protein stock solution with excipient stock solutions and 10 mM histidine buffer (see Table 5). Each of the formulated solutions was filtered using 0.22 μm PVDF membrane Stericup 250 mL devices, and filled into 1 mL syringes (Hypak SCF 1 mL with BD Hypak SCF Stoppers) and 2 mL vials (Nuova Ompi 0612090.5657), with a 1 mL drug product fill volume. Samples were staged, protected from light, and placed in a 2-8° C. environmental stability chamber for 12 months, a 25° C. stability chamber for 9 months and a 40° C. stability chamber for 5 months. The test formulations for this study did not contain any anti-oxidant.

TABLE 5

High Concentration Pembrolizumab Formulations for EXAMPLE 3

| Antibody | Buffer | No. | Stabilizer 1 | Stabilizer 2 | Surfactant | Container (Fill) |
|---|---|---|---|---|---|---|
| 200 mg/mL Pembro | 10 mM His pH 5.5 | 1A | 7% Sucrose | — | 0.02% PS80 | 2 mL glass vials (1 mL) |
| | | 2A | — | 3% Arginine | 0.02% PS80 | |
| | | 3A | 2% Sucrose | 2% Arginine | 0.02% PS80 | |
| | | 1B | 7% Sucrose | — | 0.02% PS80 | 1 mL BD syringes (1 mL) |
| | | 2B | — | 3% Arginine | 0.02% PS80 | |
| | | 3B | 2% Sucrose | 2% Arginine | 0.02% PS80 | |

The formulations were evaluated by visual observation, A350, HP-SEC (purity), HP-IEX (charge profile), HP-HIC (Met-105 oxidation) and CE-SDS. No changes were observed among the different formulations when stored at 5° C. for up to 12 months, whether stored in vials or syringes, by visual observation, A350, HP-SEC, HP-IEX, HP-HIC, and CE-SDS (NR). Therefore, all formulations were considered stable at the 5° C. storage condition.

Each of the test formulations were visually inspected for changes in coloration or precipitate formation (data not shown). All of the formulations showed some degree of yellow color at 25° C. by visual assessment. The formulations containing sucrose without arginine (formulations 1A and 1B) began to show some yellow color after 3 months. By 9 months, some precipitates or particles were observed in all samples. The formulation comprising 2% sucrose and 2% arginine formed a gel in the vial (formulation 3A), which was evident in some vials as early as 1 month, but not in the syringe (formulation 3B). Rapid changes were observed for all formulations at 40° C. over the 9-month testing period. Yellow coloration was observed in the sucrose-only formulations (1A and 1B) after 1 month, whether in a vial or a syringe.

A350 values were measured as an indication of turbidity (data not shown). At 25° C., a trend of increase in turbidity was observed over the 6-month testing period for sucrose-containing samples (formulations 1A and 1B) and samples comprising a sucrose-arginine combination in a vial (formulation 3A). An increase in A350 value of the sucrose samples at the 6-month timepoint correlated with the observation of yellow coloration. Additionally, the A350 of the sucrose-arginine samples were found to be atypically higher than samples containing the same combination in a syringe. At 40° C., a more pronounced trend of increased turbidity over time was observed for all formulations. Sucrose-containing samples (formulations 1A and 1B) turned amber and were therefore A350 was not measured at 6 months. The sucrose-arginine formulation in a vial (formulation 3A) was also not measured by A350 at 6 months due to gel formation. A350 results for arginine-containing formulations (no sucrose, formulations 2A and 2B) in either vials or syringes and sucrose-arginine formulations in syringes (formulation 3B) were comparable.

Purity of the formulations was determined by HP-SEC for a period of 9 months (data not shown). At 25° C., a trend of slight decrease in % mAb, with a corresponding increase in % HMW, was observed among all 5 formulations over time. The sucrose-containing formulations in vials and syringes (formulation 1A and 1B) showed the most changes as compared to the other formulations. % LMW data indicated significant variability at intermediate time points (3M, 6M) and was not conclusive. At 40° C., a trend of decrease in % mAb, with a corresponding increase in % HMW and % LMW, was observed among all the formulations over the 9-month period. There were no clear differences among the different formulations during the time tested.

Charge profile was determined by HP-IEX (data not shown). At 25° C., a trend of slight decrease in % main, and % total basic, with a corresponding increase in % acidic, was observed among all 5 formulations over 9 months. The most changes were observed for the sucrose-containing formulations (formulations 1A and 1B) in vials or syringes compared to the arginine-containing (formulations 2A and 2B) and sucrose+arginine-containing formulations (formulations 3A and 3B). At 40° C., a more pronounced trend of decrease in % main, and % total basic, with a corresponding increase in % acidic, was observed among all 5 formulations. There were no clear differences among the different formulations after 3 months. Additionally, there were no clear differences in stability profiles for formulations in vials compared to syringes.

Figure 2A:
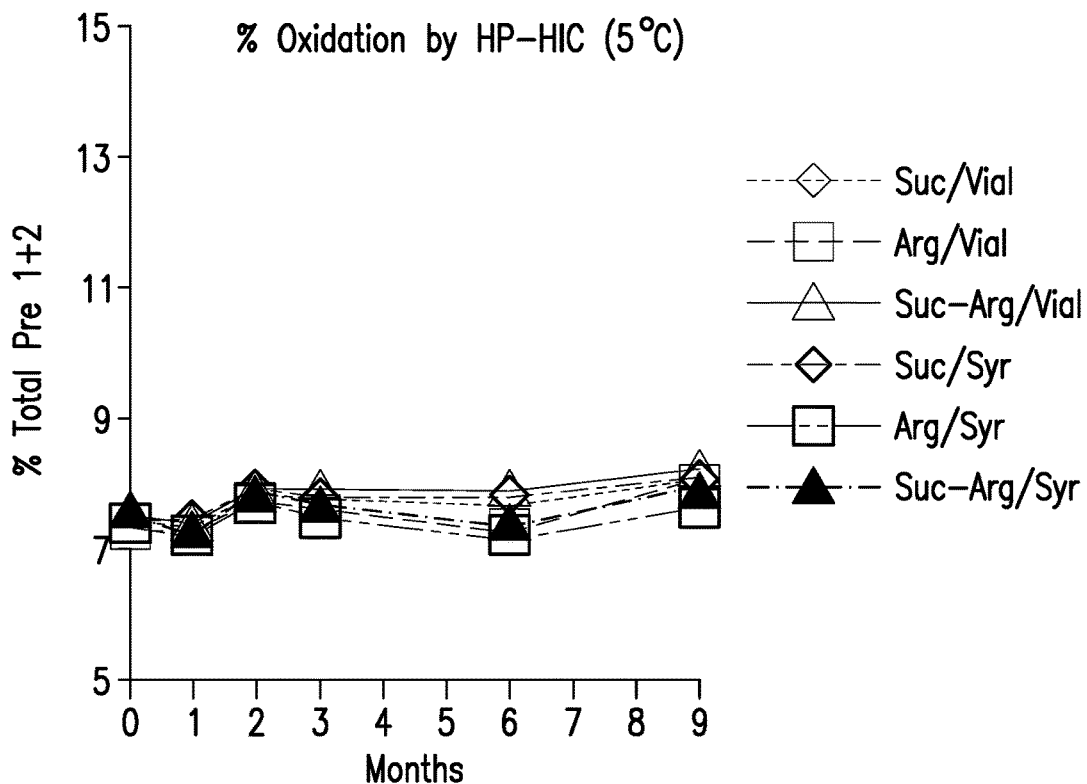
FIGS. 2A-2C show results of an HP-HIC study of the formulations in EXAMPLE 3. Results are provided for test formulations stored at 5° C.
Figure 2B:
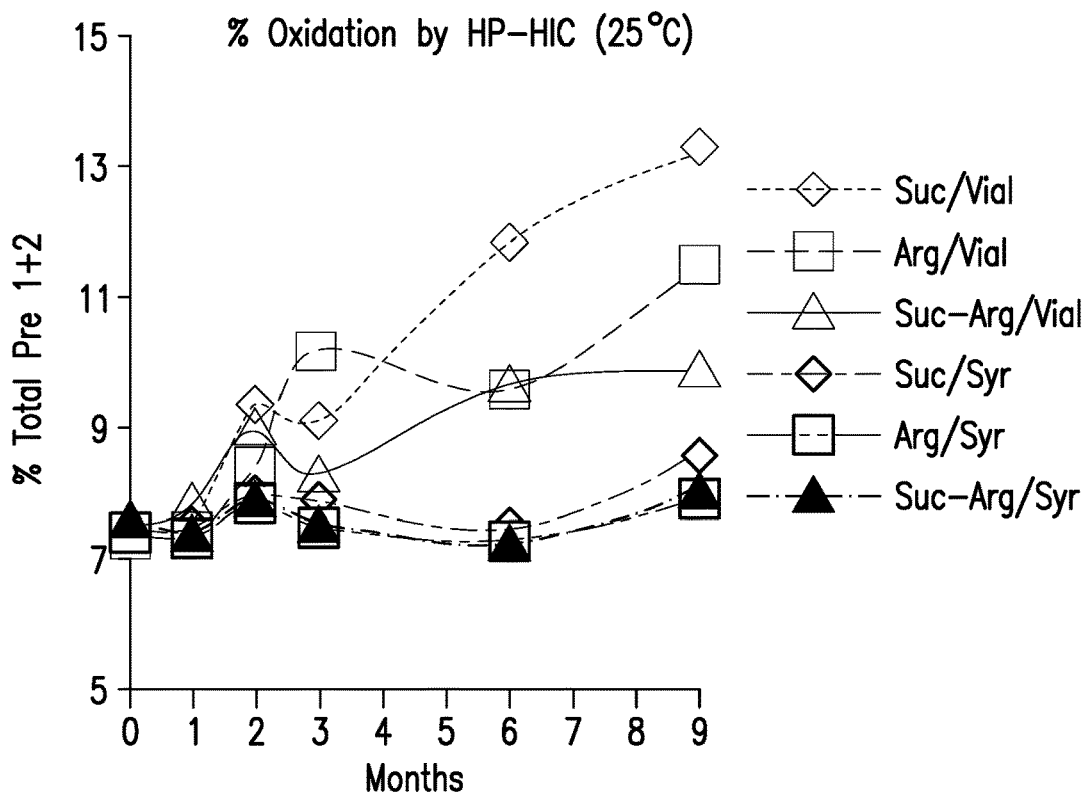
Figure 2C:
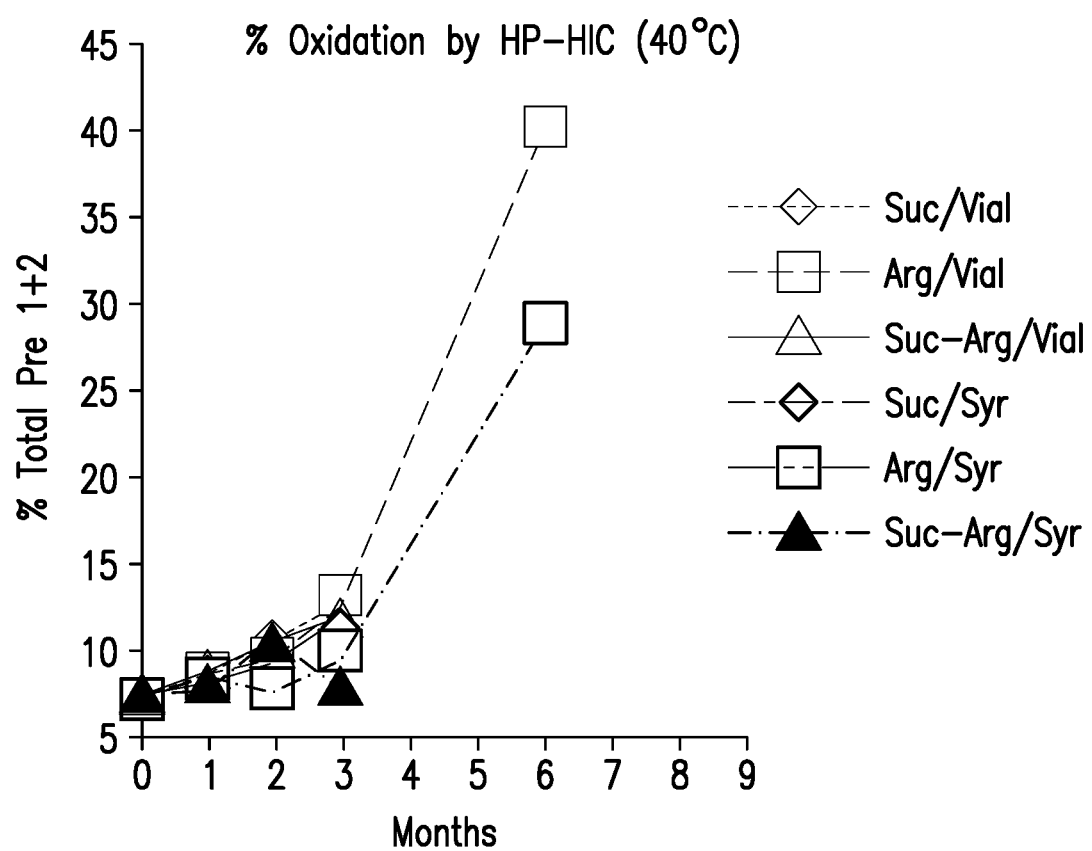

Met-105 oxidation was measured by HP-HIC. Minimal changes in Met-105 oxidation were observed for any of the formulations at 5° C. over a 9-month period (FIG. 2A). At 25° C., a trend of slight increase in % total pre-peak 1+2 was observed among all formulations in vials, which was not observed for the corresponding formulations in syringes (FIG. 2B). A higher increase in oxidation over 9 months was observed for the sucrose-containing formulations (no arginine) in vials as compared to formulations containing arginine (with or without sucrose). At 40° C., a steep increase in the rate of oxidation was observed after 3 months for the arginine-containing formulations (vial and syringe) and the sucrose formulation in a syringe (FIG. 2C). The other formulations were not tested after 3 months due to gel formation or amber coloration (see discussion above).

Example 4

Evaluation of Formulations Comprising a High Concentration of Pembrolizumab with Alternative Viscosity Lowering Agents An additional study was performed to test the utility of alternative excipients as viscosity lowering agents in high concentration pembrolizumab formulations. A series of formulations were prepared (Table 6) in micro-recovery HPLC vials with a 400 µL fill volume. The formulations in this study did not comprise any anti-oxidant. Samples were staged in a 5° C., 25° C. and 40° C. stability chambers for 12 weeks. The test formulations for this study did not contain any anti-oxidant.

TABLE 6

High Concentration Pembrolizumab Formulations for EXAMPLE 4

| Formulation | Antibody | Buffer | Stabilizer 1 | Stabilizer 2 | Surfactant |
|---|---|---|---|---|---|
| 1 | 200 mg/mL pembrolizumab | 10 mM Histidine pH 5.5 | 2% Histidine | — | 0.02% PS80 |
| 2 | | | 2% Histidine | 2% Arginine | 0.02% PS80 |
| 3 | | | 2% Histidine | 2% Sucrose | 0.02% PS80 |
| 4 | | | 150 mM Camphor sulfonic acid | — | 0.02% PS80 |
| 5 | | | 150 mM Guanidine hydrochloride | — | 0.02% PS80 |

Figure 3A:
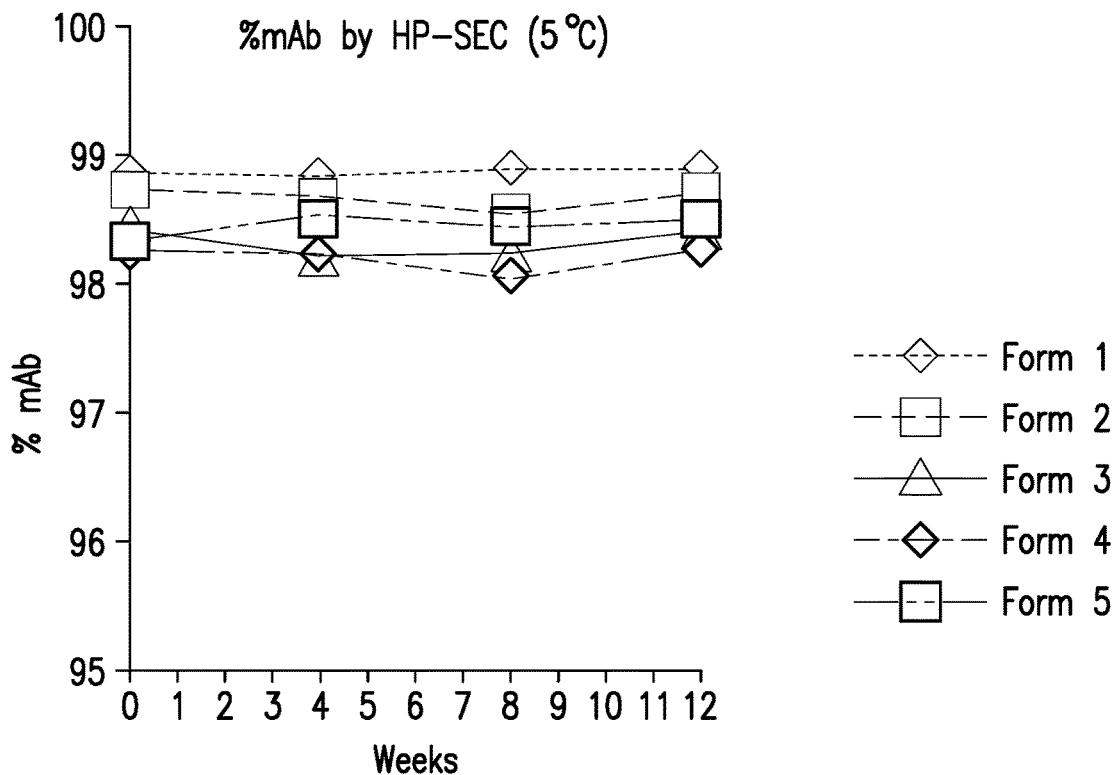
FIGS. 3A-3C show results of an HP-SEC analysis (measured as % mAb) of the formulations described in EXAMPLE 4. Results are provided for formulations stored at 5° C.
Figure 3B:
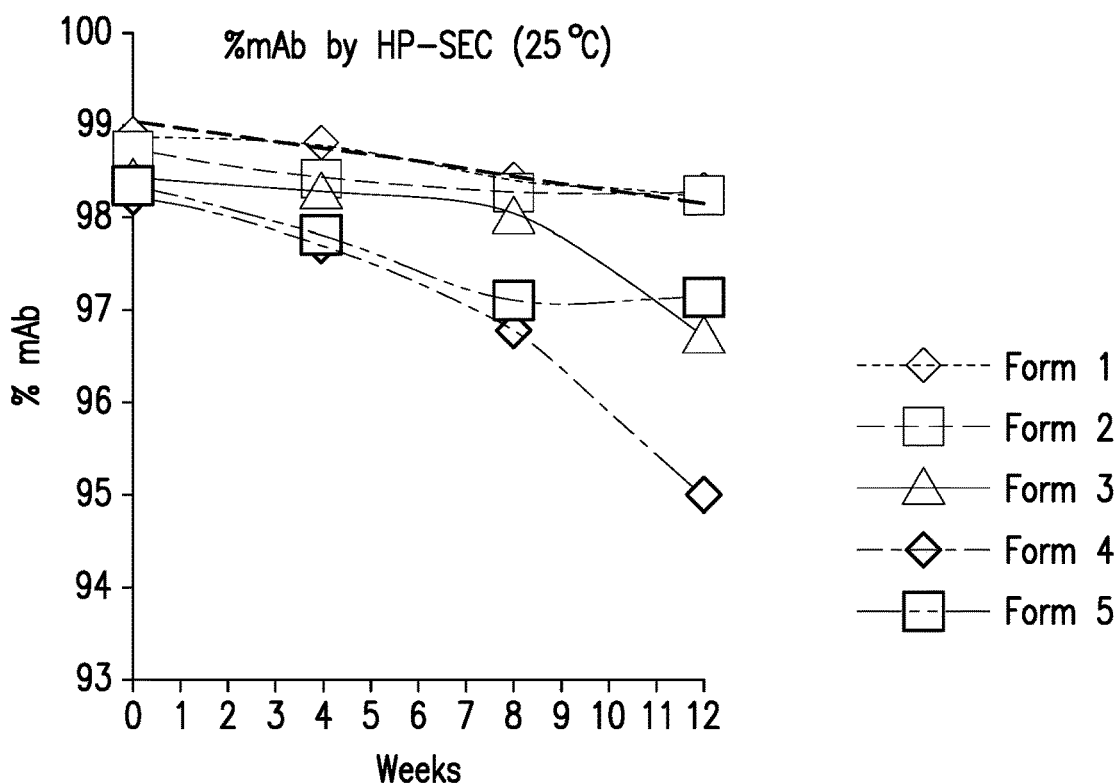
Figure 3C:
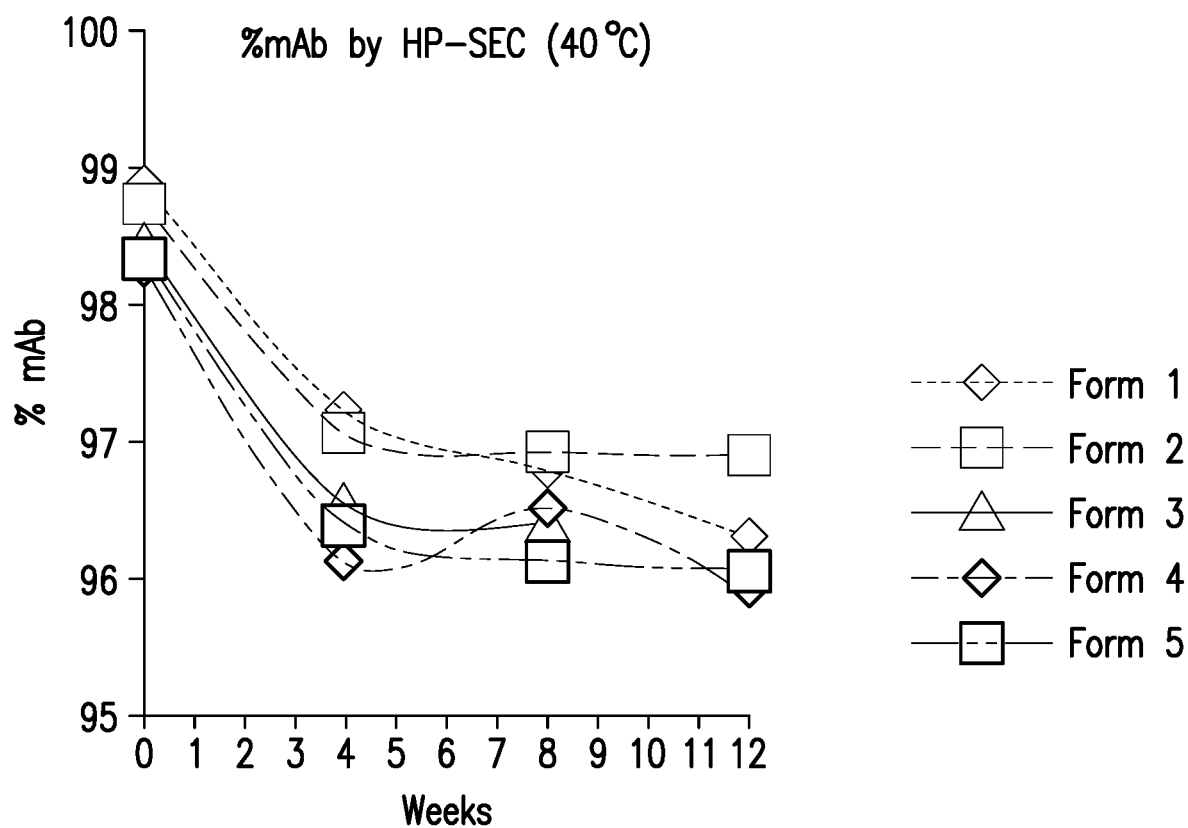

No changes in purity were observed by HP-SEC analysis (measured as % mAb) for formulations stored at 5° C. over a period of 12 weeks (FIG. 3A). For samples stored at 25° C., a trend was observed among all five formulations which showed a slight decrease in % mAb, with formulation 4 (150 mM camphor sulfonic acid) showing the maximum decrease (~5%) among the 5 formulations (FIG. 3B). The trend of decreased % mAb was also observed for formulations stored at 40° C., with no clear differences among the 5 formulations tested (FIG. 3C).

Similar to results obtained by HP-SEC, no differences in charge profile were observed among the 5 formulations at 5° C. for a 12 week period as evaluated by HP-IEX. Again, a trend was observed at 25° C. which showed a decrease in % main for all five formulations over 12 weeks, with the most pronounced drop measured for formulations 3 and 4 (150 mM camphor sulfonic acid and 150 mM guanidine HCL). At 40° C., a more pronounced decrease in % main by HP-IEX was observed for each of the five formulations over the time tested, with no clear differences among the five formulations (data not shown).

Figure 4A:
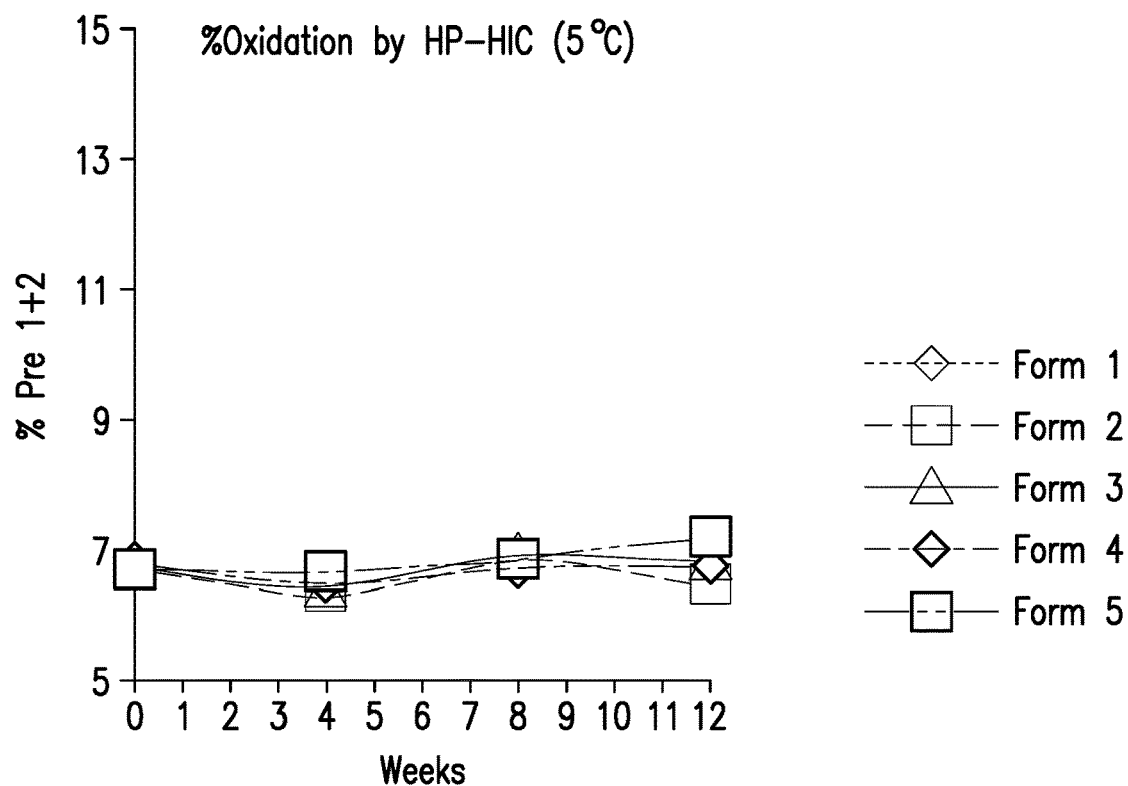
FIGS. 4A-4C show results of HP-HIC analysis of the formulations described in EXAMPLE 4. Results provided show the % of pre-peak 1+2 (oxidized species) formulations stored at 5° C.
Figure 4B:
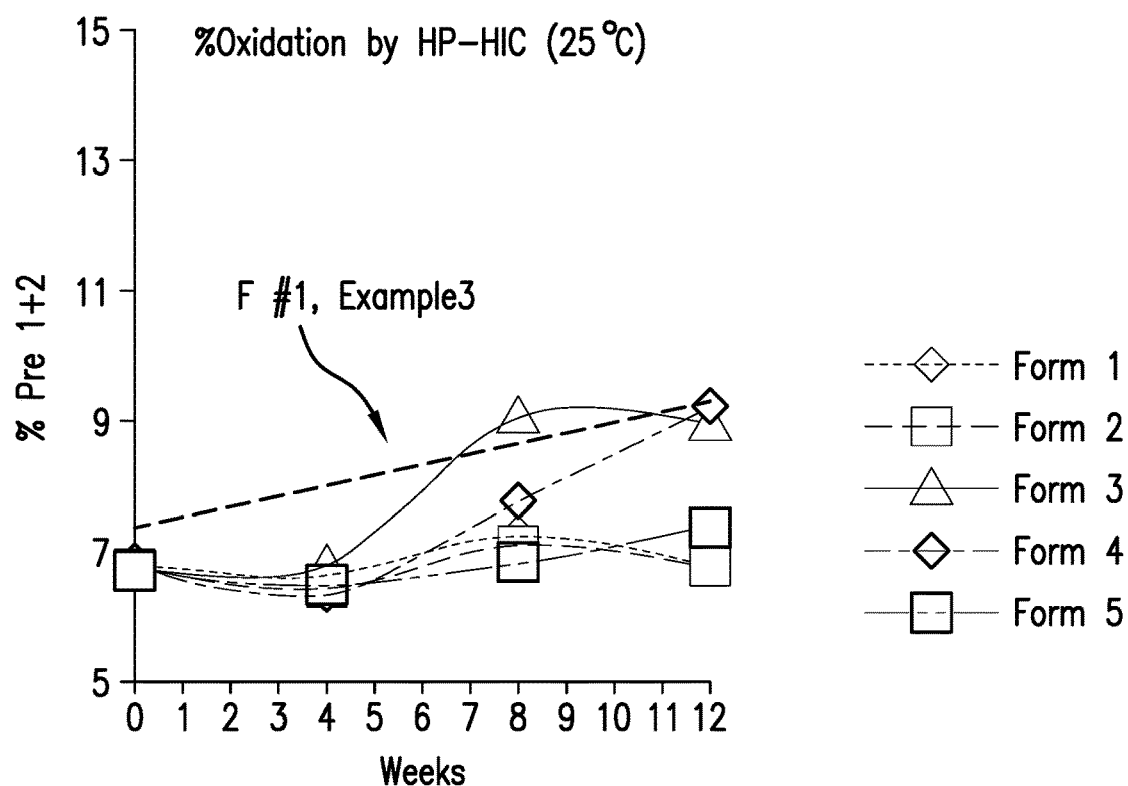

No differences in % Met-105 oxidation (pre-peak 1+2) were observed for any of the five formulations after 12 weeks at the 5° C. storage condition, as measured by HP-HIC (FIG. 4A). However, for formulation 4, an increase in % pre-peak (other than pre-peak 1+2) was observed (data not shown). Pre peaks other than 1+2 contain contributions of molecules where both methionine residues are oxidized per molecule. A slight increase in % total pre-peak 1+2, indicating oxidized species, was observed for formulations 3 (2% histidine, 2% sucrose) and 4 (150 mM camphor sulfonic acid) at 25° C. (FIG. 4B), as well as an increase in % pre-peak for peaks other than 1+2 (data not shown). Minimal changes in % total pre-peak 1+2 were detectable for formulations 1, 2, and 5 (FIG. 4B). However, formulation 1 and formulation 2 did show significant increase in % pre-peaks other than 1+2 (data not shown).

Figure 4C:
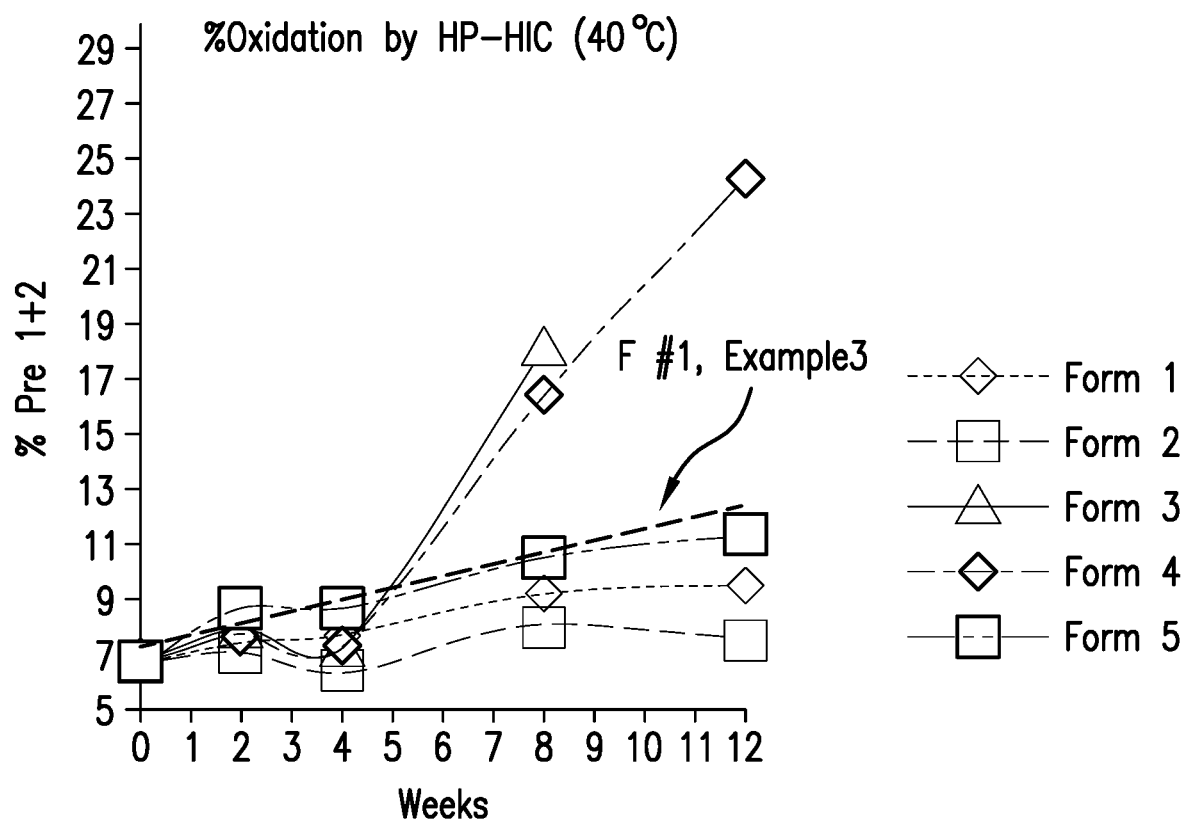

A more pronounced increase was observed in % total pre-peak 1+2 among all 5 formulations at the 40° C. storage condition over the 12 week period, with formulations 3 and 4 again showing the most changes in % total pre-peak 1+2 (FIG. 4C) and % pre-peaks other than 1+2 (data not shown). Formulations 1, 2, and 5 showed the least changes in % pre-peak 1+2 (FIG. 4C), but significant changes in % pre-peaks other than 1+2 were observed, indicating oxidation of both Met-105 residues (data not shown).

Example 5

Analysis of Formulations Comprising Arginine in Combination with Glutamine

Previous studies suggested that an equimolar mixture of arginine and glutamine can suppress temperature-induced aggregation of monoclonal antibodies in biological formulations (Kheddo et al., *Int. J Pharmaceutics* 473: 126-33 (2014)). Fukuda et al. (*Pharm. Res.* 31:992-1001 (2014)) showed that Arg-HCl can suppress antibody aggregation at near-neutral pH, but promoted aggregation and degradation at acidic pH or high temperatures. In that study, the impact of Arg-HCl at high temperature could be mitigated by adding an equimolar mixture of arginine and aspartic acid or glutamic acid, which led to a suppression of aggregation (Fukuda et al.).

In order to investigate the impact of an equimolar mixture of glutamine and arginine on pembrolizumab formulations, a series of compositions were formulated and tested as described below. Concentrated pembrolizumab drug substance was prepared at 252.3 mg/mL in 10 mM histidine, pH 5.5 by concentration and dilafiltration. Formulations C1-C6 were prepared by spiking stock solutions of the following excipients: L-Arginine hydrochloride (475 mM stock), L-Glutamic Acid (170 mM stock), Polysorbate-80 (2% w/w stock), and sucrose (40% w/v stock) into pembrolizumab drug substance to achieve target compositions listed in Table 7. Formulated drug substance batches were filtered using a 0.22 um PVDF syringe filter and filled into 2 mL glass vials (fill volume: 0.5 mL). Vials were capped using 13 mm serum stoppers and sealed using 13 mm flip-off seals. Vials were incubated in 40° C. with 75% relative humidity (RH) walk-in incubator. Vials were tested at T0, 1 week, 2 week, 4 week, and 8 week time points.

Figure 5:
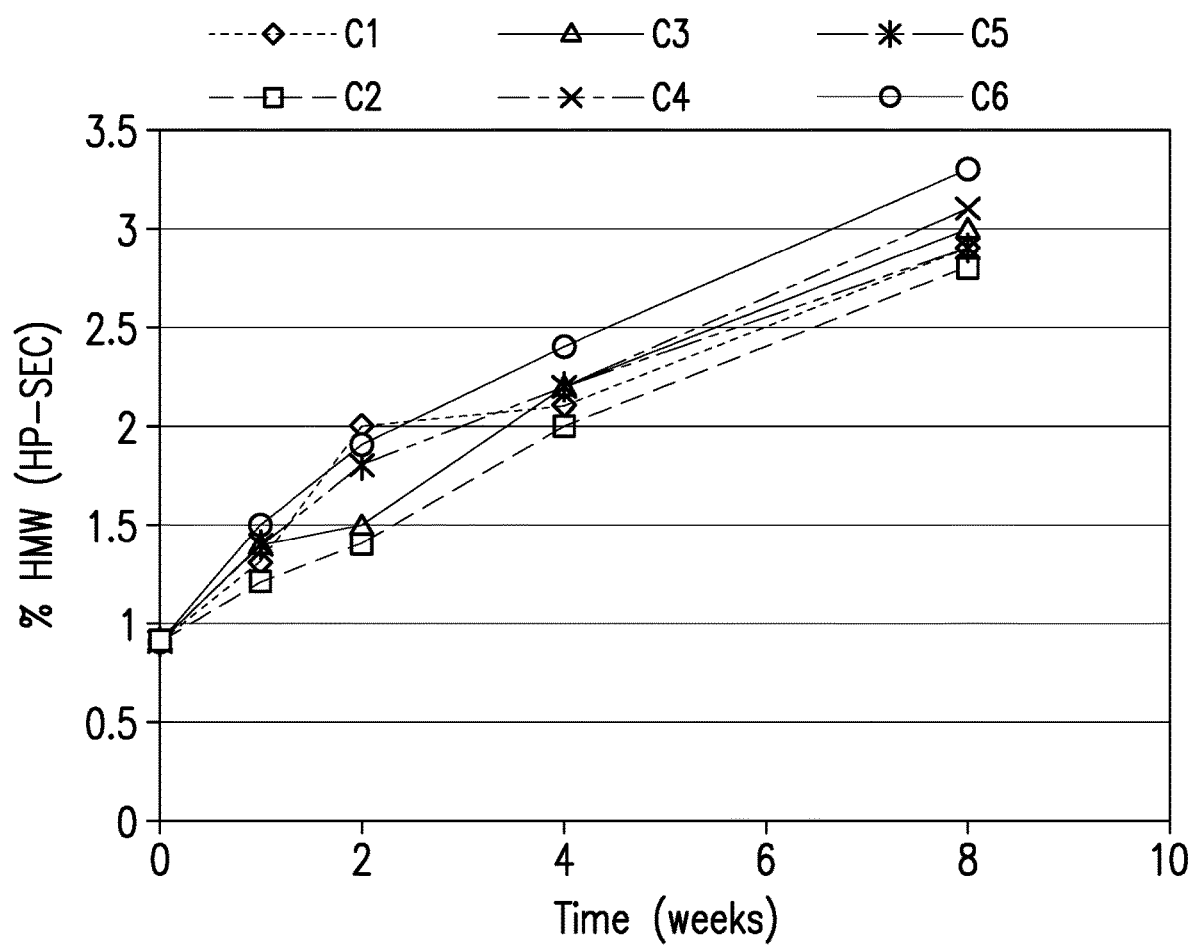
FIG. 5 shows the amount of aggregation of each of the formulations in EXAMPLE 5 over an 8-week period of storage at 40° C. as measured by HP-SEC.

Thermal unfolding was tested by DSC (Table 7) and viscosity of each formulation was measured (Table 7). Results indicate that there was no improvement in thermal unfolding behavior in the presence of an equimolar mixture of Arg and Glu. A reduction in viscosity was observed for all formulations comprising Arg, Glu or Arg:Glu (1:1) relative to C1, which contained no arginine or glutamine (Table 7). The amount of aggregation of each of these formulations over a 12-week period of storage at 40° C. was also measured by HP-SEC. Results indicate that there was no reduction in aggregation for the formulations comprising an equimolar mixture of Arg:Glu (FIG. 5).

TABLE 7

High Concentration Pembrolizumab Formulations for EXAMPLE 5

| No. | Formulation | DSC (thermal unfolding) | | | Viscosity (cP) |
| --- | --- | --- | --- | --- | --- |
| | | Tonset | Tm1 | Tm2 | |
| C1 | 167 mg/mL pembrolizumab, 7% Sucrose, 0.02% PS-80, 10 mM Histidine buffer, pH 5.5 | 63.9 | 66.9 | 78.2 | 21.9 |
| C2 | C1 + 35 mM Arginine | 64.2 | 64.5 | 76.8 | 18.2 |
| C3 | 167 mg/mL pembrolizumab, 0.02% PS-80, 10 mM Histidine buffer, pH 5.5 + 40 mM Arg + 40 mM Glu | 62.3 | 64.7 | 75.9 | 16.0 |
| C4 | 167 mg/mL pembrolizumab, 0.02% PS-80, 10 mM Histidine buffer, pH 5.5 + 20 mM Arg + 20 mM Glu | 61.8 | 65.2 | 76.0 | 16.8 |
| C5 | 167 mg/mL pembrolizumab, 0.02% PS-80, 10 mM Histidine buffer, pH 5.5 + 40 mM Arg | 61.8 | 64.7 | 76.0 | 15.5 |
| C6 | 167 mg/mL pembrolizumab, 0.02% PS-80, 10 mM Histidine buffer, pH 5.5 + 40 mM Glu | 62.8 | 64.8 | 75.8 | 17.9 |

Example 6

Impact of Antioxidants and Chelators on Stability in the Presence of Metal Ions

Study 1:

Metal ions can be introduced during manufacturing of biological formulations, for example from steel tanks commonly used for processing monoclonal antibody products and related buffers. In order to determine the impact of antioxidants and chelators on formulation stability in the presence of metal ions, a series of test formulations were evaluated by HP-SEC (Table 8). Concentrated pembrolizumab drug substance was prepared at 252.3 mg/mL in 10 mM histidine, pH 5.5 by concentration and dilafiltration. Formulations D1-D5 were prepared by spiking stock solutions of the following excipients: methionine (100 mM stock), ferrous chloride (0.0227% w/v stock), polysorbate-80 (2% w/w stock), and sucrose (40% w/v stock) into pembrolizumab drug substance to achieve target compositions listed in Table 8.

Formulated drug substance batches were filtered using a 0.22 um PVDF syringe filter and filled into 2 mL glass vials (fill volume: 0.5 mL). Vials were capped using 13 mm serum stoppers and sealed using 13 mm flip-off seals. Vials were incubated in 40° C./75% RH walk-in incubator. Vials were tested at T0, 1 week, 2 week, 4 week, and 8 week timepoints.

The base formulation tested in this study (Formulation 1) comprised a high concentration of pembrolizumab with sucrose and PS80 in histidine buffer (see Table 8, no. D1), whereas Formulation D3 comprised the base formulation+ metal ions with an antioxidant (methionine) and Formulation D5 comprised the base formulation+metal ions and a chelator (DTPA).

TABLE 8

Formulations used for Example 6, Study 1

| Formulation | | T0 | % Aggregates (HP-SEC) | | | |
| --- | --- | --- | --- | --- | --- | --- |
| | | | 1 week | 2 weeks | 4 weeks | 8 weeks |
| D1 | 167 mg/ml pembrolizumab, 7% Sucrose, 0.02% PS-80, 10 mM Histidine buffer, pH 5.5 | 0.8 | 1.1 | 1.4 | 2.1 | 3.1 |

TABLE 8-continued

Formulations used for Example 6, Study 1

| Formulation | | T0 | % Aggregates (HP-SEC) | | | |
| --- | --- | --- | --- | --- | --- | --- |
| | | | 1 week | 2 weeks | 4 weeks | 8 weeks |
| D2 | D1 + 1 mM Methionine | 0.8 | 1.1 | 1.4 | 2.1 | 3.1 |
| D3 | D1 + 1 ppm Fe++, 1 mM Methionine | 0.8 | 1.3 | 1.6 | 2.5 | 4.0 |
| D4 | D1 + 1 ppm Fe++ | 0.8 | 1.3 | 1.7 | 2.5 | 4.2 |
| D5 | D1 + 1 ppm Fe++, 100 µM DTPA | 0.8 | 1.1 | 1.5 | 2.2 | 3.2 |

Results showed that methionine did not prevent aggregation in the presence of metal ions (Table 8, Formulation D3). A lower % aggregates was observed in the formulation comprising DTPA in the presence of metal ions (Formulation D5) compared with the base formulation in the presence of metal ions with no chelator/antioxidant (Formulation D4) or the formulation with methionine (Formulation D3) in the presence of metal ions after 8 weeks.

The formulations were also evaluated at 40° C. over 8 weeks by HP-HIC to determine the impact of methionine and DTPA on oxidation in the presence of metal ions (data not shown). A slight reduction in oxidation was observed in the formulation comprising methionine and the formulation comprising DTPA in the presence of $Fe^{2+}$ relative to controls.

Study 2:

The impact of additional antioxidants and chelators (Formulations E1-E9, Table 9) on stability and oxidation in the presence of metal ions at 40° C. was evaluated by HP-SEC and HP-HIC.

TABLE 9

Formulations used for Example 6, Study 2

| Formulation | | T0 | % Aggregates (HP-SEC) | | | |
| --- | --- | --- | --- | --- | --- | --- |
| | | | 1 week | 2 weeks | 4 weeks | 8 weeks |
| | Lead formulation (D1)* | 0.8 | 1.1 | 1.4 | 2.1 | 3.1 |
| E1 | D1 + 5 mM Methionine | 1.0 | 1.3 | 1.6 | 2.1 | 2.4 |
| E2 | D1 + 10 mM Methionine | 0.9 | 1.3 | 1.5 | 2.1 | 2.4 |

TABLE 9-continued

Formulations used for Example 6, Study 2

| | | \% Aggregates (HP-SEC) | | | | |
|---|---|---|---|---|---|---|
| | | T0 | 1 week | 2 weeks | 4 weeks | 8 weeks |
| E3 | D1+ 1 ppm Fe++, 10 mM Methionine | 1.0 | 1.4 | 1.7 | 2.4 | 2.9 |
| E6 | D1 + 1 ppm Fe++, 250 uM EDTA | 1.0 | 1.4 | 1.7 | 2.5 | 3.1 |
| E7 | D1 + 1 ppm Fe++, 250 uM DTPA | 1.0 | 1.4 | 1.7 | 2.3 | 2.6 |
| E8 | D1 + 1 ppm Fe++, 20 mM Sodium Citrate | 1.0 | 1.5 | 1.9 | 2.5 | 2.8 |
| E9 | D1 + 1 ppm Fe++, 5 mM Glutathione | 0.8 | 2.4 | 3.3 | 4.6 | 5.0 |

*Data provided are from the Study summarized in Table 8.

HP-SEC results (see Table 9) indicate that formulations containing 5 mM and 10 mM methionine (Formulations E1 and E2) showed a low increase in aggregates without metal ions. Formulations containing methionine and DTPA (Formulations E3 and E7) showed a lower increase in aggregate levels in presence of metal ions compared to EDTA (Formulation E6). The greatest increase in aggregates was observed in the formulation containing glutathione in the presence of metal ions (Formulation E9).

Figure 6:
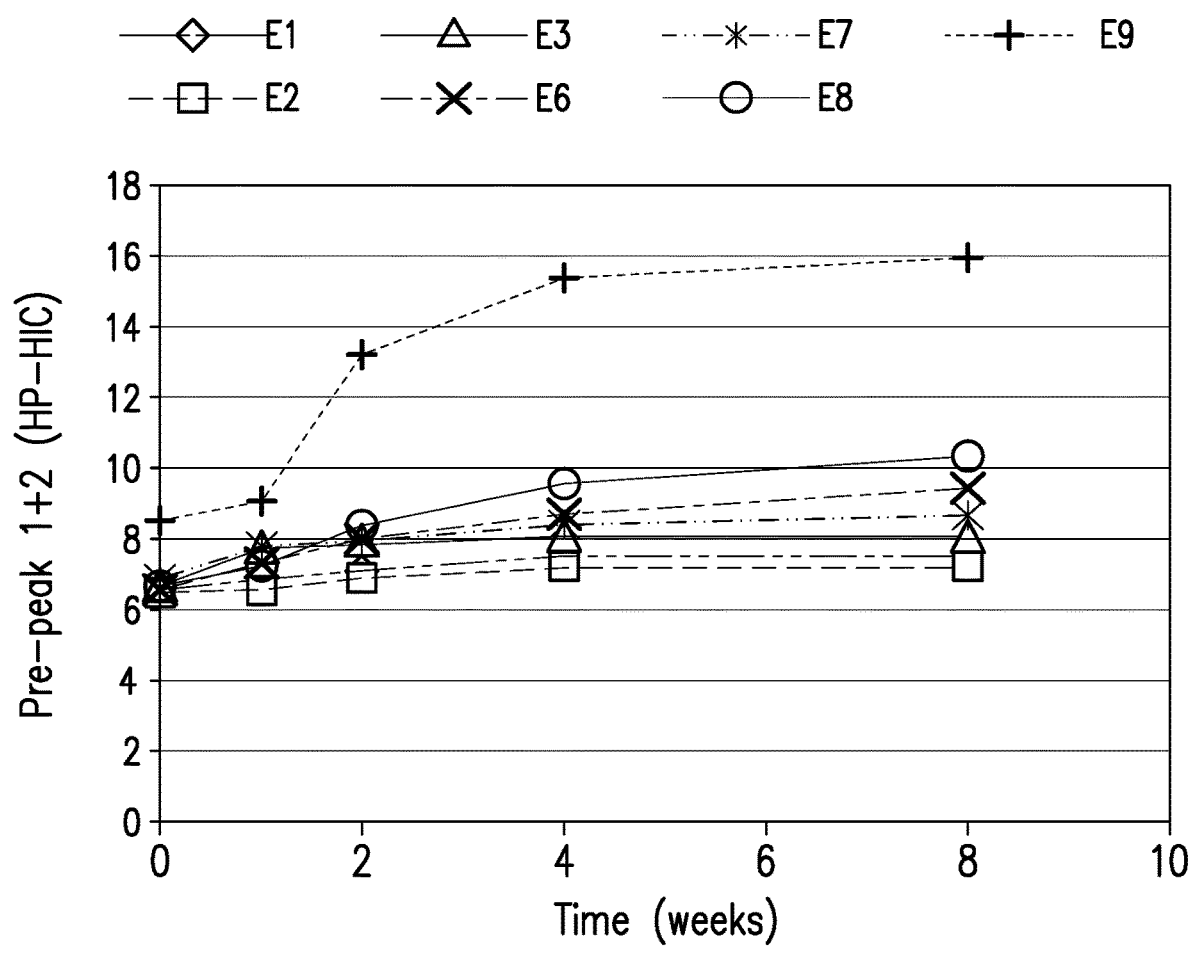
FIG. 6 shows the oxidation of Met-105 in the formulations in EXAMPLE 6, Study 2, at 40° C. over an 8-week period as measured by HP-HIC.

Oxidation of the formulations at 40° C. was also tested over the 8-week period by HP-HIC (see FIG. 6). Reduced oxidation levels over the 8-week period were observed by HP-HIC analysis for formulations containing 5 mM and 10 mM methionine (Formulations E1 and E2) compared to the other formulations tested. The formulations containing 10 mM methionine (Formulation E3) and 250 uM DTPA (Formulation E6) showed a low level of oxidation over the 8-week period in the presence of metal ions. Results also indicate that DTPA was more effective than EDTA at preventing oxidation over time. Sodium citrate and glutathione did not appear to be as effective at controlling oxidation in the presence of metal ions as methionine, DTPA or EDTA.

Study 3:

An additional study was undertaken to evaluate the impact of antioxidants and chelators separately and in combination (with or without metal ions) to further optimize excipient levels. Following formulation, the samples were stored at 40° C. for 8 weeks and evaluated by HP-SEC at T=0, 4 weeks and 8 weeks (see Table 10).

TABLE 10

HMW (SEC) for Formulations Used in EXAMPLE 6, Study 3

| Formulation | | T = 0 | 4 weeks/ 40° C. | 8 weeks/ 40° C. |
|---|---|---|---|---|
| H1 | 167 mg/mL pembrolizumab, 7% Sucrose, 0.02% PS-80, 10 mM Histidine buffer, pH 5.5 | 1.01 | 2.01 | 2.81 |
| H2 | 167 mg/mL pembrolizumab, 7% Sucrose, 0.02% PS-80, 10 mM Histidine buffer, pH 5.5, 100 μM DTPA | 1.01 | 2.07 | 2.84 |
| H3 | 167 mg/mL pembrolizumab, 7% Sucrose, 0.02% PS-80, 10 mM Histidine buffer, pH 5.5, 1 ppm Fe++, 100 μM DTPA | 1.01 | 2.10 | 2.88 |
| H4 | 167 mg/mL pembrolizumab, 7% Sucrose, 0.02% PS-80, 10 mM Histidine buffer, pH 5.5, 100 μM EDTA | 0.90 | 1.63 | 2.18 |
| H5 | 167 mg/mL pembrolizumab, 7% Sucrose, 0.02% PS-80, 10 mM Histidine buffer, pH 5.5, 1 ppm Fe++, 100 μM EDTA | 0.92 | 1.98 | 3.13 |
| H6 | 167 mg/mL pembrolizumab, 7% Sucrose, 0.02% PS-80, 10 mM Histidine buffer, pH 5.5, 10 mM Methionine, 100 uM DTPA | 1.00 | 2.07 | 2.80 |
| H7 | 167 mg/mL pembrolizumab, 7% Sucrose, 0.02% PS-80, 10 mM Histidine buffer, pH 5.5, 1 ppm Fe++, 10 mM Methionine, 100 uM DTPA | 0.99 | 2.07 | 2.81 |
| H8 | 167 mg/mL pembrolizumab, 7% Sucrose, 0.02% PS-80, 10 mM Histidine buffer, pH 5.5, 10 mM Methionine, 100 uM EDTA | 0.91 | 1.65 | 2.17 |
| H9 | 167 mg/mL pembrolizumab, 7% Sucrose, 0.02% PS-80, 10 mM Histidine buffer, pH 5.5, 1 ppm Fe++, 10 mM Methionine, 100 uM EDTA | 0.91 | 1.83 | 2.67 |
| H10 | 167 mg/mL pembrolizumab, 3% Sucrose, 0.02% PS-80, 10 mM Histidine buffer, pH 5.5, 40 mM Arg, 40 mM Glu | 0.89 | 1.57 | 2.06 |
| H11 | 167 mg/mL pembrolizumab, 3% Sucrose, 0.02% PS-80, 10 mM Histidine buffer, pH 5.5, 10 mM Methionine, 40 mM Arg, 40 mM Glu, 100 pM DTPA | 0.89 | 1.68 | 2.12 |
| H12 | 167 mg/mL pembrolizumab, 7% Sucrose, 0.02% PS-80, 10 mM Histidine buffer, pH 5.5, 10 mM Methionine | 1.06 | 1.99 | 2.70 |
| H13 | 167 mg/mL pembrolizumab, 7% Sucrose, 0.02% PS-80, 10 mM Histidine buffer, pH 5.5, 10 mM Methionine | 1.06 | 2.00 | 2.70 |
| H14 | 167 mg/mL pembrolizumab, 7% Sucrose, 0.02% PS-80, 10 mM Histidine buffer, pH 5.5 | 1.06 | 2.05 | 2.79 |

In this study, the presence of arginine and glutamate (formulations H10 and H11) appeared to have an impact on the rate of aggregation.

Figure 7:
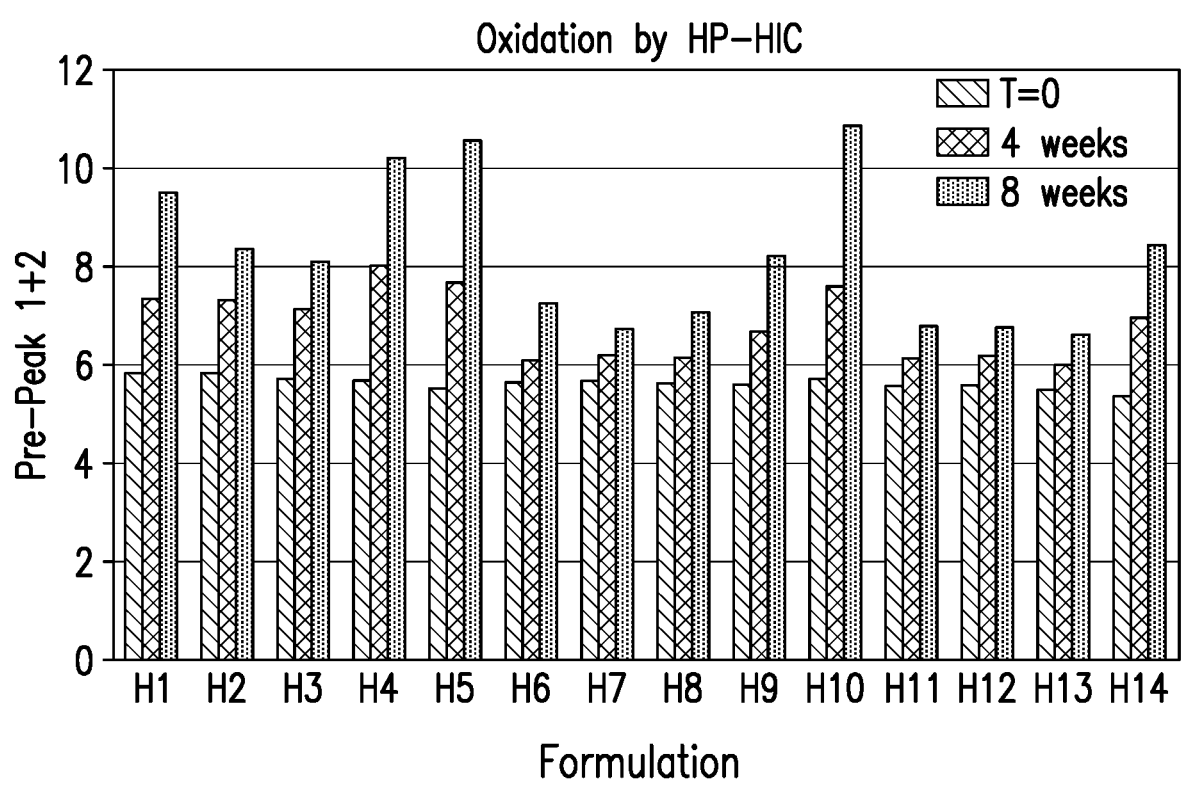
FIG. 7 shows oxidation of Met-105 in the formulations in EXAMPLE 6, Study 3 at 40° C. over an 8-week period as measured by HP-HIC.

Oxidation of the above samples at 40° C. was also measured by HP-HIC over 8 weeks. Results indicate that the presence of 10 mM methionine resulted in a reduced rate of aggregation over the 8-week period compared to other formulations (see FIG. 7).

Overall, studies 1-3 showed that the presence of L methionine in the pembrolizumab formulations was able to reduce the rate of oxidation in a concentration-dependent manner. No additional benefit of adding DTPA and EDTA along with methionine was observed.

Example 7

Viscosity of High Concentration Anti-PD-1 Antibody Formulations

Study 1—Viscosity as a Function of Protein Concentration

Study 1A:

In one experiment, the viscosity of unformulated pembrolizumab (pembrolizumab in 10 mM histidine buffer) as a function of protein concentration was measured. Samples were generated by ultrafiltration/diafiltration of pembrolizumab in 10 mM histidine buffer pH 5.4. Concentration values were measured by SoloVPE and the viscosity was measured using the MVROC instrument. Values are provided in Table 11 below.

TABLE 11

Viscosity of unformulated pembrolizumab (in 10 mM histidine buffer pH 5.5) as a function of protein concentration

| Measured pembrolizumab concentration (mg/mL) | Viscosity at 20° C. (cP) |
|---|---|
| 25 | 1.3 |
| 46 | 1.7 |
| 54.7 | 1.8 |
| 90.2 | 3.1 |
| 135.6 | 7.6 |
| 153.8 | 11.3 |
| 206 | 52.3 |
| 223.4 | 88.1 |
| 234 | 173.4 |
| 263 | 425 |

Study 1B:

In another experiment, the viscosity of pembrolizumab formulated in 10 mM histidine pH 5.5 in the presence of 3% (w/v) arginine as a function of pembrolizumab concentration was also measured. The samples for this experiment were generated by ultrafiltration-diafiltration of pembrolizumab in 10 mM histidine pH 5.4 buffer in the presence of 3% (w/v) arginine. Samples were collected at different stages of UF/DF process and concentration and viscosity values were measured. Concentration values were measured by SoloVPE and the viscosity was measured using an MVROC instrument. Values are provided in Table 12.

TABLE 12

Viscosity of pembrolizumab formulated in 10 mM histidine pH 5.5 in the presence of 3% (w/v) arginine

| Measured pembrolizumab concentration (mg/mL) | Viscosity at 20° C. (cP) |
|---|---|
| 51.6 | 1.8 |
| 93.1 | 3.0 |
| 157.3 | 9.90 |
| 217.3 | 50.9 |
| 288 | 271.0 |

Study 1C:

In another experiment, the viscosity of formulated pembrolizumab samples was measured. Formulations of pembrolizumab were prepared at different concentrations in the range of 100-200 mg/mL with 7% (w/v) sucrose, 0.02% (w/v) polysorbate 80, 10 mM methionine, in 10 mM histidine buffer pH 5.5. The formulations were prepared by mixing the following stock solutions: (1) pembrolizumab drug substance at 236 mg/mL in 10 mM histidine pH 5.5 buffer; (2) 49% (w/w) sucrose, 0.14% (w/w) polysorbate 80, 85 mM methionine in 10 mM histidine pH 5.4; and (3) 10 mM histidine pH 5.5. Viscosity measurements were performed using MVROC viscometer (see Table 13).

TABLE 13

Viscosity of fully formulated pembrolizumab as a function of protein concentration.

| Measured concentration[1] (mg/mL) | Viscosity[2] at 20° C., (cP) |
|---|---|
| 100.2 (0.2) | 4.2 (0.0) |
| 125.6 (0.2) | 7.1 (0.1) |
| 148.1 (0.6) | 13.1 (0.0) |
| 174.8 (0.2) | 26.8 (0.1) |
| 186.1 (1.2) | 34.7 (0.4) |
| 204.1 (1.3) | 54.9 (0.5) |

[1]Concentration values of samples were measured in triplicate via absorption of UV A280 of diluted samples, and the average value along with the standard deviation was reported.

[2]Viscosity values were measured in triplicate and the average value along with the standard deviation was reported.

Study 2. Effect of Different Excipients on Viscosity of High Concentration Pembrolizumab Solutions In this study, stock solutions of different excipients in 10 mM histidine pH 5.5 buffer were prepared. Subsequently, pembrolizumab drug substance samples in 10 mM histidine, pH 5.5 were spiked with these excipient stocks to achieve target excipient concentration. Pembrolizumab concentration values were measured by SoloVPE and the viscosity was measured using an MVROC instrument (Table 14). Sample pH was also measured.

TABLE 14

Effect of different excipients on viscosity of pembrolizumab solutions in 10 mM histidine pH 5.5 (target pH)

| Excipient | Target excipient concentration (unit) | Measured pembrolizumab concentration (mg/mL) | Measured pH[1] | Viscosity[2] (cP) at 20° C. |
|---|---|---|---|---|
| L-Arginine | 200 mM | 183 | 5.5 | 20.29 |
| Poly-arginine (5-15 kDa) | 0.5 mg/mL | 202 | 5.6 | 51.354 |
| Poly-arginine (15-70 kDa) | 0.5 mg/mL | 186 | 5.56 | 54.018 |
| L-Alaninine | 200 mM | 197 | 5.47 | 30.641 |
| L-Cysteine | 200 mM | 187 | 5.56 | 31.844 |
| L-Glutamine | 60 mM | 193 | 5.6 | 53.825 |
| Glycine | 200 mM | 175 | 5.52 | 42.769 |
| L-Histidine | 100 mM | 186 | 5.05 | 19.402 |
| L-Lysine | 200 mM | 179 | 5.52 | 27.431 |
| L-Methionine | 40 mM | 200 | 5.45 | 38.501 |
| O-phospho-L-serine | 30 mM | 151 | 5.56 | 34.42 |
| Potassium Chloride | 200 mM | 195 | 5.59 | 38.246 |
| Sodium Chloride | 200 mM | 208 | 5.69 | 58.192 |
| Calcium Chloride | 200 mM | 178 | 5.56 | 33.593 |
| Potassium Iodide | 200 mM | 180 | 5.7 | 34.626 |
| Sodium Iodide | 200 mM | 197 | 5.77 | 35.92 |
| Guanidine hydrochloride | 200 mM | 189 | 5.61 | 20.984 |
| DMSO | 10% (v/v) | 180 | 5.4 | 13.056 |
| Protamine | 0.75 mg/mL | 180 | 5.54 | 50.328 |
| Camphor-10-sulfonic acid | 200 mM | 191 | 5.64 | 15.698 |
| L-Glutamic acid | 200 mM | 173 | 5.55 | 52.368 |
| Polysorbate 80 | 0.1% (w/v) | 183 | 5.89 | 49.268 |
| Pluronic F127 | 0.1% (w/v) | 179 | 5.85 | 43.908 |
| ATP | 12.5 mg/mL | 173 | 5.73 | 56.695 |

[1]Target pH of all samples was 5.5; however, in certain cases, the pH of the spiking solution influenced the pH of the spiked pembrolizumab samples
[2]The viscosity of control pembrolizumab solution in 10 mM histidine buffer only (non-spiked with any of the excipients) was not measured in this experiment; however, based on the other experiments, it was expected to be ~50 cP Study 3: Effect of Concentration of Arginine, Histidine, and Methionine on Viscosity of Pembrolizumab Solutions In this study, the effect of arginine, histidine, sodium acetate, and methionine concentration on viscosity of pembrolizumab solutions was investigated. Pembrolizumab drug substance (>200 mg/mL) in 10 mM histidine pH 5.4 was mixed with different amounts of stock solutions of arginine, histidine, and methionine to achieve varying concentrations of excipients in solutions containing pembrolizumab target concentrations of 200 mg/mL or 167 mg/mL. The results are summarized in Table 15.

TABLE 15

Effect of Excipient Concentration on Viscosity

| | Target excipient conc. (mM) | Target pembrolizumab concentration - 200 mg/mL | | Target pembrolizumab concentration - 167 mg/mL | |
|---|---|---|---|---|---|
| | | Measured pembrolizumab concentration (mg/mL) | Viscosity at 20° C. (cP) | Measured pembrolizumab concentration (mg/mL) | Viscosity at 20° C. (cP) |
| No Excipient | 0 | 191.6 | 37.847 | 163.4 | 18.512 |
| | 0[1] | 202.5 | 58.7 | — | — |
| L-Arginine HCl | 15 | 193.4 | 37.268 | 164.8 | 17.427 |
| | 30 | 188.2 | 32.976 | 163.6 | 16.206 |
| | 45 | 196.4 | 30.041 | 166.3 | 17.950 |
| | 60 | 191.2 | 28.615 | 161.8 | 12.951 |
| | 75 | 190.7 | 26.697 | 168.7 | 13.758 |
| | 71[1] | 193.3 | 27.1 | — | — |
| | 142[1] | 201.8 | 26.1 | — | — |
| | 213.6[1] | 203.5 | 26.7 | — | — |
| | 285[1] | 205.7 | 26.8 | — | — |
| | 356[1] | 211.7 | 25.6 | — | — |
| | 427[1] | 205.5 | 25.3 | — | — |
| L-Histidine Hydrochloride Monohydrate | 5 | 183.6 | 37.142 | 165.1 | 18.209 |
| | 20 | 189.8 | 20.356 | 164.2 | 16.654 |
| | 35 | 190.1 | 30.337 | 166.4 | 16.877 |
| | 50 | 193.9 | 24.073 | 168.9 | 15.490 |
| | 65 | 190.2 | 27.341 | 166 | 13.303 |

TABLE 15-continued

Effect of Excipient Concentration on Viscosity

|  | | Target pembrolizumab concentration - 200 mg/mL | | Target pembrolizumab concentration - 167 mg/mL | |
| --- | --- | --- | --- | --- | --- |
|  | Target excipient conc. (mM) | Measured pembrolizumab concentration (mg/mL) | Viscosity at 20° C. (cP) | Measured pembrolizumab concentration (mg/mL) | Viscosity at 20° C. (cP) |
| L-Methionine | 10 | 190.8 | 45.544 | 168.7 | 19.708 |
|  | 20 | 188 | 46.901 | 160.8 | 19.926 |
|  | 30 | 191.7 | 45.374 | 161.2 | 18.402 |
|  | 40 | 194.3 | 41.235 | 161.3 | 18.304 |

[1]Value represents data from a separate experiment that evaluated arginine•HCl concentrations up to 9% (w/v) (equivalent to 427 mM)

Data from the studies above demonstrate that viscosity of pembrolizumab in 10 mM histidine buffer pH 5.5 increases exponentially with increase in protein concentration (Table 11). The data also show that the presence of 3% (w/v) arginine reduces the viscosity of pembrolizumab in 10 mM histidine pH 5.5 solution; however, the exponential increase in viscosity with increase in pembrolizumab concentration is still observed (Table 12). Viscosity values of pembrolizumab formulated in 10 mM histidine pH 5.5, along with 7% (w/v) sucrose, 0.02% polysorbate 80, 10 mM methionine in the protein concentration range of 100-200 mg/mL are similar to corresponding values measured in 10 mM pH 5.5 buffer alone. The viscosity of formulated pembrolizumab shows significant increase around 150 mg/mL and higher concentrations (Table 13).

Different excipients impacted viscosity of pembrolizumab high concentration solutions to different extents (Table 14). The excipients that had the greatest impact on pembrolizumab viscosity include L-arginine, L-histidine, guanidine hydrochloride, DMSO, and camphor sulfonic acid (Table 14). In addition, Table 15 shows that L-arginine and L-hisitidine reduce pembrolizumab solution viscosity in a concentration dependent manner and that addition of L-methionine up to 40 mM does not reduce viscosity of pembrolizumab.

Example 8

Long-Term Stability of High Concentration Anti-PD-1 Antibody Formulations

Additional studies were performed to determine the long term stability of high-concentration pembrolizumab formulations in the presence and absence of methionine. This study investigated the impact of concentration and presence of antioxidant (e.g., methionine) on the stability of pembrolizumab. Stock solutions of excipients were prepared and spiked into pembrolizumab drug substance to achieve the final composition presented in the Table 16. The formulations were staged in 5° C.+/−3° C., 25° C.+/−3° C./60%±5% relative humidity and 40° C.+/−2° C./75%±5% relative humidity environmental stability chambers. Formulations K2 and K3 were staged on limited stability compared to formulations K1 and K4. The planned duration of the study is 36 months, with 25° C. ending after six months and 40° C. ending after three months. Results for up to 12 months are presented below.

TABLE 16

Long Term Stability of Formulations Comprising Pembrolizumab

| | Ab Concentration (mg/mL) | | | | Container/ |
| --- | --- | --- | --- | --- | --- |
| Formulation | Target | Actual | Formulation | Fill | closure |
| K1 | 167 | 143 | 10 mM histidine pH 5.5, 7% sucrose, 0.02% PS80 + 10 mM Met | 1.4 mL (label) | 2R vial 12 mM serum stopper |
| K2 | 184 | 161 | | | |
| K3 | 150 | 131 | | | |
| K4 | 167 | 146 | 10 mM histidine pH 5.5, 7% sucrose, 0.02% PS80 | | |

All test formulations were visually inspected and found to be essentially free from visible particles through 12 months at 5° C. The formulations were also evaluated by HP-SEC, HP-HIC and HP-IEX, and results are provided in Tables 17-19 and summarized below:

pH:

All formulations had the same initial pH value of 5.7. No change in the pH was observed for any of the formulations at any storage condition.

Potency by Binding ELISA:

No change was observed in potency by binding ELISA for any of the formulations irrespective of the storage duration and condition. All the potency values were within the acceptance criteria of 60-140% of the reference (values ranged from 85-106 over the 12 month storage period for samples stored at 5° C., data not shown).

Reduced and Non-Reduced CE-SDS:

Purity by CE-SDS was measured under reducing and non-reducing conditions. There was no measurable change in % purity or % intact IgG as a function of time at 5° C. up to 12 months for any of the formulations. At 5° C., the % purity by reducing CE-SDS (heavy chain and light chain) was >96.5% for formulations K1 and K4 through 12 months and ≥97.0% for formulations K2 and K3 over the same time period. At 25° C., there was a small decrease in purity for all the formulations. At 40° C., an expected drop in purity was observed after 3 months for all the formulations. The % purity at 5° C. by non-reducing CE-SDS (intact IgG) was ≥98.2 for formulations K1 and K2, ≥97.1 for formulation K2 and ≥97.2 for formulation K4 through 12 months at the times tested. All results were within the clinical acceptance criteria of ≥90.0% for both reducing and non-reducing CE-SDS.

Purity by HP-SEC:

At the recommended storage condition of 5° C., no measurable changes in % HMW were noticed for any of the formulations up to 12 months from the initial levels. At 25° C. over 6 months, % HMW increased with a corresponding decrease in monomer. No LMW species could be detected at either of the storage conditions for any formulation. At 40° C. over 3 months, % HMW increased for different formulations with a corresponding drop in monomer. For formulations K1-K3, increase in HMW was observed with increase in concentration. LMW species were observed for all formulations at 40° C. at 3 month time point.

Oxidation by HP-HIC:

Oxidation at Methionine 105 was quantified by monitoring pre-peak 1+2 by HP-HIC. Formulations K1-K4 exhibited no change in oxidation at 5° C. over 12 months. At 25° C. over 6 months, the levels of pre-peak 1+2 increased slightly, whereas at 40° C. over 3 months, the increase was more evident. At 25° C. and 40° C., change in oxidation was more pronounced for formulation K4. Since K4 is the only formulation which does not contain L-Methionine, these results demonstrate that inclusion of L-Methionine resulted in a significant decrease in the rate of oxidation.

Charge Heterogeneity by HP-IEX:

Charge heterogeneity was evaluated by monitoring the main peak along with different acidic and basic species. At 5° C. up to 12 months, no measurable changes were found in any of the individual peaks including the main peak for any of the formulations. At 25° C. for 6 months, the main peak decreased. There was an increase in all the acidic species (Acidic variants, Acidic 1, and pre main peak) and basic variants peak. There was a decrease observed in Basic land Basic 2 species. At 40° C. for 3 months, the main peak showed an ever steeper decline. Similar to 25° C., increase was observed for Acidic variants, Acidic 1, pre main and basic variants peak and decrease was observed in Basic 1 and Basic 2 peaks.

Turbidity:

Turbidity of the drug product batches was determined on stability by measuring optical density at 350 nm. There was no measurable change in turbidity at 5° C. for any of the formulations. Samples stored at 25° C. showed a slight increase whereas those stored at 40° C. showed an even larger increase in turbidity. The increase in turbidity at 25° C. and 40° C. is consistent with increasing high molecular weight species observed on stability.

Overall, based on twelve months of stability data, formulations K1-K4 were stable at 5° C. for up to 12 months with no measurable changes in product quality attributes. Some degradation was observed upon monitoring the attributes at 25° C. for 6 months and at 40° C. for 3 months. Stability of products at 5° C. will be further evaluated up to a duration of 36 months.

TABLE 17

Stability Data for Formulations K1-K4 at 5° C.

| Test Time Interval | Form. | Stability Test Interval | | | | | |
|---|---|---|---|---|---|---|---|
| | | Initial | 1 mo. | 3 mos. | 6 mos. | 9 mos. | 12 mos. |
| Purity by HP-SEC | | | | | | | |
| High Molecular Weight Species (%) | K1 | 1.4 | 1.4 | 1.5 | 1.4 | 1.4 | 1.4 |
| | K2 | 1.5 | N.A. | N.A. | 1.5 | N.A. | 1.5 |
| | K3 | 1.5 | N.A. | N.A. | 1.4 | N.A. | 1.4 |
| | K4 | 1.5 | 1.5 | 1.6 | 1.5 | 1.5 | 1.5 |
| % Monomer | K1 | 98.5 | 98.5 | 98.5 | 98.5 | 98.5 | 98.5 |
| | K2 | 98.5 | N.A. | N.A. | 98.5 | N.A. | 98.5 |
| | K3 | 98.5 | N.A. | N.A. | 98.6 | N.A. | 98.5 |
| | K4 | 98.5 | 98.5 | 98.4 | 98.5 | 98.5 | 98.5 |
| Low Molecular Weight Species (%) | K1 | 0 | 0 | 0 | <RL[1] | <RL[1] | <RL[1] |
| | K2 | 0 | N.A. | N.A. | <RL[1] | N.A. | <RL[1] |
| | K3 | 0 | N.A. | N.A. | <RL[1] | N.A. | <RL[1] |
| | K4 | 0 | 0 | 0 | <RL[1] | <RL[1] | <RL[1] |
| Oxidation by HP-HIC | | | | | | | |
| Pre-peak 1 & 2 (%) | K1 | 6.26 | 6.34 | 6.50 | 6.35 | 6.05 | 5.73 |
| | K2 | 6.28 | N.A. | N.A. | 6.38 | N.A. | 5.75 |
| | K3 | 6.40 | N.A. | N.A. | 6.36 | N.A. | 5.78 |
| | K4 | 6.36 | 6.58 | 6.86 | 6.64 | 6.31 | 6.15 |
| Group Charge Variants by HP-IEX | | | | | | | |
| Acidic Variants (%) | K1 | 16.8 | 16.8 | 17.4 | 17.3 | 17.2 | 17.5 |
| | K2 | 16.8 | N.A. | N.A. | 17.3 | N.A. | 17.5 |
| | K3 | 16.9 | N.A. | N.A. | 17.4 | N.A. | 17.4 |
| | K4 | 16.8 | 16.9 | 17.6 | 17.3 | 17.3 | 17.5 |
| Main (%) | K1 | 59.5 | 59.4 | 59.2 | 59.4 | 59.6 | 58.7 |
| | K2 | 59.5 | N.A. | N.A. | 59.4 | N.A. | 58.7 |
| | K3 | 59.5 | N.A. | N.A. | 59.4 | N.A. | 58.8 |
| | K4 | 59.5 | 59.4 | 59.1 | 59.6 | 59.5 | 58.6 |

TABLE 17-continued

Stability Data for Formulations K1-K4 at 5° C.

| Test Time Interval | Form. | Initial | 1 mo. | 3 mos. | 6 mos. | 9 mos. | 12 mos. |
|---|---|---|---|---|---|---|---|
| Basic Variants (%) | K1 | 23.8 | 23.8 | 23.4 | 23.3 | 23.2 | 23.7 |
| | K2 | 23.7 | N.A. | N.A. | 23.3 | N.A. | 23.8 |
| | K3 | 23.7 | N.A. | N.A. | 23.2 | N.A. | 23.8 |
| | K4 | 23.7 | 23.7 | 23.3 | 23.1 | 23.2 | 23.8 |
| Turbidity (A350) | K1 | 0.187 | 0.185 | 0.190 | 0.189 | 0.192 | 0.200 |
| | K2 | 0.200 | N.A. | N.A. | 0.207 | N.A. | 0.213 |
| | K3 | 0.174 | N.A. | N.A. | 0.183 | N.A. | 0.191 |
| | K4 | 0.189 | 0.187 | 0.193 | 0.190 | 0.191 | 0.202 |

[1]<RL: Below reporting limit

TABLE 18

Stability Data for Formulations K1-K4 at 25° C.

| Test Time Interval | | Form. | Initial | 1 month | 3 months | 6 months |
|---|---|---|---|---|---|---|
| Purity by HP-SEC | High Molecular Weight Species (%) | K1 | 1.4 | 1.5 | 1.7 | 1.8 |
| | | K2 | 1.5 | N.A. | 1.8 | 1.9 |
| | | K3 | 1.5 | N.A. | 1.7 | 1.8 |
| | | K4 | 1.5 | 1.6 | 1.8 | 1.9 |
| | % Monomer | K1 | 98.5 | 98.5 | 98.2 | 98.1 |
| | | K2 | 98.5 | N.A. | 98.2 | 98.1 |
| | | K3 | 98.5 | N.A. | 98.3 | 98.2 |
| | | K4 | 98.5 | 98.4 | 98.1 | 98.0 |
| | Low Molecular Weight Species (%) | K1 | 0 | 0 | 0 | <RL[1] |
| | | K2 | 0 | N.A. | 0 | <RL[1] |
| | | K3 | 0 | N.A. | 0 | <RL[1] |
| | | K4 | 0 | 0 | 0 | <RL[1] |
| Oxidation by HP-HIC | Pre-peak 1 & 2 (%) | K1 | 6.26 | 6.43 | 6.86 | 7.15 |
| | | K2 | 6.28 | N.A. | 6.88 | 7.15 |
| | | K3 | 6.4 | N.A. | 7.06 | 7.12 |
| | | K4 | 6.36 | 7.08 | 8.04 | 8.74 |
| Group Charge Variants by HP-IEX | Acidic Variants (%) | K1 | 16.8 | 18.5 | 24.3 | 30.8 |
| | | K2 | 16.8 | N.A. | 23.7 | 30.8 |
| | | K3 | 16.9 | N.A. | 23.8 | 30.8 |
| | | K4 | 16.8 | 18.6 | 23.6 | 30.9 |
| | Main (%) | K1 | 59.5 | 58.7 | 54.7 | 50.3 |
| | | K2 | 59.5 | N.A. | 55.4 | 50.3 |
| | | K3 | 59.5 | N.A. | 55.3 | 50.3 |
| | | K4 | 59.5 | 58.4 | 55.6 | 50.2 |
| | Basic Variants (%) | K1 | 23.8 | 22.9 | 21.0 | 18.9 |
| | | K2 | 23.7 | N.A. | 20.8 | 18.9 |
| | | K3 | 23.7 | N.A. | 20.9 | 18.9 |
| | | K4 | 23.7 | 23.0 | 20.8 | 18.9 |
| Turbidity (A350) | | K1 | 0.187 | 0.197 | 0.217 | 0.231 |
| | | K2 | 0.200 | N.A. | 0.233 | 0.242 |
| | | K3 | 0.174 | N.A. | 0.200 | 0.212 |
| | | K4 | 0.189 | 0.199 | 0.219 | 0.244 |

[1]<RL: Below reporting limit, N/A: not available

TABLE 19

Stability Data for Formulations K1-K4 at 40° C.

| Test Time Interval | | Form. | Initial | 1 month | 3 months |
|---|---|---|---|---|---|
| Purity by HP-SEC | High Molecular Weight Species (%) | K1 | 1.4 | 2.5 | 4.9 |
| | | K2 | 1.5 | N.A. | 5.2 |
| | | K3 | 1.5 | N.A. | 4.6 |
| | | K4 | 1.5 | 2.6 | 5.4 |
| | % Monomer | K1 | 98.5 | 97.5 | 94.9 |
| | | K2 | 98.5 | N.A. | 94.7 |
| | | K3 | 98.5 | N.A. | 95.2 |
| | | K4 | 98.5 | 97.4 | 94.5 |
| | Low Molecular Weight Species (%) | K1 | 0 | 0 | 0.2 |
| | | K2 | 0 | N.A. | 0.2 |
| | | K3 | 0 | N.A. | 0.2 |
| | | K4 | 0 | 0 | 0.2 |
| Oxidation by HP-HIC | Pre-peak 1 & 2 (%) | K1 | 6.26 | 7.32 | 9.28 |
| | | K2 | 6.28 | N.A. | 9.25 |
| | | K3 | 6.4 | N.A. | 9.04 |
| | | K4 | 6.36 | 8.59 | 12.91 |
| Group Charge Variants by HP-IEX | Acidic Variants (%) | K1 | 16.8 | 32.6 | 58.1 |
| | | K2 | 16.8 | N.A. | 58.5 |
| | | K3 | 16.9 | N.A. | 58.5 |
| | | K4 | 16.8 | 33.1 | 58.4 |
| | Main (%) | K1 | 59.5 | 47.8 | 27.8 |
| | | K2 | 59.5 | N.A. | 27.7 |
| | | K3 | 59.5 | N.A. | 28.0 |
| | | K4 | 59.5 | 47.3 | 27.8 |
| | Basic Variants (%) | K1 | 23.8 | 19.6 | 14.0 |
| | | K2 | 23.7 | N.A. | 13.8 |
| | | K3 | 23.7 | N.A. | 13.6 |
| | | K4 | 23.7 | 19.6 | 13.8 |
| Turbidity (A350) | | K1 | 0.187 | 0.231 | 0.322 |
| | | K2 | 0.200 | N.A. | 0.357 |
| | | K3 | 0.174 | N.A. | 0.302 |
| | | K4 | 0.189 | 0.234 | 0.347 |

[1]<RL: Below reporting limit,
N/A: not available

Examples 9-13

Examples (9-13) highlight the preparation of formulations that use a smaller amount of antibody and excipients than intended in the final formulations. However these formulations preserve the molar ratio of the pembrolizumab/stabilizer and pembrolizumab/surfactant of the final intended formulations. The anti-oxidant, buffer and metal chelator concentrations were tested at the final intended concentration. The pembrolizumab (5 mg/mL), PS80 (0.0016%) and stabilizer (e.g., 1.4% sucrose) concentrations were scaled down by a factor of 5 and studied as surrogate formulations for the more concentrated, final intended formulations. For example, Formulation 1A in Table 20 has the same molar ratios as a formulation comprising 25 mg/mL pembrolizumab, 7% sucrose and 0.02% PS80. It is expected that the formulations disclosed in Examples 9-12 are representative of the intended final formulations and that the disclosed results suggest how the final higher concentration formulations would behave. It is understood that some parameters being studied, e.g. aggregation, may be impacted by the decrease in concentration due to a decreased likelihood of intermolecular interactions; however, to compensate, a more aggressive stability regimen was pursued (50° C. for 10 days) to induce and identify stability risk.

The concentration of anti-oxidant (e.g. methionine), buffer (e.g. histidine) and metal chelator (e.g. DTPA and EDTA) concentrations were not scaled down in a similar manner to the other excipients. Methionine is a functional excipient that is used to reduce the Met-105 oxidation by expunging oxidants (such as dissolved oxygen), thus maintaining the chemical stability of pembrolizumab. Similarly, DTPA is a functional excipient that is used to complex metal ion impurities which may otherwise trigger undesired protein degradation. Since it is more challenging to maintain chemical stability at lower pembrolizumab concentrations, the methionine and DTPA concentrations were held constant at 10 mM and 20 μM, respectively. It is expected that if a specific amount of methionine is effective in the low concentration formulations, it would most likely be as effective at preventing oxidation in the higher concentration formulations. L-Histidine and/or L-Histidine hydrochloride at 10 mM is expected to maintain buffering capacity at the intended pH of the formulations tested.

Example 9

Evaluation of the Stability of Low Concentration Pembrolizumab Formulations in Combination with Methionine An initial formulation study was performed to evaluate the stability of formulations comprising a low (5 mg/ml) concentration of pembrolizumab and to evaluate the impact of different formulation excipients. Throughout Examples 9-12, the arginine used was L-arginine or L-arginine-HCl, the glycine used was glycine and the proline used was L-proline.

Pembrolizumab drug substance in 10 mM Histidine pH 5.5 (41.2 mg/mL) was combined with polysorbate-80 (PS80) solution (~0.36 mg/mL) then QS to final volume with buffer to yield a protein (20 mg/mL)/PS80 (0.16 mg/mL) stock solution in 10 mM histidine pH 5.5. Pembrolizumab formulations were prepared to 5 mg/mL target concentration by spiking the protein/PS80 stock solution with excipient stock solutions and respective buffer. All stock solutions used for formulations were filtered through Millapore Express® PLUS Stericup® 0.22 μm PES filters prior to use. Test formulations comprising a low concentration of pembrolizumab were prepared in a 96-well plate at a volume of 1 mL. Excipients were spiked into the protein/PS80 stock solution to achieve target levels of each excipient and brought to final volume using histidine buffer pH 5.5 (see Table 20). (2-Hydroxypropyl)-β-cyclodextrin (sold under the name CAVITRON™) and (sulfobutylether)-β-cyclodextrin (sold under the trade name CAPTISOL™) are denoted as HPBC and SBEC, respectively. The well plate was covered with a 96-well silicone sealing mat and then was vacuum sealed (2×) in moisture barrier bags to minimize potential evaporation. Samples were staged in 2-8° C. (as used herein and throughout the Examples, the term "5° C." is used interchangeably with "2-8° C.", which indicates 5° C.±3° C. (standard deviation)) and 50° C. environmental stability chambers.

TABLE 20

Low Concentration Pembrolizumab Formulations.

| Form.[1] | Stabilizer | Anti-Oxidant |
|---|---|---|
| 1A | 1.4% sucrose | — |
| 1B | 1.4% sucrose | 10 mM Met |
| 2A | 0.8% mannitol | — |
| 2B | 0.8% mannitol | 10 mM Met |
| 3A | 1.4% trehalose | — |
| 3B | 1.4% trehalose | 10 mM Met |
| 4A | 0.8% sorbitol | — |
| 4B | 0.8% sorbitol | 10 mM Met |
| 5A | 0.4% glycine | — |
| 5B | 0.4% glycine | 10 mM Met |
| 6A | 1.4% HPBC | — |
| 6B | 1.4% HPBC | 10 mM Met |
| 7A | 0.8% arginine | — |
| 7B | 0.8% arginine | 10 mM Met |
| 8A | 0.8% proline | — |
| 8B | 0.8% proline | 10 mM Met |
| 9A | 0.8% SBEC | — |
| 9B | 0.8% SBEC | 10 mM Met |

[1]All formulations comprised 5 mg/mL pembrolizumab, 10 mM Histidine buffer and 0.004% PS80, in addition to the excipients listed.

Each of the test formulations were visually inspected for changes in coloration or precipitate formation (data not shown). Additionally, stability of the formulations was evaluated using turbidity (A350), UP-SEC (to assess purity) and HP-IEX (charge profile) after the 10-day stability period. Formulations 9A and 9B comprising SBEC were visibly turbid upon removal from the stability chamber. On the contrary, formulations 6A and 6B, comprising HPBC, did not show any visible signs of turbidity. Formulations 9A and 9B were not tested further by UP-SEC and HP-IEX, only turbidity, as highlighted in Table 21. UP-SEC results demonstrate that there were no changes for any of the formulations that were stored at 5° C. during the 10-day time period with the exception of formulations comprising arginine (with or without methionine), where a slight decrease in % mAb was observed by UP-SEC (<0.5%). All other formulations were considered stable at the 5° C. storage condition. At 50° C., more pronounced changes were observed via UP-SEC (a decrease in % mAb) and HP-IEX (a decrease in % main and a significant increase in % pre-main, data not shown) for each of the formulations over the time period tested. Surprisingly, the highest decrease in % mAb (with corresponding increase in % aggregates) by UP-SEC after 10 days was observed with formulations 7A and 7B at 50° C. compared to the other formulations stored at 50° C. for 10 days, suggesting that these formulations have decreased stability. Turbidity (A350) results for formulations 7A and 7B after 10 days at 50° C. corroborated the UP-SEC results indicating a decrease in stability of formulations 7A and 7B.

Cyclodextrins have been shown to stabilize protein formulations in the literature through maximizing both conformational and colloidal stability; however, cyclodextrins have been primarily studied with IgG1 proteins. The mechanism by which cyclodextrins impart this stabilization is the subject of much debate. As shown in Table 21, turbidity and UP-SEC measurements of formulations 6A and 6B (comprising HPBC) demonstrated stability that was on par with other stabilizers tested over 10 days 50° C., unlike other cyclodextrin formulations tested (9A and 9B, comprising SBEC), which had high turbidity after 10 days at 50° C.

There were no appreciable differences in charge profile among any of the formulations (with the exclusion of 7A/B and 9A/B which were not tested) at 50° C. for the 10-day testing period (data not shown). The addition of methionine (10 mM) to the tested formulations had a negligible effect on the prevention of aggregation through the testing period.

TABLE 21

Formulations used for Example 9.

| Form. | Stabilizer | Anti-Oxidant | % mAb ( UP-SEC) 10 days @ 5° C. | 10 days @ 50° C. | Turbidity (A350) 10 days @ 50° C. |
|---|---|---|---|---|---|
| 1A | 1.4% sucrose | — | 99.1 | 96.0 | 0.017 |
| 1B | 1.4% sucrose | 10 mM Met | 99.1 | 96.1 | 0.015 |
| 2A | 0.8% mannitol | — | 99.1 | 96.0 | 0.014 |
| 2B | 0.8% mannitol | 10 mM Met | 99.1 | 96.1 | 0.015 |
| 3A | 1.4% trehalose | — | 99.1 | 96.0 | 0.015 |
| 3B | 1.4% trehalose | 10 mM Met | 99.1 | 96.1 | 0.017 |
| 4A | 0.8% sorbitol | — | 99.1 | 95.9 | 0.017 |
| 4B | 0.8% sorbitol | 10 mM Met | 99.1 | 96.1 | 0.015 |
| 5A | 0.4% glycine | — | 99.0 | 96.1 | 0.018 |
| 5B | 0.4% glycine | 10 mM Met | 99.1 | 96.2 | 0.021 |
| 6A | 1.4% HPBC | — | 99.1 | 95.7 | 0.019 |
| 6B | 1.4% HPBC | 10 mM Met | 99.1 | 95.8 | 0.015 |
| 7A | 0.8% arginine | — | 98.7 | 60.3 | 0.091 |
| 7B | 0.8% arginine | 10 mM Met | 98.6 | 65.3 | 0.068 |
| 8A | 0.8% proline | — | 99.1 | 95.2 | 0.016 |
| 8B | 0.8% proline | 10 mM Met | 99.1 | 95.3 | 0.021 |
| 9A | 0.8% SBEC | — | DNT | DNT | 0.134 |
| 9B | 0.8% SBEC | 10 mM Met | DNT | DNT | 0.134 |

[1]All formulations comprised 5 mg/mL pembrolizumab, 10 mM Histidine buffer and 0.004% PS80, in addition to the excipients listed.

Example 10

Analysis of Low Concentration Pembrolizumab Formulations Comprising Methionine in Combination with Metal Chelators In order to investigate the impact of metal chelators (DTPA and EDTA) on low concentration pembrolizumab formulations, a series of compositions were formulated and tested as described below. Pembrolizumab (20 mg/mL)/PS80 (0.16 mg/mL) stock solution in 10 mM histidine pH 5.5 was prepared as described above in Example 9. Formulations 1-8 (C through F) were prepared in a 96-well plate by spiking stock solutions of the following excipients: sucrose (5% w/v), mannitol (5% w/v), trehalose (5% w/v), sorbitol (5% w/v), glycine (5% w/v), HPBC (5% w/v), arginine (5% w/v), proline (5% w/v), methionine (2% w/v), DTPA (0.01% w/v), and EDTA (0.01% w/v) into pembrolizumab/PS80 stock solution to achieve the target compositions (QS to 1 mL with histidine pH 5.5 buffer) listed in Table 22. All stock solutions used for formulations were filtered through Millapore Express® PLUS Stericup® 0.22 μm PES filters prior to use. The well plate was covered with a 96-well silicone sealing mat and then was vacuum sealed (2×) in moisture barrier bags to minimize potential evaporation. Samples were staged in 5° C. and 50° C. environmental stability chambers for time period of 10 days.

TABLE 22

Low Concentration Pembrolizumab Formulations Comprising Methionine in Combination with DTPA and EDTA.

| Form.[1] | Stabilizer | Anti-Oxidant | Metal Chelator |
|---|---|---|---|
| 1C | 1.4% sucrose | — | DTPA |
| 1D | 1.4% sucrose | 10 mM Met | DTPA |
| 1E | 1.4% sucrose | — | EDTA |
| 1F | 1.4% sucrose | 10 mM Met | EDTA |
| 2C | 0.8% mannitol | — | DTPA |
| 2D | 0.8% mannitol | 10 mM Met | DTPA |
| 2E | 0.8% mannitol | — | EDTA |
| 2F | 0.8% mannitol | 10 mM Met | EDTA |
| 3C | 1.4% trehalose | — | DTPA |
| 3D | 1.4% trehalose | 10 mM Met | DTPA |
| 3E | 1.4% trehalose | — | EDTA |
| 3F | 1.4% trehalose | 10 mM Met | EDTA |
| 4C | 0.8% sorbitol | — | DTPA |
| 4D | 0.8% sorbitol | 10 mM Met | DTPA |
| 4E | 0.8% sorbitol | — | EDTA |
| 4F | 0.8% sorbitol | 10 mM Met | EDTA |
| 5C | 0.4% glycine | — | DTPA |
| 5D | 0.4% glycine | 10 mM Met | DTPA |
| 5E | 0.4 % glycine | — | EDTA |
| 5F | 0.4 % glycine | 10 mM Met | EDTA |
| 6C | 1.4% HPBC | — | DTPA |
| 6D | 1.4% HPBC | 10 mM Met | DTPA |
| 6E | 1.4% HPBC | — | EDTA |
| 6F | 1.4% HPBC | 10 mM Met | EDTA |
| 7C | 0.8% arginine | — | DTPA |
| 7D | 0.8% arginine | 10 mM Met | DTPA |
| 7E | 0.8% arginine | — | EDTA |
| 7F | 0.8% arginine | 10 mM Met | EDTA |
| 8C | 0.8% proline | — | DTPA |
| 8D | 0.8% proline | 10 mM Met | DTPA |
| 8E | 0.8% proline | — | EDTA |
| 8F | 0.8% proline | 10 mM Met | EDTA |
| 9C | 0.8% SBEC | — | DTPA |
| 9D | 0.8% SBEC | 10 mM Met | DTPA |

TABLE 22-continued

Low Concentration Pembrolizumab Formulations Comprising
Methionine in Combination with DTPA and EDTA.

| Form.[1] | Stabilizer | Anti-Oxidant | Metal Chelator |
|---|---|---|---|
| 9E | 0.8% SBEC | — | EDTA |
| 9F | 0.8% SBEC | 10 mM Met | EDTA |

[1]All formulations comprised 5 mg/mL pembrolizumab, 10 mM Histidine buffer and 0.004% PS80, in addition to the excipients listed.

Each of the test formulations was visually inspected for any change in color or precipitate over the course of the 10 day testing period (data not shown). Similar to results in Example 9, formulations comprising SBEC were visibly turbid once removed from the stability chamber after 10 days @ 50° C. Again, turbidity measurements (data not shown) support the decreased stability of these formulations in comparison to other formulations tested. As a result, formulations 9C-9F were not subjected to further testing. For the remaining formulations, results from turbidity and UP-SEC measurements were very similar to results listed in Table 21 (with the exclusion of formulations comprising arginine (7C-7F)), suggesting little to no influence of the addition of a metal chelator on stability over 10 days at 50° C. See Table 23. Again, formulations comprising arginine (7C-7F) showed the largest change in % mAb (monomer) and highest turbidity values (data not shown) over the stability time period. Even though formulations 7C-7F showed a very appreciable difference in % mAb, the UP-SEC results for 7D and 7F demonstrate the added benefit of incorporating a metal chelator in combination with methionine to inhibit aggregation. The combination of methionine and EDTA (7F) resulted in a slightly higher % mAb than the combination of methionine and DTPA (7D). There were no appreciable differences in charge profile among any of the formulations (with the exclusion of 7C-7F which were not tested) at 50° C. for the 10-day testing period (data not shown).

TABLE 23

Low Concentration Pembrolizumab Formulations Comprising
Methionine in Combination with DTPA and EDTA.

| Form. | Stabilizer | Anti-Oxidant | Metal Chelator | % mAb (UP-SEC) 10 d/ 5° C. | % mAb (UP-SEC) 10 d/ 50° C. |
|---|---|---|---|---|---|
| 1C | 1.4% sucrose | — | DTPA | 99.1 | 95.9 |
| 1D | 1.4% sucrose | 10 mM Met | DTPA | 99.1 | 96.0 |
| 1E | 1.4% sucrose | — | EDTA | 99.1 | 95.9 |
| 1F | 1.4% sucrose | 10 mM Met | EDTA | 99.1 | 96.0 |
| 2C | 0.8% mannitol | — | DTPA | 99.1 | 95.9 |
| 2D | 0.8% mannitol | 10 mM Met | DTPA | 99.1 | 95.9 |
| 2E | 0.8% mannitol | — | EDTA | 99.0 | 95.9 |
| 2F | 0.8% mannitol | 10 mM Met | EDTA | 99.1 | 95.9 |
| 3C | 1.4% trehalose | — | DTPA | 99.1 | 95.8 |
| 3D | 1.4% trehalose | 10 mM Met | DTPA | 99.1 | 96.0 |
| 3E | 1.4% trehalose | — | EDTA | 99.1 | 96.0 |
| 3F | 1.4% trehalose | 10 mM Met | EDTA | 99.1 | 96.0 |
| 4C | 0.8% sorbitol | — | DTPA | 99.1 | 95.9 |
| 4D | 0.8% sorbitol | 10 mM Met | DTPA | 99.1 | 95.9 |
| 4E | 0.8% sorbitol | — | EDTA | 99.1 | 96.0 |
| 4F | 0.8% sorbitol | 10 mM Met | EDTA | — | — |
| 5C | 0.4% glycine | — | DTPA | 99.1 | 95.9 |
| 5D | 0.4% glycine | 10 mM Met | DTPA | 99.1 | 96.0 |
| 5E | 0.4% glycine | — | EDTA | 99.1 | 96.0 |
| 5F | 0.4% glycine | 10 mM Met | EDTA | 99.1 | 96.1 |
| 6C | 1.4% HPBC | — | DTPA | 99.1 | 94.9 |
| 6D | 1.4% HPBC | 10 mM Met | DTPA | 99.1 | 95.0 |
| 6E | 1.4% HPBC | — | EDTA | 99.1 | 94.9 |
| 6F | 1.4% HPBC | 10 mM Met | EDTA | 99.1 | 95.0 |
| 7C | 0.8% arginine | — | DTPA | 98.7 | 66.9 |
| 7D | 0.8% arginine | 10 mM Met | DTPA | 98.5 | 69.7 |
| 7E | 0.8% arginine | — | EDTA | 98.7 | 66.6 |
| 7F | 0.8% arginine | 10 mM Met | EDTA | 98.5 | 70.1 |
| 8C | 0.8% proline | — | DTPA | 99.1 | 95.1 |
| 8D | 0.8% proline | 10 mM Met | DTPA | 99.1 | 95.2 |
| 8E | 0.8% proline | — | EDTA | 99.1 | 95.0 |
| 8F | 0.8% proline | 10 mM Met | EDTA | 99.1 | 95.0 |
| 9C | 0.8% SBEC | — | DTPA | DNT[1] | |
| 9D | 0.8% SBEC | 10 mM Met | DTPA | | |
| 9E | 0.8% SBEC | — | EDTA | | |
| 9F | 0.8% SBEC | 10 mM Met | EDTA | | |

[1]Did not test.

Example 11

Evaluation of the Effect of pH on the Stability of Low Concentration Pembrolizumab Formulations in Combination with Methionine A further study was performed to evaluate the stability of formulations in histidine buffer at different pH values. In this study, histidine buffers at pH values of 4.5, 6.0 and 6.4 were evaluated and the impact on stability of pembrolizumab was evaluated.

For this study, pembrolizumab drug product formulations were prepared at a concentration of 5 mg/mL in a 96-well plate. Pembrolizumab (20 mg/mL)/PS80 (0.16 mg/mL) stock solutions in 10 mM histidine at pH values of 4.5, 6.0 and 6.4 were prepared from pembrolizumab/PS80 stock solution pH 5.5 by adjusting the pH with dilute HCl or NaOH to the target pH. Excipient stock solutions were adjusted to the target pH in a similar manner and were filtered through Millapore Express® PLUS Stericup® 0.22 μm PES filters prior to use. The following excipient stock solutions were spiked into the pembrolizumab (20 mg/mL)/PS80 (0.16 mg/mL) stock solutions to achieve the target concentrations listed in Table 24: sucrose (5% w/v), mannitol (5% w/v), trehalose (5% w/v), sorbitol (5% w/v), glycine (5% w/v), HPBC (5% w/v), arginine (5% w/v), proline (5% w/v), and methionine (2% w/v). The well plate was covered with a 96-well silicone sealing mat and then was vacuum sealed (2×) in moisture barrier bags to minimize potential evaporation. Samples were staged in 5° C. and 50° C. environmental stability chambers for time period of 10 days.

TABLE 24

Pembrolizumab Formulations Comprising Methionine at Various pH Values.

| Form.[1] | Stabilizer | Anti-Oxidant | pH |
|---|---|---|---|
| 1G | 1.4% sucrose | — | 4.5 |
| 1H | 1.4% sucrose | 10 mM Met | 4.5 |
| 1J | 1.4% sucrose | — | 6.0 |
| 1K | 1.4% sucrose | 10 mM Met | 6.0 |
| 1L | 1.4% sucrose | — | 6.4 |
| 1M | 1.4% sucrose | 10 mM Met | 6.4 |
| 2G | 0.8% mannitol | — | 4.5 |
| 2H | 0.8% mannitol | 10 mM Met | 4.5 |
| 2J | 0.8% mannitol | — | 6.0 |
| 2K | 0.8% mannitol | 10 mM Met | 6.0 |
| 2L | 0.8% mannitol | — | 6.4 |
| 2M | 0.8% mannitol | 10 mM Met | 6.4 |
| 3G | 1.4% trehalose | — | 4.5 |
| 3H | 1.4% trehalose | 10 mM Met | 4.5 |
| 3J | 1.4% trehalose | — | 6.0 |
| 3K | 1.4% trehalose | 10 mM Met | 6.0 |
| 3L | 1.4% trehalose | — | 6.4 |
| 3M | 1.4% trehalose | 10 mM Met | 6.4 |
| 4G | 0.8% sorbitol | — | 4.5 |
| 4H | 0.8% sorbitol | 10 mM Met | 4.5 |
| 4J | 0.8% sorbitol | — | 6.0 |
| 4K | 0.8% sorbitol | 10 mM Met | 6.0 |
| 4L | 0.8% sorbitol | — | 6.4 |
| 4M | 0.8% sorbitol | 10 mM Met | 6.4 |
| 5G | 0.4% glycine | — | 4.5 |
| 5H | 0.4% glycine | 10 mM Met | 4.5 |
| 5J | 0.4% glycine | — | 6.0 |
| 5K | 0.4% glycine | 10 mM Met | 6.0 |
| 5L | 0.4% glycine | — | 6.4 |
| 5M | 0.4% glycine | 10 mM Met | 6.4 |
| 6G | 1.4% HPBC | — | 4.5 |
| 6H | 1.4% HPBC | 10 mM Met | 4.5 |
| 6J | 1.4% HPBC | — | 6.0 |
| 6K | 1.4% HPBC | 10 mM Met | 6.0 |
| 6L | 1.4% HPBC | — | 6.4 |
| 6M | 1.4% HPBC | 10 mM Met | 6.4 |
| 7G | 0.8% arginine | — | 4.5 |
| 7H | 0.8% arginine | 10 mM Met | 4.5 |
| 7J | 0.8% arginine | — | 6.0 |
| 7K | 0.8% arginine | 10 mM Met | 6.0 |
| 7L | 0.8% arginine | — | 6.4 |
| 7M | 0.8% arginine | 10 mM Met | 6.4 |
| 8G | 0.8% proline | — | 4.5 |
| 8H | 0.8% proline | 10 mM Met | 4.5 |
| 8J | 0.8% proline | — | 6.0 |
| 8K | 0.8% proline | 10 mM Met | 6.0 |
| 8L | 0.8% proline | — | 6.4 |
| 8M | 0.8% proline | 10 mM Met | 6.4 |

[1]All formulations comprised 5 mg/mL pembrolizumab, 10 mM Histidine buffer and 0.004% PS80, in addition to the formulation excipients listed in the Table.

The formulations were evaluated by visual observation, turbidity (A350), UP-SEC (purity), and HP-IEX (charge profile). After the 10 day test period at 50° C., formulations comprising arginine at pH 4.5 (7G & 7H) were visibly turbid. All other formulations listed in Table 24 showed no visual signs of aggregation. Turbidity (A350) values were measured after 10 days and are shown in Table 25. The measured turbidity values for formulations at pH 6.0 were consistently lower than those measured at pH 4.5 and 6.4, suggesting increased stability at pH 6.0. A trend in increased turbidity was observed for all formulations at pH 6.4. Purity of the formulations was tested after 10 days at 50° C. by UP-SEC. All formulations at pH 4.5 showed a significant decrease in % mAb (data not shown) with a corresponding increase in % aggregates (HMW). For all formulations tested at the various pH values, the addition of methionine to the formulation resulted in less aggregation after 10 days at 50° C., with the largest changes being observed in all formulations at pH 4.5. Surprisingly, formulations 5G and 5H were significantly better than the baseline formulation and showed the smallest % change in % mAb (and smallest subsequent increase in % aggregates) over the stability time period, suggesting relatively increased stability of these formulations over other formulations at pH 4.5.

Charge profile of formulations after 10 days at 50° C. was determined by HP-IEX (data not shown). All formulations at a respective pH showed similar charge profiles for each stabilizer tested. Formulations at pH 4.5 showed the lowest % acidic and % pre-main peaks after the stability time period, albeit with a corresponding significant increase in % basic variants (>30%). The charge profiles of formulations at pH 6.0 were comparable to those in Example 9 (Histidine pH 5.5). Formulations at pH 6.4 showed charge profiles opposite to those at pH 4.5 where a significant change in % acidic variants (>30%) was observed with only a small increase in % pre-main peak. The % main peak in all formulations was very similar for all formulations regardless of pH (41-43%). The addition of methionine to the formulations did not result in any significant change in charge profile.

TABLE 25

Low Concentration Pembrolizumab Formulations
Comprising Methionine at Various pH Values.

| Form. | Stabilizer | Anti-Oxidant | pH | % Aggregates (UP-SEC) 10 days/ 5° C. | % Aggregates (UP-SEC) 10 days/ 50° C. | Turbidity (A350) |
|---|---|---|---|---|---|---|
| 1G | 1.4% sucrose | — | 4.5 | 2.76 | 54.57 | 0.021 |
| 1H | 1.4% sucrose | 10 mM Met | 4.5 | 2.77 | 50.72 | 0.019 |
| 1J | 1.4% sucrose | — | 6.0 | 0.99 | 3.69 | 0.017 |
| 1K | 1.4% sucrose | 10 mM Met | 6.0 | 0.90 | 3.21 | 0.015 |
| 1L | 1.4% sucrose | — | 6.4 | 4.09 | 6.14 | 0.029 |
| 1M | 1.4% sucrose | 10 mM Met | 6.4 | 3.85 | 5.67 | 0.024 |
| 2G | 0.8% mannitol | — | 4.5 | 2.78 | 55.49 | 0.021 |
| 2H | 0.8% mannitol | 10 mM Met | 4.5 | 2.76 | 52.06 | 0.018 |
| 2J | 0.8% mannitol | — | 6.0 | 1.02 | 3.38 | 0.014 |
| 2K | 0.8% mannitol | 10 mM Met | 6.0 | 0.99 | 3.26 | 0.014 |
| 2L | 0.8% mannitol | — | 6.4 | 3.88 | 5.80 | 0.025 |
| 2M | 0.8% mannitol | 10 mM Met | 6.4 | 3.74 | 5.61 | 0.022 |
| 3G | 1.4% trehalose | — | 4.5 | 2.75 | 54.87 | 0.028 |
| 3H | 1.4% trehalose | 10 mM Met | 4.5 | 2.75 | 50.90 | 0.020 |
| 3J | 1.4% trehalose | — | 6.0 | 0.91 | 3.37 | 0.014 |
| 3K | 1.4% trehalose | 10 mM Met | 6.0 | 0.89 | 3.20 | 0.014 |
| 3L | 1.4% trehalose | — | 6.4 | 3.79 | 5.79 | 0.022 |
| 3M | 1.4% trehalose | 10 mM Met | 6.4 | 3.74 | 5.51 | 0.020 |
| 4G | 0.8% sorbitol | — | 4.5 | 2.77 | 55.48 | 0.023 |
| 4H | 0.8% sorbitol | 10 mM Met | 4.5 | 2.76 | 51.85 | 0.018 |
| 4J | 0.8% sorbitol | — | 6.0 | 0.89 | 3.39 | 0.018 |
| 4K | 0.8% sorbitol | 10 mM Met | 6.0 | 0.98 | 3.25 | 0.015 |
| 4L | 0.8% sorbitol | — | 6.4 | 3.71 | 5.64 | 0.023 |
| 4M | 0.8% sorbitol | 10 mM Met | 6.4 | 3.67 | 5.49 | 0.020 |
| 5G | 0.4% glycine | — | 4.5 | 2.83 | 27.06 | 0.015 |
| 5H | 0.4% glycine | 10 mM Met | 4.5 | 2.83 | 25.90 | 0.015 |
| 5J | 0.4% glycine | — | 6.0 | 1.00 | 3.53 | 0.016 |
| 5K | 0.4% glycine | 10 mM Met | 6.0 | 1.02 | 3.31 | 0.014 |
| 5L | 0.4% glycine | — | 6.4 | 3.66 | 5.82 | 0.022 |
| 5M | 0.4% glycine | 10 mM Met | 6.4 | 3.62 | 5.50 | 0.024 |
| 6G | 1.4% HPBC | — | 4.5 | 2.73 | 60.52 | 0.024 |
| 6H | 1.4% HPBC | 10 mM Met | 4.5 | 2.74 | 56.97 | 0.020 |
| 6J | 1.4% HPBC | — | 6.0 | 0.99 | 3.53 | 0.017 |
| 6K | 1.4% HPBC | 10 mM Met | 6.0 | 0.97 | 3.36 | 0.016 |
| 6L | 1.4% HPBC | — | 6.4 | 3.82 | 5.90 | 0.029 |
| 6M | 1.4% HPBC | 10 mM Met | 6.4 | 3.91 | 5.76 | 0.029 |
| 7G | 0.8% arginine | — | 4.5 | DNT[1] | DNT[1] | 1.061 |
| 7H | 0.8% arginine | 10 mM Met | 4.5 | DNT[1] | DNT[1] | 1.090 |
| 7J | 0.8% arginine | — | 6.0 | 0.94 | 6.36 | 0.019 |
| 7K | 0.8% arginine | 10 mM Met | 6.0 | 0.89 | 6.03 | 0.020 |
| 7L | 0.8% arginine | — | 6.4 | 4.05 | 6.23 | 0.098 |
| 7M | 0.8% arginine | 10 mM Met | 6.4 | 3.74 | 6.20 | 0.044 |
| 8G | 0.8% proline | — | 4.5 | 2.80 | 35.98 | 0.019 |
| 8H | 0.8% proline | 10 mM Met | 4.5 | 2.80 | 34.40 | 0.015 |
| 8J | 0.8% proline | — | 6.0 | 1.00 | 3.50 | 0.016 |
| 8K | 0.8% proline | 10 mM Met | 6.0 | 0.90 | 3.32 | 0.015 |
| 8L | 0.8% proline | — | 6.4 | 3.73 | 5.86 | 0.026 |
| 8M | 0.8% proline | 10 mM Met | 6.4 | 3.73 | 5.61 | 0.022 |

[1]Did not test.

Example 12

Evaluation of Pembrolizumab Formulations Comprising Methionine and DTPA at Various Concentrations Previous studies suggested that the addition of methionine (anti-oxidant) and a metal chelator may have benefit in reducing aggregation (see Example 10). In order to investigate the impact of anti-oxidant and metal chelator concentration on suppressing the propensity for aggregation, a series of compositions were formulated and tested as described below. Pembrolizumab (20 mg/mL)/PS80 (0.16 mg/mL) stock solution in histidine pH 5.5 buffer was prepared as previously described in Example 9. Stock solutions (20 mg/mL) of the various stabilizers (sucrose, mannitol, trehalose, sorbitol, glycine, HPBC, arginine, and proline) were spiked into the pembro/PS80 stock solution. Methionine was used as the anti-oxidant and DTPA was used as the metal chelator. As noted prior, all stock solutions used for formulations were filtered through Millapore Express® PLUS Stericup® 0.22 µm PES filters prior to use. Final formulations of the compositions listed in Table 26 were prepared by spiking stock solutions of methionine (20 mg/mL) and DTPA (0.1 mg/mL) into the pembro/PS80/stabilizer solution in a 96-well plate and then bringing to a final volume of 1 mL with histidine pH 5.5 buffer. The well plate was covered with a 96-well silicone sealing mat and then was vacuum sealed (2×) in moisture barrier bags to minimize potential evaporation. Samples were staged in 5° C. and 50° C. environmental stability chambers for time period of 10 days.

TABLE 26

Pembrolizumab Formulations Comprising Methionine
and DTPA at Various Concentrations.

| Form.[1] | Stabilizer | Met.[2] (mM) | DTPA (µM) |
|---|---|---|---|
| 1N | 1.4% sucrose | — | — |
| 1P | 1.4% sucrose | 5 | 10 |
| 1Q | 1.4% sucrose | 15 | 10 |
| 1R | 1.4% sucrose | 10 | 20 |
| 1S | 1.4% sucrose | 5 | 30 |
| 1T | 1.4% sucrose | 15 | 30 |
| 1U | 1.4% sucrose | 5 | — |
| 1V | 1.4% sucrose | 10 | — |
| 1W | 1.4% sucrose | 15 | — |
| 1X | 1.4% sucrose | — | 10 |
| 1Y | 1.4% sucrose | — | 20 |
| 1Z | 1.4% sucrose | — | 30 |
| 2N | 0.8% mannitol | — | — |
| 2P | 0.8% mannitol | 5 | 10 |
| 2Q | 0.8% mannitol | 15 | 10 |
| 2R | 0.8% mannitol | 10 | 20 |
| 2S | 0.8% mannitol | 5 | 30 |
| 2T | 0.8% mannitol | 15 | 30 |
| 3N | 1.4% trehalose | — | — |
| 3P | 1.4% trehalose | 5 | 10 |
| 3Q | 1.4% trehalose | 15 | 10 |
| 3R | 1.4% trehalose | 10 | 20 |
| 3S | 1.4% trehalose | 5 | 30 |
| 3T | 1.4% trehalose | 15 | 30 |
| 4N | 0.8% sorbitol | — | — |
| 4P | 0.8% sorbitol | 5 | 10 |
| 4Q | 0.8% sorbitol | 15 | 10 |
| 4R | 0.8% sorbitol | 10 | 20 |
| 4S | 0.8% sorbitol | 5 | 30 |
| 4T | 0.8% sorbitol | 15 | 30 |
| 5N | 0.4% glycine | — | — |
| 5P | 0.4% glycine | 5 | 10 |
| 5Q | 0.4% glycine | 15 | 10 |
| 5R | 0.4% glycine | 10 | 20 |
| 5S | 0.4% glycine | 5 | 30 |
| 5T | 0.4% glycine | 15 | 30 |
| 6N | 1.4% HPBC | — | — |
| 6P | 1.4% HPBC | 5 | 10 |
| 6Q | 1.4% HPBC | 15 | 10 |
| 6R | 1.4% HPBC | 10 | 20 |
| 6S | 1.4% HPBC | 5 | 30 |
| 6T | 1.4% HPBC | 15 | 30 |
| 7N | 0.8% arginine | — | — |
| 7P | 0.8% arginine | 5 | 10 |

TABLE 26-continued

Pembrolizumab Formulations Comprising Methionine and DTPA at Various Concentrations.

| Form.[1] | Stabilizer | Met.[2] (mM) | DTPA (μM) |
|---|---|---|---|
| 7Q | 0.8% arginine | 15 | 10 |
| 7R | 0.8% arginine | 10 | 20 |
| 7S | 0.8% arginine | 5 | 30 |
| 7T | 0.8% arginine | 15 | 30 |
| 7N | 0.8% proline | — | — |
| 7P | 0.8% proline | 5 | 10 |
| 7Q | 0.8% proline | 15 | 10 |
| 7R | 0.8% proline | 10 | 20 |
| 7S | 0.8% proline | 5 | 30 |
| 7T | 0.8% proline | 15 | 30 |

[1]All formulations comprised 5 mg/mL pembrolizumab, 10 mM Histidine buffer, pH 5.5, and 0.004% PS80 in addition to the excipients listed.
[2]Methionine The formulations were evaluated by visual observation, turbidity (A350), UP-SEC (purity), HP-IEX (charge profile). After the 10 day test period at 50° C., no formulations were visibly turbid or experienced a color change. Turbidity values for all formulations (with the exception of arginine formulations 7N-7T) were very similar across the various formulations tested and closely resembled value shown in Example 9 (data not shown). From the turbidity data, the effect of the addition of different concentrations of methionine alone or in combination with different concentrations of DPTA, was not evident. Similar to the results shown in Examples 9 and 10, formulations comprising arginine showed the largest increase in % HMW species (Table 27) over the stability testing period, albeit formulations 7Q and 7T (15 mM methionine) showed slightly less % HMW species, suggesting potential increased stability of these formulations over others with lower concentrations of methionine. A similar trend was observed for all other formulations where the lowest % HMW species were observed in formulations having 15 mM methionine and at least 10 μM DTPA incorporated, although the difference was very small.

There were no appreciable differences in charge profile among any of the formulations (with the exclusion of 7C-7F which were not tested) at 50° C. for the 10-day testing period. However, there was a significant decrease in the % main peak (~53%→~41%) and increase in the % acidic variants and % pre-main peak for all formulations when compared to the formulations stored at 5° C. for 10 days (data not shown).

TABLE 27

Pembrolizumab Formulations Comprising Methionine and DTPA at Various Concentrations.

| | | | | % Aggregates (UP-SEC) | |
|---|---|---|---|---|---|
| Formulation | Stabilizer | Methionine (mM) | DTPA (μM) | 10 d/ 5° C. | 10 d/ 50° C. |
| 1N | 1.4% sucrose | — | — | 0.92 | 5.1 |
| 1P | 1.4% sucrose | 5 | 10 | 0.91 | 4.85 |
| 1Q | 1.4% sucrose | 15 | 10 | 0.92 | 4.73 |
| 1R | 1.4% sucrose | 10 | 20 | 0.91 | 4.8 |
| 1S | 1.4% sucrose | 5 | 30 | 0.92 | 4.75 |
| 1T | 1.4% sucrose | 15 | 30 | 0.92 | 4.54 |
| 1U | 1.4% sucrose | 5 | — | 0.86 | 4.64 |
| 1V | 1.4% sucrose | 10 | — | 0.92 | 4.55 |
| 1W | 1.4% sucrose | 15 | — | 0.92 | 4.48 |
| 1X | 1.4% sucrose | — | 10 | 0.92 | 4.8 |
| 1Y | 1.4% sucrose | — | 20 | 0.91 | 4.79 |
| 1Z | 1.4% sucrose | — | 30 | 0.87 | 4.82 |
| 2N | 0.8% mannitol | — | — | 0.86 | 5.37 |
| 2P | 0.8% mannitol | 5 | 10 | 0.92 | 5.14 |
| 2Q | 0.8% mannitol | 15 | 10 | 0.92 | 4.96 |
| 2R | 0.8% mannitol | 10 | 20 | 0.91 | 5.07 |
| 2S | 0.8% mannitol | 5 | 30 | 0.86 | 5.03 |
| 2T | 0.8% mannitol | 15 | 30 | 0.94 | 4.84 |
| 3N | 1.4% trehalose | — | — | 0.86 | 5.03 |
| 3P | 1.4% trehalose | 5 | 10 | 0.87 | 4.78 |
| 3Q | 1.4% trehalose | 15 | 10 | 0.92 | 4.64 |
| 3R | 1.4% trehalose | 10 | 20 | 0.87 | 4.70 |
| 3S | 1.4% trehalose | 5 | 30 | 0.86 | 4.69 |
| 3T | 1.4% trehalose | 15 | 30 | 0.87 | 4.53 |
| 4N | 0.8% sorbitol | — | — | 0.77 | 5.3 |
| 4P | 0.8% sorbitol | 5 | 10 | 0.93 | 5.1 |
| 4Q | 0.8% sorbitol | 15 | 10 | 0.85 | 4.9 |
| 4R | 0.8% sorbitol | 10 | 20 | 0.85 | 5.0 |
| 4S | 0.8% sorbitol | 5 | 30 | 0.91 | 4.94 |
| 4T | 0.8% sorbitol | 15 | 30 | 0.92 | 4.82 |
| 5N | 0.4% glycine | — | — | 0.9 | 5.12 |
| 5P | 0.4% glycine | 5 | 10 | 0.86 | 5.03 |
| 5Q | 0.4% glycine | 15 | 10 | 0.91 | 4.85 |
| 5R | 0.4% glycine | 10 | 20 | 0.93 | 4.96 |
| 5S | 0.4% glycine | 5 | 30 | 0.91 | 4.9 |
| 5T | 0.4% glycine | 15 | 30 | 0.89 | 4.75 |
| 6N | 1.4% HPBC | — | — | 0.91 | 5.03 |
| 6P | 1.4% HPBC | 5 | 10 | 0.91 | 5.08 |
| 6Q | 1.4% HPBC | 15 | 10 | 0.92 | 4.85 |
| 6R | 1.4% HPBC | 10 | 20 | 0.92 | 4.98 |
| 6S | 1.4% HPBC | 5 | 30 | 0.91 | 5.13 |

TABLE 27-continued

Pembrolizumab Formulations Comprising Methionine and DTPA at Various Concentrations.

| | | | | % Aggregates (UP-SEC) | |
|---|---|---|---|---|---|
| Formulation | Stabilizer | Methionine (mM) | DTPA (µM) | 10 d/ 5° C. | 10 d/ 50° C. |
| 6T | 1.4% HPBC | 15 | 30 | 0.87 | 4.9 |
| 7N | 0.8% arginine | — | — | 1.32 | 30.89 |
| 7P | 0.8% arginine | 5 | 10 | 1.34 | 30.12 |
| 7Q | 0.8% arginine | 15 | 10 | 1.54 | 27.09 |
| 7R | 0.8% arginine | 10 | 20 | 1.54 | 28.89 |
| 7S | 0.8% arginine | 5 | 30 | 1.54 | 29.82 |
| 7T | 0.8% arginine | 15 | 30 | 1.53 | 27.39 |
| 7N | 0.8% proline | — | — | 0.93 | 5.21 |
| 7P | 0.8% proline | 5 | 10 | 0.86 | 4.93 |
| 7Q | 0.8% proline | 15 | 10 | 0.92 | 4.81 |
| 7R | 0.8% proline | 10 | 20 | 0.92 | 4.87 |
| 7S | 0.8% proline | 5 | 30 | 0.92 | 5.04 |
| 7T | 0.8% proline | 15 | 30 | 0.91 | 4.85 |

HP-HIC analysis was performed on select formulations shown in Table 27 in order to assess the impact of methionine and DTPA concentrations on stability and oxidation after 10 days at 50° C. Results for formulations 1N, 1Q and 1T indicate that the presence of 15 mM methionine resulted in the smallest change in oxidation over the stability time period. Overall, the results shown in Table 28 demonstrated that the addition of methionine to formulations resulted in a reduced oxidation rate in a concentration dependent manner (formulations 1U-1W). No additional benefit was observed upon addition of DTPA (formulations 1X-1Z) as a chelator even in conjunction with the addition of methionine (formulations 1N-1T).

TABLE 28

Pembrolizumab Formulations Comprising Methionine and DTPA at Various Concentrations.

| | | | | Met-105 (HP-HIC) | |
|---|---|---|---|---|---|
| Formulation | Stabilizer | Methionine (mM) | DTPA (µM) | 10 d/ 5° C. | 10 d/ 50° C. |
| 1N | 1.4% sucrose | — | — | 8.45 | 23.50 |
| 1P | 1.4% sucrose | 5 | 10 | 6.87 | 11.36 |
| 1Q | 1.4% sucrose | 15 | 10 | 6.69 | 11.56 |
| 1R | 1.4% sucrose | 10 | 20 | 6.90 | 9.38 |
| 1S | 1.4% sucrose | 5 | 30 | 7.13 | 11.15 |
| 1T | 1.4% sucrose | 15 | 30 | 6.80 | 8.56 |
| 1U | 1.4% sucrose | 5 | — | 6.91 | 10.11 |
| 1V | 1.4% sucrose | 10 | — | 6.76 | 8.88 |
| 1W | 1.4% sucrose | 15 | — | 6.71 | 8.37 |
| 1X | 1.4% sucrose | — | 10 | 8.00 | 25.05 |
| 1Y | 1.4% sucrose | — | 20 | 8.43 | 24.94 |
| 1Z | 1.4% sucrose | — | 30 | 8.16 | 25.37 |

Example 13

Evaluation of the Effect of pH on the Stability of Low Concentration Pembrolizumab Formulations in Combination with Methionine An additional study was undertaken to evaluate the impact of histidine buffer on the stability of pembrolizumab formulations. In order to do so, formulations shown in Example 9 were prepared in water-for-injection (without pH adjustment) instead of 10 mM histidine pH 5.5. Pembrolizumab drug substance (~45 mg/mL) in 10 mM histidine pH 5.5 buffer was dialyzed with water-for-injection (WFI) to a final concentration of 15.5 mg/mL. Pembrolizumab (15.5 mg/mL)/PS80 (0.16 mg/mL) stock solution was prepared by addition of PS80 to pembrolizumab solution (15.5 mg/mL) in WFI followed by filtration through a SteriFlip® 0.22 µm PVE filter unit. Formulations to be tested were prepared by spiking excipient stock solutions (prepared in WFI and filtered through 0.22 µm PVE filter) into pembrolizumab/PS80 stock solutions to yield concentrations shown in Table 29. Similar to the study in Examples 9 & 10, 10 mM methionine and either 20 µM DTPA or 50 µM EDTA was added to assess the ability to reduce aggregation over the stability testing period. Formulations were prepared in a 96-well plate with a final drug product volume of 1 mL. The well plate was sealed with a silicone sealing mat prior to vacuum sealing in moisture barrier bags (2 times). Formulations were staged at 5° C. and 50° C. for 10 days.

TABLE 29

Low Concentration Pembrolizumab Formulations Prepared in WFI.

| Form.[1] | Stabilizer | Anti-Oxidant (10 mM) | Metal Chelator |
|---|---|---|---|
| 1A' | 1.4% sucrose | — | — |
| 1B' | 1.4% sucrose | Met | — |
| 1C' | 1.4% sucrose | — | DTPA |
| 1D' | 1.4% sucrose | Met | DTPA |
| 1E' | 1.4% sucrose | — | EDTA |
| 1F' | 1.4% sucrose | Met | EDTA |
| 2A' | 0.8% mannitol | — | — |
| 2B' | 0.8% mannitol | Met | — |
| 2C' | 0.8% mannitol | — | DTPA |
| 2D' | 0.8% mannitol | Met | DTPA |
| 2E' | 0.8% mannitol | — | EDTA |
| 2F' | 0.8% mannitol | Met | EDTA |
| 3A' | 1.4% trehalose | — | — |
| 3B' | 1.4% trehalose | Met | — |
| 3C' | 1.4% trehalose | — | DTPA |
| 3D' | 1.4% trehalose | Met | DTPA |
| 3E' | 1.4% trehalose | — | EDTA |
| 3F' | 1.4% trehalose | Met | EDTA |
| 4A' | 0.8% sorbitol | — | — |
| 4B' | 0.8% sorbitol | Met | — |
| 4C' | 0.8% sorbitol | — | DTPA |
| 4D' | 0.8% sorbitol | Met | DTPA |
| 4E' | 0.8% sorbitol | — | EDTA |
| 4F' | 0.8% sorbitol | Met | EDTA |
| 5A' | 0.4% glycine | — | — |

TABLE 29-continued

Low Concentration Pembrolizumab Formulations Prepared in WFI.

| Form.[1] | Stabilizer | Anti-Oxidant (10 mM) | Metal Chelator |
|---|---|---|---|
| 5B' | 0.4% glycine | Met | — |
| 5C' | 0.4% glycine | — | DTPA |
| 5D' | 0.4% glycine | Met | DTPA |
| 5E' | 0.4% glycine | — | EDTA |
| 5F' | 0.4% glycine | Met | EDTA |
| 6A' | 1.4% HPBC | — | — |
| 6B' | 1.4% HPBC | Met | — |
| 6C' | 1.4% HPBC | — | DTPA |
| 6D' | 1.4% HPBC | Met | DTPA |
| 6E' | 1.4% HPBC | — | EDTA |
| 6F' | 1.4% HPBC | Met | EDTA |
| 7A' | 0.8% arginine | — | — |
| 7B' | 0.8% arginine | Met | — |
| 7C' | 0.8% arginine | — | DTPA |
| 7D' | 0.8% arginine | Met | DTPA |
| 7E' | 0.8% arginine | — | EDTA |
| 7F' | 0.8% arginine | Met | EDTA |
| 8A' | 0.8% proline | — | — |
| 8B' | 0.8% proline | Met | — |
| 8C' | 0.8% proline | — | DTPA |
| 8D' | 0.8% proline | Met | DTPA |
| 8E' | 0.8% proline | — | EDTA |
| 8F' | 0.8% proline | Met | EDTA |

[1]All formulations comprised 5 mg/mL pembrolizumab and 0.004% PS80 in addition to the excipients listed.

The prepared formulations were tested by visual appearance, differential scanning fluorimetry (thermal unfolding), turbidity, UP-SEC (purity), and HP-IEX (charge profile). No formulations exhibited a color change or were visibly turbid upon removing from stability conditions. The measured turbidity values were very similar across all formulations tested. In contrast to turbidity results measure for arginine formulations prepared in 10 mM histidine pH 5.5 buffer (7A-7F, Examples 1 and 2), formulations prepared in WFI (7A'-7F') showed significantly lower turbidity values after the stability testing period (data not shown).

In comparison to formulations prepared in Examples 9 and 10, analogous formulations prepared in WFI showed a moderate improvement in thermal unfolding behavior through a shift in Tm1 to higher temperature (Table 30). Exceptions to this statement are mannitol formulations 2E' (EDTA) and 2F' (Met+EDTA) which showed almost identical Tm1 values to those formulations prepared in Examples 9 and 10 (data not shown). Formulations 6A'-6F' showed no thermal transitions presumably as a result of SYPRO™ dye preferentially binding to the cyclodextrin pocket. For all formulations tested, the presence of EDTA (50 μM) alone as the metal chelator resulted in lower Tm1 values than corresponding formulations with Met, Met+DTPA, DTPA, or Met+EDTA.

The change in pH of the unbuffered formulations was measured over the stability testing period to assess the self-buffering ability of the pembrolizumab formulations (see Table 30). Formulations 1-5F' (Met+EDTA) showed the smallest change in pH over 10 days at 50° C. For Cavitron® (HPBC) formulations (6A'-6F') the smallest change in pH was observed in formulation 6B' which utilized methionine, while the smallest change in pH observed for arginine formulations (7A'-7F') was observed in formulation 7A' (no methionine or metal chelator).

TABLE 30

Pembrolizumab Formulations Prepared in WFI.

| Form. | Stabilizer | Anti-Oxidant (10 mM) | Metal Chelator | DSF (thermal unfolding) Tm1 (° C.) | pH 10 days/ 5° C. | pH 10 days/ 50° C. |
|---|---|---|---|---|---|---|
| 1A' | 1.4% sucrose | — | — | 66.0 | 5.92 | 5.71 |
| 1B' | 1.4% sucrose | Met | — | 60.8 | 6.22 | 5.73 |
| 1C' | 1.4% sucrose | — | DTPA | 65.4 | 6.00 | 5.53 |
| 1D' | 1.4% sucrose | Met | DTPA | 58.6 | 6.02 | 5.52 |
| 1E' | 1.4% sucrose | — | EDTA | 60.8 | 6.22 | 5.77 |
| 1F' | 1.4% sucrose | Met | EDTA | 65.2 | 5.79 | 5.75 |
| 2A' | 0.8% mannitol | — | — | 66.8 | 6.16 | 5.42 |
| 2B' | 0.8% mannitol | Met | — | 65.6 | 6.15 | 5.61 |
| 2C' | 0.8% mannitol | — | DTPA | 65.2 | 6.06 | 5.52 |
| 2D' | 0.8% mannitol | Met | DTPA | 65.0 | 5.92 | 5.52 |
| 2E' | 0.8% mannitol | — | EDTA | 58.6 | 5.45 | 5.71 |
| 2F' | 0.8% mannitol | Met | EDTA | 58.6 | 5.59 | 5.72 |
| 3A' | 1.4% trehalose | — | — | 65.4 | 6.14 | 5.78 |
| 3B' | 1.4% trehalose | Met | — | 65.8 | 6.33 | 5.80 |
| 3C' | 1.4% trehalose | — | DTPA | 65.4 | 6.07 | 5.63 |
| 3D' | 1.4% trehalose | Met | DTPA | 65.0 | 5.97 | 5.64 |
| 3E' | 1.4% trehalose | — | EDTA | 61.4 | 5.84 | 5.79 |
| 3F' | 1.4% trehalose | Met | EDTA | 65.6 | 5.79 | 5.82 |
| 4A' | 0.8% sorbitol | — | — | 65.4 | 6.01 | 5.85 |
| 4B' | 0.8% sorbitol | Met | — | 65.4 | 6.29 | 5.85 |
| 4C' | 0.8% sorbitol | — | DTPA | 66.0 | 6.04 | 5.66 |
| 4D' | 0.8% sorbitol | Met | DTPA | 65.6 | 6.02 | 5.67 |
| 4E' | 0.8% sorbitol | — | EDTA | 61.2 | 5.78 | 5.80 |
| 4F' | 0.8% sorbitol | Met | EDTA | 65.6 | 5.71 | 5.81 |
| 5A' | 0.4% glycine | — | — | 66.6 | 6.25 | 5.91 |
| 5B' | 0.4% glycine | Met | — | 65.2 | 6.33 | 5.91 |
| 5C' | 0.4% glycine | — | DTPA | 65.2 | 6.10 | 5.76 |
| 5D' | 0.4% glycine | Met | DTPA | 66.2 | 6.07 | 5.75 |
| 5E' | 0.4% glycine | — | EDTA | 65.4 | 6.04 | 5.90 |
| 5F' | 0.4% glycine | Met | EDTA | 65.4 | 5.92 | 5.89 |
| 6A' | 1.4% HPBC | — | — | — | 6.17 | 5.82 |
| 6B' | 1.4% HPBC | Met | — | — | 6.20 | 5.90 |
| 6C' | 1.4% HPBC | — | DTPA | — | 6.17 | 5.68 |
| 6D' | 1.4% HPBC | Met | DTPA | — | 6.04 | 5.66 |
| 6E' | 1.4% HPBC | — | EDTA | — | 6.23 | 5.87 |
| 6F' | 1.4% HPBC | Met | EDTA | — | 6.24 | 5.87 |
| 7A' | 0.8% arginine | — | — | 64.2 | 6.02 | 5.92 |
| 7B' | 0.8% arginine | Met | — | 58.8 | 6.21 | 5.95 |
| 7C' | 0.8% arginine | — | DTPA | 58.6 | 6.10 | 5.81 |
| 7D' | 0.8% arginine | Met | DTPA | 63.4 | 6.03 | 5.78 |
| 7E' | 0.8% arginine | — | EDTA | 64.2 | 6.24 | 5.85 |
| 7F' | 0.8% arginine | Met | EDTA | 64.2 | 6.21 | 5.94 |
| 8A' | 0.8% proline | — | — | 61.6 | 6.29 | 5.87 |
| 8B' | 0.8% proline | Met | — | 59.2 | 6.28 | 5.90 |
| 8C' | 0.8% proline | — | DTPA | 65.8 | 6.14 | 5.78 |
| 8D' | 0.8% proline | Met | DTPA | 59.0 | 6.11 | 5.73 |
| 8E' | 0.8% proline | — | EDTA | 59.0 | 6.30 | 5.93 |
| 8F' | 0.8% proline | Met | EDTA | 65.0 | 6.29 | 5.92 |

The amount of aggregation of each of the formulations over a 10 day time period at 50° C. was also measured by UP-SEC. The % mAb and % aggregates (HMW species) for all formulations tested were very similar with the exception of formulations 7A'-7F' (arginine formulations), which showed an increase in the % HMW species (~4%). From the UP-SEC data there was no clear evidence that the addition of methionine (10 mM), DTPA (20 μM), EDTA (50 μM) or combinations thereof, significantly reduced aggregation.

Charge profiles of formulations after 10 days at 50° C. was determined by HP-IEX (data not shown). All formulations showed similar charge profiles for each stabilizer tested. A significant decrease in the % main peak (~53%→~41%) and increase in the % acidic variants and % pre-main peak for all formulations was observed when compared to the formulations stored at 5° C. for 10 days (data not shown). Formulations prepared in WFI showed higher % acidic peaks (~28%) with comparable % pre-main peak and % basic variants to analogous formulations in Examples 9 and 10 after 10 days at 50° C. The addition of methionine, DTPA, EDTA, or combinations thereof, to the formulations did not result in any significant change in charge profile.

Example 14

Development of a High Concentration Lyophilized Drug Product Formulation Comprising Pembrolizumab A summary of the design of experiments and results from all the drug product batches is provided in Table 32. All formulations contained histidine buffer (pH 5.5) and polysorbate 80 (PS 80) as a surfactant. Various test formulations were manufactured using different cryoprotectants, stabilizers, etc., with varied concentrations of pembrolizumab and excipients. The following pembrolizumab drug substance batches were used to formulate the test formulations for the studies:

204 mg/mL pembrolizumab in 10 mM Histidine buffer, pH 5.5

288 mg/mL pembrolizumab in 3% Arginine.HCl, 10 mM Histidine buffer, pH 5.5

The lyophilization processes used for the studies were conducted using a model LYOSTAR 3 (SP Scientific) as described in Table 31.

Batch 0021:

Batch 0021 was manufactured starting with 103 mg/mL pembrolizumab formulated in sucrose. A volume of 2.30 mL was filled in 2R vials, 6R vials and 10R vials. A 55 hour lyophilization cycle was used ("lyo cycle A," see Table 31). Post-lyophilization, the residual moisture, syringeable volume, and expansion volume were measured. Generally a range of reconstitution times 17-28 minutes were observed.

Batch 0022:

Batch 0022 was manufactured starting with 48-103 mg/mL pembrolizumab formulated in various combinations of sucrose, mannitol and arginine hydrochloride (Arg.HCl). A volume of 2.30-4.97 mL was filled in 2R vials, 6R vials, 10R vials and 10R vials. A longer primary drying extended by 5 hours was adopted. Thus, the lyophilization cycle used was similar to lyophilization cycle A, extended to 60 hours ("lyo cycle B" see Table 31). Generally, reconstitution times ranged from 4 to 23 minutes. The residual moisture was from 0.24-0.26%.

Batch 0024:

Batch 0024 was manufactured starting with 104-200 mg/mL pembrolizumab formulated in various combinations of sucrose and arginine hydrochloride (Arg.HCl). Drug substance used was 288 mg/mL pembrolizumab in 3% Arg, 10 mM His pH 5.5. A volume of 1.24-2.30 mL was filled in 2R vials. For the lyophilization process, one shelf was fully loaded with 7% sucrose vials. The secondary drying time was reduced from 8 hours to 6 hours. Thus, the lyophilization cycle used had a 2 hour shorter secondary drying time compared to lyophilization cycle A ("lyo cycle C" see Table 31). Generally, reconstitution times ranged from 37 to 42 minutes. There were some difficulties in dissolving the lyophilization cake, which were not improved by the introduction of a centrifugation step. The residual moisture measured was 0.27%.

Batch 0025:

Batch 0025 was formulated with 25 mg/mL pembrolizumab formulated in sucrose. A volume of 10.66 mL was filled in 15R vials. A conservative version of lyophilization cycle A was adopted (approx. 136 hours, ("lyo cycle D" see Table 31). Among other changes, a longer primary drying step was used. Generally, reconstitution times ranged from 2 minutes, 20 sec to 4 minutes, 40 seconds. The residual moisture was from 0.4-0.5%.

Batch 0027:

Batch 0027 was formulated with 25 mg/mL and 35 mg/mL pembrolizumab in sucrose. A volume of 6.8-9.5 mL was filled in 15R vials. A conservative version of lyophilization cycle A was adopted (~136 hours, "lyo cycle E" see Table 31) with a longer primary drying step comprised of a two-step drying process (−20° C. and −10° C.). Vials were reconstituted with a lower volume (1.0 mL) of water. Generally, reconstitution times ranged from 4 minutes, 20 seconds to 6 minutes, 15 seconds. The residual moisture was from 0.14-0.17%. The rate of the syringe out of the reconstitution was extremely slow and difficult with a 3-mL syringe fitted with a 27G ½" needle.

Batch 0028:

Batch 0028 was formulated with (1) 25 mg/mL or 35 mg/mL pembrolizumab in sucrose, (volume of 6.78-9.6 mL, filled in 15R or 20R vials) or (2) 35 mg/mL pembrolizumab in arginine (volume 6.78 mL filled in 15R vials). Lyophilization cycle A was used without changes (approx. 55 hours). These vials were reconstituted with 1.2 mL water. Generally, reconstitution times ranged from 5 minutes, 10 seconds to 6 minutes, 15 seconds. The residual moisture was from 0.60-0.85%. 3-mL syringes fitted with 27G ½" needles were easier to fill and empty with the Arginine-containing reconstituted solution as compared to the sucrose formulations, which was assumed to be a result of viscosity.

This example evaluated lyophilized formulations that were made with starting solutions comprising 200 mg pembrolizumab at protein concentrations between 48 mg/mL-200 mg/mL. All formulations were lyophilized to yield a white cake. Following lyophilization, the cakes were reconstituted with SWFI and the reconstituted solutions were evaluated for tonicity, viscosity and reconstitution time. Lyo cakes were reconstituted with lesser water than the fill volume to achieve an approximate concentration of 167 mg/mL (i.e. 200 mg/vial). The lyo cakes manufactured with high concentration pre-lyo solutions (>100 mg/mL) were generally more compact in nature.

Reconstitution times for the different formulations varied from 2 to 42 minutes (see Table 32). In general, reconstitution times were longer with increasing protein concentration of pre-lyo solution. Results of the analysis of the reconstituted solution indicate that arginine hydrochloride had similar effect in reducing the reconstitution time as the excipients tested, but may help lower viscosity of the reconstituted solution. The impact of other excipients (e.g., sucrose, mannitol) and lyophilization process parameters on the reconstitution times were found to be negligible.

TABLE 31

Lyophilization Cycles Used for Example 14

| Batch No./ Lyo Cycle | Freezing | Primary Drying | Secondary Drying |
|---|---|---|---|
| 0021 Cycle A | Load 5° C. Ramp to −10° C., 20 m Hold at −10° C., 1 h Ramp to −50° C., 2 h 40 m Hold at −50° C., 1 h Ramp to −10° C., 1 h 20 m Hold at −10° C., 3 h Ramp to −50° C., 2 h 40 m Hold at −50° C., 1 h | Pressure set to 113 mTorr Ramp to −15° C., 45 m Hold at −15° C., 24 h Ramp to −5° C., 5 h | Pressure set to 113 mTorr Ramp to 30° C., 1 h 10 m Hold at 30° C., 8 h Ramp to 5° C., 30 m Backfill with nitrogen |
| 0022 Cycle B | Load 5° C. Ramp to −10° C., 20 m Hold at −10° C., 1 h Ramp to −50° C., 2 h 40 m Hold at −50° C., 1 h Ramp to −10° C., 1 h 20 m Hold at −10° C., 3 h Ramp to −50° C., 2 h 40 m Hold at −50° C., 1 h | Pressure set to 113 mTorr Ramp to −15° C., 45 m Hold at −15° C., 29 h Ramp to −5° C., 5 h | Pressure set to 113 mTorr Ramp to 30° C., 1 h 10 m Hold at 30° C., 8 h Ramp to 5° C., 30 m Backfill with nitrogen |
| 0024 Cycle C | Load 5° C. Ramp to −10° C., 20 m Hold at −10° C., 1 h Ramp to −50° C., 2 h 40 m Hold at −50° C., 1 h Ramp to −10° C., 1 h 20 m Hold at −10° C., 3 h Ramp to −50° C., 2 h 40 m Hold at −50° C., 1 h | Pressure set to 113 mTorr Ramp to −15° C., 45 m Hold at −15° C., 29 h Ramp to −5° C., 5 h | Pressure set to 113 mTorr Ramp to 30° C., 1 h 10 m Hold at 30° C., 6 h Ramp to 5° C., 30 m Backfill with nitrogen |
| 0025 Cycle D | Load 5° C. Ramp to −10° C., 20 m Hold at −10° C., 1 h Ramp to −50° C., 2 h 40 m Hold at −50° C., 1 h Ramp to −10° C., 1 h 20 m Hold at −10° C., 3 h Ramp to −50° C., 2 h 40 m Hold at −50° C., 1 h | Pressure set to 113 mTorr Ramp to −20° C., 2 h Hold at −20° C., 103 h Ramp to −5° C., 7 h 30 m | Pressure set to 113 mTorr Ramp to 30° C., 1 h 10 m Hold at 30° C., 8 h Ramp to 5° C., 30 m Backfill with nitrogen |
| 0027 Cycle E | Load 5° C. Ramp to −10° C., 20 m Hold at −10° C., 1 h Ramp to −50° C., 2 h 40 m Hold at −50° C., 1 h Ramp to −10° C., 1 h 20 m Hold at −10° C., 3 h Ramp to −50° C., 2 h 40 m Hold at −50° C., 1 h | Pressure set to 113 mTorr Ramp to −20° C., 5 h Hold at −20° C., 60 h Ramp to −15° C., 3 h Hold at −15° C., 31 h Ramp to −5° C., 9 h | Pressure set to 113 mTorr Ramp to 30° C., 6 h Hold at 30° C., 8 h Ramp to 5° C., 30 m Backfill with nitrogen |
| 0028 Cycle A | Load 5° C. Ramp to −10° C., 20 m Hold at −10° C., 1 h Ramp to −50° C., 2 h 40 m Hold at −50° C., 1 h Ramp to −10° C., 1 h 20 m Hold at −10° C., 3 h Ramp to −50° C., 2 h 40 m Hold at −50° C., 1 h | Pressure set to 113 mTorr Ramp to −15° C., 45 m Hold at −15° C., 24 h Ramp to −5° C., 5 h | Pressure set to 113 mTorr Ramp to 30° C., 1 h 10 m Hold at 30° C., 8 h Ramp to 5° C., 30 m Backfill with nitrogen |

TABLE 32

Results Summary for Lyophilization Experiments

| Batch# | Experiment | Formulation (pre-lyo) | Fill (mL)/ vial(s) | Reconstituted Formulation | Properties (% moisture, reconstitution data, etc.) |
|---|---|---|---|---|---|
| 0021 | 103 mg/mL with sucrose | 6.18 mM his pH 5.5, 4.32% suc, 0.01% PS 80 | Fill 2.3 mL/2R, 6R, 10R vials | 166.7 mg/mL pembro, 10 mM his pH 5.5, 7% suc, 0.02% PS 80 | 6R: 0.10%; 1.0 mL water-21 m (170 mg/mL) 10R: 0.11%; 1.0 mL water-17 m 2R: 0.13%; 1.0 mL water-28 m |
| 0022A | 103 mg/mL with Mannitol/ Sucrose | 6.2 mM His, 1.04% Suc, 2.6% mannitol, 0.12% PS80 | 2.3 mL in 2R and 6R vials | 166.7 mg/mL pembro, 4.2% Mannitol, 1.68% Suc, 10 mM His, 0.02% PS80 | 23 m with 1.1 mL water |

TABLE 32-continued

Results Summary for Lyophilization Experiments

| Batch# | Experiment | Formulation (pre-lyo) | Fill (mL)/vial(s) | Reconstituted Formulation | Properties (% moisture, reconstitution data, etc.) | | |
|---|---|---|---|---|---|---|---|
| 0022B | 75 mg/mL with Sucrose | 4.5 mM His, 3.15% Suc, 0.014% PS 80 | 3.2 mL in 6R, 10R vials | 166.7 mg/mL pembro, 10 mM His, 7% Suc, 0.03% PS 80 | 15 m with 1.1 mL water | | |
| 0022C | 55.3 mg/mL with Sucrose | 2.32% Suc, 3.32 mM His, 0.01% PS 80 | 4.34 mL in 10R, 15R vials | 166.7 mg/mL pembro, 7% Suc, 10 mM His, 0.03% PS-80 | 4 m with 1.1 mL water (131.6 mg/mL) | Moisture 0.21% (15 mL vial) | |
| 0022D | 48.33 mg/mL with Suc/Arg | 1% Arg, 1.83% Suc, 3.32 mM His, 0.01% PS-80 | 4.97 mL in 10R, 15R vials | 166.7 mg/mL pembro, 3% Arg, 5.5% Suc, 10 mM His, 0.03% PS-80 | 5 m with 1.1 mL water in 10R vial (142.9 mg/mL) | 4 m with 1.1 mL water in 15R vial (158.8 mg/mL) | Moisture 0.24% (10 mL vial), 0.26% (15 mL vial) |
| 0022E | 55.3 mg/mL with Arg | 1% Arg, 3.32 mM His, 0.01% PS 80 | 4.34 mL in 15R vials | 166.7 mg/mL pembro, 3% Arg, 10 mM His, 0.03% PS-80 | 10 m with 1.1 mL water (173 mg/mL) | | |
| 0024A | 104 mg/mL with Suc/Arg | 3.13% Suc, 1.25% Arg•HCl, 0.01% PS-80 in 6.26 mM His | 2.3 mL in 2R vials | 166.7 mg/mL pembro, 5% Suc, 2% Arg, 0.02% PS-80 in 10 mM His | 40 m with 1.2 mL water, 169.4 mg/mL; with 0.9% saline > 50 m | Centrifuge reconst: 45 m, no foaming (×1000-3000 g) | Could not be dissolved in methanol |
| 0024B | 104 mg/mL with Suc/Arg | 2.32% Suc, 1.25% Arg•HCl, 0.01% PS-80 in 6.26 mM His | 2.3 mL in 2R vials | 166.7 mg/mL pembro 3.7% Suc, 2% Arg, 0.02% PS 80, 10 mM His | 37 m with 1.2 mL water, 165.3 mg/mL | Centrifuge reconst: 35 m, no foaming (×1000-3000 g) | Moisture 0.27% |
| 0024C | 200 mg/mL with Suc/Arg | 3.7% Suc, 2.08% Arg•HCl, 0.02% PS-80 in 10 mM His | 1.24 mL in 2R vials | 166.7 mg/mL pembro, 3.7% Suc, 2% Arg, 0.02% PS 80, 8.3 mM His | 42 m with 1.2 mL water, 173.7 mg/mL | Centrifuge reconst: 45 m, no foaming (×3000 g) | Could not be dissolved in methanol |
| 0025A | 25 mg/mL with Sucrose | 1.05% Suc, 1.5 mM His, 0.003% PS-80 | 10.66 mL in 15R vial | 166.7 mg/mL pembro, 7% Suc, 0.02% PS 80, 10 mM His | 4 m 40 s with 1.2 mL water; 183 mg/mL | Moisture 0.5% | |
| 0025B | 25 mg/mL with Sucrose | 2.10% Suc, 1.5 mM His, 0.003% PS-80 | 10.66 mL in 15R vial | 166.7 mg/mL pembro, 14% Suc, 0.02% PS 80, 10 mM His | 2 m 20 s with 1.2 mL water; 173 mg/mL | Moisture 0.4% | |
| 0027A | 35 mg/mL with Sucrose | 1.47% Suc, 2.1 mM His, 0.004% PS-80 | 6.8 mL in 15R vials | 166.7 mg/mL pembro, 7% Suc, 0.02% PS 80, 10 mM His | 6 m 15 s with 1.0 mL water (189 mg/mL) | Moisture 0.17% | 1.1 mL solution syringed out; rate- very slow with 3-mL syringe fitted with a 27G ½" needle |
| 0027B | 25 mg/mL with Suc | 1.05% Suc, 1.5 mM His, 0.003% PS-80 | 9.5 mL in 15R and 20R vials | 166.7 mg/mL pembro, 7% Suc, 0.02% PS 80, 10 mM His | 4 m 20 s with 1.0 mL water (194 mg/mL) | Moisture 0.16% (15R vial); 0.14% (20R vial) | 1.1 mL solution syringed out; rate- very slow with 3-mL syringe fitted with a 27G ½" needle |
| 0028A | 35 mg/mL with Suc | 1.454% Suc, 2.07 mM His, 0.004% PS-80 | 6.78 mL in 15R vials | 166.7 mg/mL pembro, 7% Suc, 0.02% PS-80 in 10 mM His | 5 m 20 s with 1.2 mL water (166 mg/mL) | Moisture 0.60% | Vol of DP syringed out, 3 mL syr + 27G 0.5" needle (mL) = 1.3 mL (Label vol = 1.2 mL) |
| 0028B | 25 mg/mL with Suc | 1.04% Suc, 1.48 mM His, 0.003% PS-80 | 9.60 mL in 20R vials | 166.7 mg/mL pembro, 7% Suc, 0.02% PS-80 in 10 mM His | 6 m 15 s with 1.2 mL water (165 mg/mL) | Moisture 0.85% | Vol of DP syringed out, 3 mL syr + 27G 0.5" needle (mL) = 1.3 mL (Label vol = 1.2 mL) |
| 0028C | 35 mg/mL with Arg•HCl | 0.623% Arg, 2.07 mM His, 0.0042% PS-80 | 6.78 mL in 15R vials | 166.7 mg/mL pembro, 3% Arg, 0.02% PS-80 in 10 mM His | 5 m 10 s with 1.2 mL water (169 mg/mL) | Moisture 0.81% | Vol of DP syringed out, 3 mL syr + 27G 0.5" needle (mL) = 1.3 mL (Label vol = 1.2 mL); easier to fill in the syringe |

What is claimed is:

1. An anti-human programmed death receptor 1 (PD-1) antibody formulation, comprising:
   a) about 100 mg/mL to about 200 mg/mL of an anti-human PD-1 antibody, or antigen binding fragment thereof;
   b) about 5 mM to about 20 mM histidine buffer;
   c) about 6% to about 8% weight/volume (w/v) sucrose;
   d) about 0.01% to about 0.10% polysorbate 80; and
   e) about 1 mM to about 20 mM L-methionine, or a pharmaceutically acceptable salt thereof,
   wherein the anti-human PD-1 antibody or antigen binding fragment thereof comprises three light chain CDRs comprising CDRL1 of SEQ ID NO:1, CDRL2 of SEQ ID NO:2 and CDRL3 of SEQ ID NO:3 and three heavy chain CDRs of CDRH1 of SEQ ID NO:6, CDRH2 of SEQ ID NO:7 and CDRH3 of SEQ ID NO:8.

2. The anti-human PD-1 antibody formulation of claim 1, wherein the formulation has a pH between 5.0 and 6.0.

3. The anti-human PD-1 antibody formulation of claim 1, further comprising from about 1% to about 3% w/v L-arginine, or a pharmaceutically acceptable salt thereof.

4. The anti-human PD-1 antibody formulation of claim 1, comprising:
   a) about 100 to about 200 mg/mL of an anti-human PD-1 antibody, or antigen binding fragment thereof;
   b) 8 mM to about 12 mM histidine buffer;
   c) about 5 mM to about 10 mM L-methionine, or a pharmaceutically acceptable salt thereof;

d) about 6% to about 8% w/v sucrose; and
e) 0.01% to about 0.04% w/v polysorbate 80.

5. The anti-human PD-1 antibody formulation of claim 4, comprising:
   a) about 125 to about 200 mg/mL of an anti-human PD-1 antibody, or antigen binding fragment thereof;
   b) about 10 mM histidine buffer;
   c) about 10 mM L-methionine, or a pharmaceutically acceptable salt thereof;
   d) about 7% w/v sucrose; and
   e) about 0.02% to w/v polysorbate 80.

6. The anti-human PD-1 antibody formulation of claim 5, wherein the antioxidant is L-methionine HCl.

7. The anti-human PD-1 antibody formulation of claim 5, further comprising from about 1.25% to about 2.5% w/v L-arginine, or a pharmaceutically acceptable salt thereof.

8. The anti-human PD-1 antibody formulation of claim 1, wherein the formulation further comprises a metal chelator.

9. The anti-human PD-1 antibody formulation of claim 8, wherein the metal chelator is diethylenetriaminepentaacetic acid (DTPA), which is present at a concentration of about 10 µM to about 30 µM.

10. The anti-human PD-1 antibody formulation of claim 1 that is a reconstituted solution from a lyophilized formulation.

11. The anti-human PD-1 antibody formulation of claim 1, wherein the anti-human PD-1 antibody or antigen binding fragment thereof comprises a $V_L$ region which comprises the amino acid sequence set forth in SEQ ID NO:4, and a $V_H$ region which comprises the amino acid sequence set forth in SEQ ID NO:9.

12. The anti-human PD-1 antibody formulation of claim 1, wherein the formulation comprises a light chain comprising or consisting of a sequence of amino acids as set forth in SEQ ID NO:5 and a heavy chain comprising or consisting of a sequence of amino acids as set forth in SEQ ID NO: 10.

13. The anti-human PD-1 antibody formulation of claim 1, wherein the formulation comprises an anti-human PD-1 antibody that is pembrolizumab.

14. The formulation of claim 13, wherein the formulation is contained in an injection device.

15. The formulation of claim 13, wherein the formulation is contained in a glass vial.

16. The anti-human PD-1 antibody formulation of claim 1, wherein the concentration of the anti-human PD-1 antibody or antigen binding fragment thereof is about 165 to about 170 mg/ml.

17. A method of treating chronic infection in a human patient in need thereof comprising: administering to the human patient an effective amount of an anti-human PD-1 antibody formulation comprising:
   a) about 100 mg/mL to about 200 mg/mL of an anti-human PD-1 antibody, or antigen binding fragment thereof;
   b) about 5 mM to about 20 mM histidine buffer;
   c) about 6% to about 8% weight/volume (w/v) sucrose;
   d) about 0.01% to about 0.10% polysorbate 80; and
   e) about 1 mM to about 20 mM L-methionine, or a pharmaceutically acceptable salt thereof,
   wherein the anti-human PD-1 antibody or antigen binding fragment thereof comprises three light chain CDRs comprising CDRL1 of SEQ ID NO:1, CDRL2 of SEQ ID NO:2 and CDRL3 of SEQ ID NO:3 and three heavy chain CDRs of CDRH1 of SEQ ID NO:6, CDRH2 of SEQ ID NO:7 and CDRH3 of SEQ ID NO:8.

18. A method of treating cancer in a human patient in need thereof, the method comprising administering to the human patient an effective amount of an anti-human PD-1 antibody formulation comprising:
   a) about 100 mg/mL to about 200 mg/mL of an anti-human PD-1 antibody, or antigen binding fragment thereof;
   b) about 5 mM to about 20 mM histidine buffer;
   c) about 6% to about 8% weight/volume (w/v) sucrose;
   d) about 0.01% to about 0.10% polysorbate 80; and
   e) about 1 mM to about 20 mM L-methionine, or a pharmaceutically acceptable salt thereof,
   wherein the anti-human PD-1 antibody or antigen binding fragment thereof comprises three light chain CDRs comprising CDRL1 of SEQ ID NO:1, CDRL2 of SEQ ID NO:2 and CDRL3 of SEQ ID NO:3 and three heavy chain CDRs of CDRH1 of SEQ ID NO:6, CDRH2 of SEQ ID NO:7 and CDRH3 of SEQ ID NO:8.

19. The method of claim 18, wherein the anti-human PD-1 antibody formulation is administered by subcutaneous administration.

20. The method of claim 19, wherein the anti-human PD-1 antibody is pembrolizumab.

21. A method of treating cancer in a human patient in need thereof, the method comprising administering to the human patient an effective amount of an anti-human PD-1 antibody formulation comprising:
   a) about 125 mg/mL to about 200 mg/mL of an anti-human PD-1 antibody, or antigen binding fragment thereof;
   b) about 10 mM histidine buffer,
   c) about 7% w/v sucrose,
   d) about 0.02% polysorbate 80,
   e) about 10 mM L-methionine, or a pharmaceutically acceptable salt thereof,
   f) a pH between 5.0 and 6.0,
   wherein the anti-human PD-1 antibody or antigen binding fragment thereof is pembrolizumab,
   wherein the formulation is administered by subcutaneous administration.

* * * * *